US011634500B2

(12) United States Patent
Grandal et al.

(10) Patent No.: US 11,634,500 B2
(45) Date of Patent: Apr. 25, 2023

(54) ANTI-CD73 ANTIBODIES AND COMPOSITIONS

(71) Applicant: LES LABORATOIRES SERVIER, Suresnes (FR)

(72) Inventors: Michael Monrad Grandal, Ballerup (DK); Torben Gjetting, Jyllinge (DK); Johan Lantto, Lund (SE); Janus Schou Jakobsen, Gentofte (DK); Randi Westh Hansen, Roskilde (DK); Camilla Fröhlich, København Ø (DK)

(73) Assignee: LES LABORATOIRES SERVIER, Suresnes (FR)

( * ) Notice: Subject to any disclaimer, the term of this patent is extended or adjusted under 35 U.S.C. 154(b) by 128 days.

(21) Appl. No.: 17/012,942

(22) Filed: Sep. 4, 2020

(65) Prior Publication Data
US 2021/0070876 A1    Mar. 11, 2021

Related U.S. Application Data

(60) Provisional application No. 62/896,908, filed on Sep. 6, 2019.

(51) Int. Cl.
*C07K 16/28* (2006.01)
*A61P 35/00* (2006.01)
*A61K 45/06* (2006.01)

(52) U.S. Cl.
CPC .......... *C07K 16/2896* (2013.01); *A61P 35/00* (2018.01); *A61K 45/06* (2013.01); *C07K 2317/31* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 8,975,081 | B2 | 3/2015 | Jalkanen et al. |
| 10,011,829 | B2* | 7/2018 | Fan ..................... C12N 15/1037 |
| 10,059,761 | B2* | 8/2018 | Tam ........................ A61P 37/06 |
| 10,100,129 | B2 | 10/2018 | Lonberg et al. |
| 10,179,819 | B2* | 1/2019 | Kirshner ............ C07K 16/3069 |
| 10,584,169 | B2 | 3/2020 | Wang et al. |
| 10,766,966 | B2 | 9/2020 | Perrot et al. |
| 10,822,426 | B2 | 11/2020 | Griffin et al. |

(Continued)

FOREIGN PATENT DOCUMENTS

| WO | WO 00/67796 | 11/2000 |
| WO | WO 01/80884 | 11/2001 |

(Continued)

OTHER PUBLICATIONS

Allard et al., "CD73-adenosine: a next-generation target in immuno-oncology," Immunotherapy (2016) 8(2):145-63.

(Continued)

*Primary Examiner* — Scarlett Y Goon
*Assistant Examiner* — Miles Joseph Delahoussaye
(74) *Attorney, Agent, or Firm* — Steptoe & Johnson LLP; Z. Ying Li; Wyan-Ching M. Lee

(57) ABSTRACT

This invention relates to anti-CD73 antibodies and methods of using them in treating diseases and conditions related to CD73 activity, e.g., cancer.

20 Claims, 23 Drawing Sheets

Specification includes a Sequence Listing.

(56) References Cited

U.S. PATENT DOCUMENTS

| | | |
|---|---|---|
| 11,130,817 B2 | 9/2021 | Caux et al. |
| 2007/0009518 A1 | 1/2007 | Novobrantseva et al. |
| 2009/0202431 A1 | 8/2009 | Gibbs et al. |
| 2016/0129108 A1 | 5/2016 | Sachsenmeier et al. |
| 2018/0009899 A1 | 1/2018 | Griffin et al. |
| 2018/0030144 A1 | 2/2018 | Chanteux et al. |
| 2020/0148781 A1 | 5/2020 | Zeidler et al. |
| 2020/0232974 A1 | 7/2020 | Menetrier-Caux et al. |
| 2021/0107989 A1 | 4/2021 | Griffin et al. |

FOREIGN PATENT DOCUMENTS

| | | |
|---|---|---|
| WO | WO 2004/079013 | 9/2004 |
| WO | WO 2004/091657 | 10/2004 |
| WO | WO 2007/062090 | 5/2007 |
| WO | WO 2014/153424 | 9/2014 |
| WO | WO 2016/075099 | 5/2016 |
| WO | WO 2016/081748 | 5/2016 |
| WO | WO 2016/196912 | 12/2016 |
| WO | WO 2017/064043 | 4/2017 |
| WO | WO 2018/237157 | 12/2018 |
| WO | WO 2019/173692 | 9/2019 |

OTHER PUBLICATIONS

Allard et al., "The ectonucleotidases CD39 and CD73: Novel checkpoint inhibitor targets," Immunol Rev. (2017) 276(1):121-144.

Geoghegan et al., "Inhibition of CD73 AMP hydrolysis by a therapeutic antibody with a dual, non-competitive mechanism of action," MAbs. (2016) 8(3):454-67.

Knapp et al., "Crystal structure of the human ecto-5'-nucleotidase (CD73): insights into the regulation of purinergic signaling," Structure (2012) 20(12): 2161-2173.

Perrot et al., "Blocking Antibodies Targeting the CD39/CD73 Immunosuppressive Pathway Unleash Immune Responses in Combination Cancer Therapies," Cell Rep. (2019) 27(8):2411-2425.e9.

Terp et al., "Anti-human CD73 monoclonal antibody inhibits metastasis formation in human breast cancer by inducing clustering and internalization of CD73 expressed on the surface of cancer cells," J Immunol. (2013) 191 (8):4165-73.

\* cited by examiner

ANTI-CD73 ANTIBODIES AND COMPOSITIONS

CROSS-REFERENCE TO RELATED APPLICATION

This application claims priority from U.S. Provisional Patent Application 62/896,908, filed Sep. 6, 2019, whose disclosure is incorporated by reference herein in its entirety.

SEQUENCE LISTING

The instant application contains a Sequence Listing which has been submitted electronically in ASCII format and is hereby incorporated by reference in its entirety. The electronic copy of the Sequence Listing, created on Sep. 3, 2020, is named 022675_US055_SL.txt and is 30,355 bytes in size.

BACKGROUND OF THE INVENTION

Tumor cells are surrounded by a complex microenvironment (the tumor microenvironment, or TME) that influences each step of tumorigenesis. In the TME, increased concentrations of immune modulating factors such as adenosine help tumor cells overcome the host anti-tumor immune response.

Adenosine binds to four different receptors (ARs) expressed on various immune cells such as $CD4^+$ and $CD8^+$ T cells and natural killer (NK) cells. These purinergic G protein-coupled receptors, A1R, A2AR, A2BR, and A3R, each exhibit distinct properties and cell and tissue distribution. Binding of adenosine to ARs suppresses the anti-tumor responses of T cells and NK cells and also promotes development and activation of immunosuppressive cells such as regulatory T cells (Tregs) and myeloid-derived suppressor cells (MDSCs), thus facilitating cancer progression. In addition to the immunoregulatory action of adenosine receptors, their signaling may also directly impinge on cancer cell survival and proliferation.

The accumulation of adenosine in the TME is mediated by cell surface enzymes CD73 and CD39, which work in a pathway to convert extracellular ATP to adenosine. CD73, also known as 5'-NT, is an extracellular enzyme consisting of two 65 kD subunits joined by an alpha-helical linker into a homodimer. Overexpressed by many cancer cells, CD73 mediates the hydrolysis of 5'-AMP to adenosine, particularly under tumor hypoxic conditions. Studies have shown that high expression of CD73 leads to poorer prognosis in various cancers, such as triple negative breast cancer, lung cancer, ovarian cancer, kidney cancer, gastric cancer, and melanoma. Inhibition of CD73 may be a potent approach to cancer therapy.

SUMMARY OF THE INVENTION

The present disclosure is directed to novel recombinant antibodies targeting CD73, as well as pharmaceutical compositions comprising one or more of these antibodies, and use of the antibodies and pharmaceutical compositions for treatment of cancer. Compared to currently available treatments for such cancers, including antibody treatments, it is contemplated that the antibodies and compositions described herein may provide a superior clinical response either alone or in combination with another cancer therapeutic.

In some aspects, the present disclosure provides an anti-CD73 antibody or an antigen-binding portion thereof, wherein the antibody binds to the same epitope of human CD73 as an antibody comprising:
a) a heavy chain (HC) comprising the amino acid sequences of SEQ ID NOs: 9 and 41 and a light chain (LC) comprising the amino acid sequences of SEQ ID NOs: 13 and 42;
b) an HC comprising the amino acid sequences of SEQ ID NOs: 10 and 41 and an LC comprising the amino acid sequences of SEQ ID NOs: 14 and 42;
c) an HC comprising the amino acid sequences of SEQ ID NOs: 11 and 41 and an LC comprising the amino acid sequences of SEQ ID NOs: 15 and 42; or
d) an HC comprising the amino acid sequences of SEQ ID NOs: 12 and 41 and an LC comprising the amino acid sequences of SEQ ID NOs: 16 and 42.

In certain embodiments, the heavy chain of said antibody comprises:
i) heavy chain complementarity determining regions (H-CDR)-1-3 comprising the amino acid sequences of SEQ ID NOs: 17-19, respectively;
ii) a heavy chain variable domain (VH) comprising an amino acid sequence at least 90% identical to the amino acid sequence of SEQ ID NO: 9;
iii) a VH comprising the amino acid sequence of SEQ ID NO: 9; or
iv) a heavy chain (HC) comprising the amino acid sequences of SEQ ID NOs: 9 and 41;
and the light chain of said antibody comprises:
i) light chain complementarity determining regions (L-CDR)-1-3 comprising the amino acid sequences of SEQ ID NOs: 20-22, respectively;
ii) a light chain variable domain (VL) comprising an amino acid sequence at least 90% identical to the amino acid sequence of SEQ ID NO: 13;
iii) a VL comprising the amino acid sequence of SEQ ID NO: 13; or
iv) a light chain (LC) comprising the amino acid sequences of SEQ ID NOs: 13 and 42.

In certain embodiments, the heavy chain of said antibody comprises:
i) heavy chain complementarity determining regions (H-CDR)-1-3 comprising the amino acid sequences of SEQ ID NOs: 23-25, respectively;
ii) a heavy chain variable domain (VH) comprising an amino acid sequence at least 90% identical to the amino acid sequence of SEQ ID NO: 10;
iii) a VH comprising the amino acid sequence of SEQ ID NO: 10; or
iv) a heavy chain (HC) comprising the amino acid sequences of SEQ ID NOs: 10 and 41;
and the light chain of said antibody comprises:
i) light chain complementarity determining regions (L-CDR)-1-3 comprising the amino acid sequences of SEQ ID NOs: 26-28, respectively;
ii) a light chain variable domain (VL) comprising an amino acid sequence at least 90% identical to the amino acid sequence of SEQ ID NO: 14;
iii) a VL comprising the amino acid sequence of SEQ ID NO: 14; or
iv) a light chain (LC) comprising the amino acid sequences of SEQ ID NOs: 14 and 42.

In certain embodiments, the heavy chain of said antibody comprises:
i) heavy chain complementarity determining regions (H-CDR)-1-3 comprising the amino acid sequences of SEQ ID NOs: 29-31, respectively;

ii) a heavy chain variable domain (VH) comprising an amino acid sequence at least 90% identical to the amino acid sequence of SEQ ID NO: 11;
iii) a VH comprising the amino acid sequence of SEQ ID NO: 11; or
iv) a heavy chain (HC) comprising the amino acid sequences of SEQ ID NOs: 11 and 41;
and the light chain of said antibody comprises:
i) light chain complementarity determining regions (L-CDR)-1-3 comprising the amino acid sequences of SEQ ID NOs: 32-34, respectively;
ii) a light chain variable domain (VL) comprising an amino acid sequence at least 90% identical to the amino acid sequence of SEQ ID NO: 15;
iii) a VL comprising the amino acid sequence of SEQ ID NO: 15; or
iv) a light chain (LC) comprising the amino acid sequences of SEQ ID NOs: 15 and 42.

In certain embodiments, the heavy chain of said antibody comprises:
i) heavy chain complementarity determining regions (H-CDR)-1-3 comprising the amino acid sequences of SEQ ID NOs: 35-37, respectively;
ii) a heavy chain variable domain (VH) comprising an amino acid sequence at least 90% identical to the amino acid sequence of SEQ ID NO: 12;
iii) a VH comprising the amino acid sequence of SEQ ID NO: 12; or
iv) a heavy chain (HC) comprising the amino acid sequences of SEQ ID NOs: 12 and 41;
and the light chain of said antibody comprises:
i) light chain complementarity determining regions (L-CDR)-1-3 comprising the amino acid sequences of SEQ ID NOs: 38-40, respectively;
ii) a light chain variable domain (VL) comprising an amino acid sequence at least 90% identical to the amino acid sequence of SEQ ID NO: 16;
iii) a VL comprising the amino acid sequence of SEQ ID NO: 16; or
iv) a light chain (LC) comprising the amino acid sequences of SEQ ID NOs: 16 and 42.

In some embodiments, the present disclosure provides an anti-CD73 antibody or an antigen-binding portion thereof, wherein said antibody comprises the H-CDR1-3 and L-CDR1-3 amino acid sequences of:
a) SEQ ID NOs: 17-22, respectively;
b) SEQ ID NOs: 23-28, respectively;
c) SEQ ID NOs: 29-34, respectively; or
d) SEQ ID NOs: 35-40, respectively.

In some embodiments, the present disclosure provides an anti-CD73 antibody or an antigen-binding portion thereof, wherein said antibody comprises a heavy chain variable domain amino acid sequence and a light chain variable domain amino acid sequence that are at least 90% identical to the amino acid sequences of:
a) SEQ ID NOs: 9 and 13, respectively;
b) SEQ ID NOs: 10 and 14, respectively;
c) SEQ ID NOs: 11 and 15, respectively; or
d) SEQ ID NOs: 12 and 16, respectively.

In some embodiments, the present disclosure provides an anti-CD73 antibody or an antigen-binding portion thereof, wherein said antibody comprises a heavy chain variable domain and a light chain variable domain comprising the amino acid sequences of:
a) SEQ ID NOs: 9 and 13, respectively;
b) SEQ ID NOs: 10 and 14, respectively;
c) SEQ ID NOs: 11 and 15, respectively; or
d) SEQ ID NOs: 12 and 16, respectively.

In some embodiments, the present disclosure provides an anti-CD73 antibody that comprises:
a) a heavy chain (HC) comprising the amino acid sequences of SEQ ID NOs: 9 and 41 and a light chain (LC) comprising the amino acid sequences of SEQ ID NOs: 13 and 42;
b) an HC comprising the amino acid sequences of SEQ ID NOs: 10 and 41 and an LC comprising the amino acid sequences of SEQ ID NOs: 14 and 42;
c) an HC comprising the amino acid sequences of SEQ ID NOs: 11 and 41 and an LC comprising the amino acid sequences of SEQ ID NOs: 15 and 42; or
d) an HC comprising the amino acid sequences of SEQ ID NOs: 12 and 41 and an LC comprising the amino acid sequences of SEQ ID NOs: 16 and 42.

In some embodiments, the present disclosure provides an anti-CD73 antibody or antigen-binding portion thereof that binds to an epitope on human CD73 comprising:
a) amino acid residues R73, R109, and D168 of SEQ ID NO: 43;
b) amino acid residue R109 of SEQ ID NO: 43; or
c) amino acid residues I301, S302, and H304 of SEQ ID NO: 43.

In some embodiments, the present disclosure provides an anti-CD73 antibody or antigen-binding portion thereof that binds to an epitope on human CD73 comprising:
a) amino acid residues 27-31, 61-75, and 161-170 of SEQ ID NO: 43;
b) amino acid residues 61-70 and 161-170 of SEQ ID NO: 43; or
c) amino acid residues 27-31, 266-270, and 291-305 of SEQ ID NO: 43.

In certain embodiments, an anti-CD73 antibody or antigen-binding portion described herein has at least one property selected from:
a) inhibits the activity of soluble CD73 in vitro;
b) inhibits the activity of CD73 on Calu-6 cells in vitro;
c) inhibits the activity of CD73 on H292 cells in vitro;
d) specifically binds to human and cynomolgus CD73 expressed on CHO-S cells;
e) binds to the ECD of human CD73 with a $K_D$ of 1 nM or less as measured by SPR;
f) binds to the ECD of cynomolgus CD73 with a $K_D$ of 0.7 nM or less as measured by SPR;
g) does not bind to the same epitope of CD73 as oleclumab, CPX006, and/or 11E1;
h) binds an epitope on the CD73 homodimer in a manner that gives rise to a 1:1 complex;
i) inhibits soluble CD73 activity more effectively than oleclumab in vitro;
j) inhibits CD73 activity on Calu-6, H292, and Cynom-K1 cells in vitro;
k) inhibits CD73 activity on Calu-6, NCI-H1775, KYSE-30, and Capan-2 cells in vitro;
l) inhibits survival and/or proliferation of MDA-MB-231 and MDA-MB-468 cells in vitro;
m) inhibits CD73 activity on primary $CD4^+$ and $CD8^+$ T cells and $CD19^+$ B cells in vitro;
n) restores proliferation of $CD4^+$ T cells in vitro;
o) activates $CD4^+$ and $CD8^+$ T cells in vitro;
p) in combination with an anti-PD-1 antibody, restores T cell proliferation in a one-way mixed lymphocyte reaction (MLR) in the presence of AMP;
q) enhances T cell activation in the presence of AMP in combination with an anti-PD-1 antibody, in a one-way MLR;

r) does not stimulate B cell activation in vitro;
s) does not reduce levels of CD73 in H292 cells in vitro by more than 25%;
t) inhibits CD73 activity in tumors harvested from PBMC-humanized mice engrafted with A375 cells;
u) inhibits tumor growth in vivo in NOD-scid mice engrafted with MDA-MB-231 cells;
v) inhibits tumor growth in vivo in PBMC-humanized mice engrafted with Calu-6 cells; and
w) inhibits tumor growth in vivo in PBMC-humanized mice engrafted with A375 cells.

In particular embodiments, the antibody or antigen-binding portion has at least 1, 2, 3, 4, 5, 6, 7, 8, 9, 10, 11, 12, 13, 14, 15, 16, 17, 18, 19, 20, 21, 22, or all 23 of said properties.

In certain embodiments, an anti-CD73 antibody or antigen-binding portion described herein is an IgG, such as an $IgG_1$. The antibody may comprise at least one mutation in the Fc region. For example, the antibody may be an $IgG_1$ and comprise a mutation in one or more of heavy chain amino acid positions 234 and 235, which are numbered according to the IMGT® numbering scheme. In particular embodiments, one or both of the amino acid residues at positions 234 and 235 are mutated from Leu to Ala.

In some embodiments, the present disclosure provides a pharmaceutical composition comprising an anti-CD73 antibody or antigen-binding portion thereof described herein and a pharmaceutically acceptable excipient. In certain embodiments, the pharmaceutical composition may further comprise one or more of an immunostimulatory agent, a vaccine, a chemotherapeutic agent, an anti-neoplastic agent, an anti-angiogenic agent, a tyrosine kinase inhibitor, and a CD73 pathway inhibitor.

In some embodiments, the present disclosure provides an isolated nucleic acid molecule comprising a nucleotide sequence that encodes the heavy chain or an antigen-binding portion thereof, or a nucleotide sequence that encodes the light chain or an antigen-binding portion thereof, or both, of an anti-CD73 antibody or antigen-binding portion described herein. In certain embodiments, the nucleic acid molecule may comprise the nucleotide sequence of any one of SEQ ID NOs: 1-8.

In some embodiments, the present disclosure provides a vector comprising an isolated nucleic acid molecule described herein, wherein said vector further comprises an expression control sequence.

In some embodiments, the present disclosure provides a host cell comprising a nucleotide sequence that encodes the heavy chain or an antigen-binding portion thereof, and a nucleotide sequence that encodes the light chain or an antigen-binding portion thereof, of an anti-CD73 antibody or antigen-binding portion described herein.

In some embodiments, the present disclosure provides a method for producing an anti-CD73 antibody or an antigen-binding portion thereof, comprising providing a host cell described herein, culturing said host cell under conditions suitable for expression of the antibody or portion, and isolating the resulting antibody or portion.

In some embodiments, the present disclosure provides a bi-specific binding molecule comprising the antigen-binding portion of one or two distinct anti-CD73 antibodies described herein.

In some embodiments, the present disclosure provides a method for decreasing CD73 activity in a patient in need thereof, comprising administering to said patient a therapeutically effective amount of an anti-CD73 antibody or antigen-binding portion, pharmaceutical composition, or bi-specific binding molecule described herein.

In some embodiments, the present disclosure provides a method for increasing $CD4^+$ T cell proliferation in a patient in need thereof, comprising administering to said patient a therapeutically effective amount of an anti-CD73 antibody or antigen-binding portion, pharmaceutical composition, or bi-specific binding molecule described herein.

In some embodiments, the present disclosure provides a method for stimulating the immune system in a patient in need thereof, comprising administering to said patient a therapeutically effective amount of an anti-CD73 antibody or antigen-binding portion, pharmaceutical composition, or bi-specific binding molecule described herein.

In some embodiments, the present disclosure provides a method for treating cancer in a patient, comprising administering to said patient a therapeutically effective amount of an anti-CD73 antibody or antigen-binding portion, pharmaceutical composition, or bi-specific binding molecule described herein. In certain embodiments, the cancer originates in a tissue selected from the group consisting of skin, lung, intestine, colon, ovary, brain, prostate, kidney, soft tissues, the hematopoietic system, head and neck, liver, bone, bladder, breast, stomach, uterus, cervix, and pancreas. In certain embodiments, the cancer is melanoma, head and neck cancer, breast cancer, bladder cancer, non-small cell lung cancer, pancreatic cancer, ovarian cancer, renal cell carcinoma, prostate cancer, colorectal cancer, cholangiocarcinoma, thyroid cancer, or testicular cancer.

In certain embodiments, a treatment described herein further comprises administering to the patient an immunostimulatory agent, a vaccine, a chemotherapeutic agent, an anti-neoplastic agent, an anti-angiogenic agent, a tyrosine kinase inhibitor, a CD73 pathway inhibitor, or radiation therapy.

In some aspects, the present disclosure provides use of an anti-CD73 antibody or antigen-binding portion, pharmaceutical composition, or bi-specific binding molecule described herein for the manufacture of a medicament for:
a) decreasing CD73 activity in a patient;
b) increasing $CD4^+$ T cell proliferation in a patient;
c) stimulating the immune system in a patient; or
d) treating cancer in a patient.

In some aspects, the present disclosure provides an anti-CD73 antibody or antigen-binding portion, pharmaceutical composition, or bi-specific binding molecule described herein for use in:
a) decreasing CD73 activity in a patient;
b) increasing $CD4^+$ T cell proliferation in a patient;
c) stimulating the immune system in a patient; or
d) treating cancer in a patient.

Other features, objectives, and advantages of the invention are apparent in the detailed description that follows. It should be understood, however, that the detailed description, while indicating embodiments and aspects of the invention, is given by way of illustration only, not limitation. Various changes and modifications within the scope of the invention will become apparent to those skilled in the art from the detailed description.

BRIEF DESCRIPTION OF THE DRAWINGS

FIG. 17A is a series of plots showing the level of CD69 on B cells (CD20+).

FIG. 17B is a series of graphs showing mean fluorescence intensity (MFI) for antibody staining of B cell activation markers CD25, CD69 and CD83. The "IgG1-LALA Control" is a non-CD73-specific FcγR-deficient IgG1-LALA isotype antibody. Data are replicates from one donor and are presented as mean±SEM.

DETAILED DESCRIPTION OF THE INVENTION

Figure 1:
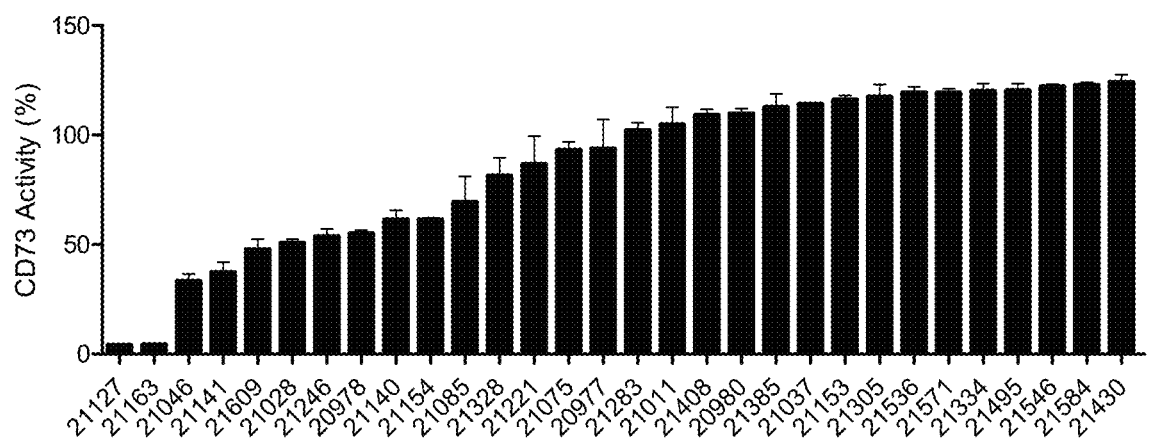
FIG. 1 is a graph showing the activity of soluble CD73 after treatment with the indicated anti-CD73 antibodies. Data are normalized to untreated controls and presented as mean±SEM.

The present disclosure provides new anti-human CD73 antibodies that can be used to suppress CD73 activity in a patient, such as a cancer patient. Unless otherwise stated, as used herein, "CD73" refers to human CD73. A human CD73 polypeptide sequence is available under UniProt Accession No. P21589 (5NTD_HUMAN) (SEQ ID NO: 43), as shown below:

```
         10         20         30         40
MCPRAARAPA TLLLALGAVL WPAAGAWELT ILHTNDVHSR 50         60         70         80
LEQTSEDSSK CVNASPCMGG VARLFTKVQQ IRRAEPNVLL 90        100        110        120
LDAGDQYQGT IWFTVYKGAE VAHFMNALRY DAMALGNHEF 130        140        150        160
DNGVEGLIEP LLKEAKFPIL SANIKAEGPL ASQISGLYLP 170        180        190        200
YKVLPVGDEV VGIVGYTSKE TPFLSNPGTN LVFEDEITAL 210        220        230        240
QPEVDKLKTL NVNKIIALGH SGFEMDKLIA QKVPGVDVVV 250        260        270        280
GGHSNTFLYT GNPPSKEVPA GKYPFIVTSD DGRKVPVVQA 290        300        310        320
YAFGKYLYGL KIEFDERGNV ISSHGNPILL NSSIPEDPSI 330        340        350        360
KADINKWRIK LDNYSTQELG KTIVYLDGSS QSCRFRECNM 370        380        390        400
GNLICDAMIN NNLRHTDEME WNHVSMCILN GGGIRSPIDE 410        420        430        440
RNNGTITWEN LAAVLPFGGT FDLVQLKGST LKKAIFEHSVH 450        460        470        480
RYGQSTGEFL QVGGIHVVYD LSRKPGDRVV KLDVLCTKCR 490        500        510        520
VPSYDPLKMD EVYKVILPNF LANGGDGGQM IKDELLRHDS 530        540        550        560
GDQDINVVST YISKMKVIYP AVEGRIKFST GSHCHGSFSL

570
IFLSLWAVIF VLYQ
```

The term "antibody" (Ab) or "immunoglobulin" (Ig), as used herein, refers to a tetramer comprising two heavy (H) chains (about 50-70 kDa) and two light (L) chains (about 25 kDa) inter-connected by disulfide bonds. Each heavy chain is comprised of a heavy chain variable domain (VH) and a heavy chain constant region (CH). Each light chain is composed of a light chain variable domain (VL) and a light chain constant region (CL). The VH and VL domains can be subdivided further into regions of hypervariability, termed "complementarity determining regions" (CDRs), interspersed with regions that are more conserved, termed "framework regions" (FRs). Each VH and VL is composed of three CDRs (H-CDR herein designates a CDR from the heavy chain; and L-CDR herein designates a CDR from the light chain) and four FRs, arranged from amino-terminus to carboxyl-terminus in the following order: FR1, CDR1, FR2, CDR2, FR3, CDR3, FR4. The assignment of amino acid numbers, and of FR and CDR regions, in the heavy or light chain may be in accordance with IMGT® definitions (EU numbering; Lefranc et al., Dev Comp Immunol 27(1):55-77 (2003)); or the definitions of Kabat, Sequences of Proteins of Immunological Interest (National Institutes of Health, Bethesda, Md. (1987 and 1991)); Chothia & Lesk, J. Mol. Biol. 196:901-917 (1987); Chothia et al., Nature 342:878-883 (1989); MacCallum et al., J. Mol. Biol. 262:732-745 (1996); or Honegger and Plückthun, J. Mol. Biol. 309(3): 657-70 (2001).

The term "recombinant antibody" refers to an antibody that is expressed from a cell or cell line comprising the nucleotide sequence(s) that encode the antibody, wherein said nucleotide sequence(s) are not naturally associated with the cell.

The term "isolated protein," "isolated polypeptide" or "isolated antibody" refers to a protein, polypeptide or antibody that by virtue of its origin or source of derivation (1) is not associated with naturally associated components that accompany it in its native state, (2) is free of other proteins from the same species, (3) is expressed by a cell from a different species, and/or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "affinity" refers to a measure of the attraction between an antigen and an antibody. The intrinsic attractiveness of the antibody for the antigen is typically expressed as the binding affinity equilibrium constant ($K_D$) of a particular antibody-antigen interaction. An antibody is said to specifically bind to an antigen when the $K_D$ is 1 mM, preferably 100 nM. A $K_D$ binding affinity constant can be measured, e.g., by surface plasmon resonance (BIAcore™) or Bio-Layer Interferometry, for example using the IBIS MX96 SPR system from IBIS Technologies or the Octet™ system from ForteBio.

The term "epitope" as used herein refers to a portion (determinant) of an antigen that specifically binds to an antibody or a related molecule such as a bi-specific binding molecule. Epitopic determinants generally consist of chemically active surface groupings of molecules such as amino acids or carbohydrate or sugar side chains and generally have specific three-dimensional structural characteristics, as well as specific charge characteristics. An epitope may be "linear" or "conformational." In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope on an antigen is determined, it is possible to generate antibodies to that epitope using techniques well known in the art. For example, an antibody to a linear epitope may be generated, e.g., by immunizing an animal with a peptide having the amino acid residues of the linear epitope. An antibody to a conformational epitope may be generated, e.g., by immunizing an animal with a mini-domain containing the relevant amino acid residues of the conformational epitope. An antibody to a particular epitope can also be generated, e.g., by immunizing an animal with the target molecule of interest (e.g., CD73) or a relevant portion thereof, then screening for binding to the epitope.

One can determine whether an antibody binds to the same epitope as or competes for binding with an anti-CD73 antibody of the present disclosure by using methods known in the art, including, without limitation, competition assays, epitope binning, and alanine scanning. In some embodiments, one allows the anti-CD73 antibody of the present disclosure to bind to CD73 under saturating conditions, and then measures the ability of the test antibody to bind to CD73. If the test antibody is able to bind to CD73 at the same time as the reference anti-CD73 antibody, then the test antibody binds to a different epitope than the reference anti-CD73 antibody. However, if the test antibody is not able to bind to CD73 at the same time, then the test antibody binds to the same epitope, an overlapping epitope, or an epitope that is in close proximity to the epitope bound by the anti-CD73 antibody of the present disclosure. This experiment can be performed using, e.g., ELISA, RIA, BIA-CORE™ SPR, Bio-Layer Interferometry or flow cytometry. To test whether an anti-CD73 antibody cross-competes with another anti-CD73 antibody, one may use the competition method described above in two directions, i.e., determining if the known antibody blocks the test antibody and vice versa. Such cross-competition experiments may be performed, e.g., using an IBIS MX96 SPR instrument or the Octet™ system.

The term "human antibody" refers to an antibody in which the variable domain and constant region sequences are derived from human sequences. The term encompasses antibodies with sequences that are derived from human genes but have been modified, e.g., to decrease immunogenicity, increase affinity, and/or increase stability. Further, the term encompasses antibodies produced recombinantly in nonhuman cells, which may impart glycosylation not typical of human cells. The term also encompasses antibodies produced in transgenic nonhuman organisms with human antibody genes (e.g., OmniRat® rats).

The term "antigen-binding portion" of an antibody (or simply "antibody portion"), as used herein, refers to one or more portions or fragments of an antibody that retain the ability to specifically bind to an antigen (e.g., human CD73, or a portion thereof). It has been shown that certain fragments of a full-length antibody can perform the antigen-binding function of the antibody. Examples of binding fragments encompassed within the term "antigen-binding portion" include (i) a Fab fragment: a monovalent fragment consisting of the VL, VH, CL and CH1 domains; (ii) a F(ab')2 fragment: a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which consists of a VH domain; and (vi) an isolated complementarity determining region (CDR) capable of specifically binding to an antigen. Furthermore, although the two domains of the Fv fragment, VL and VH, are encoded by separate genes, they can be joined, using recombinant methods, by a synthetic linker that enables them to be made as a single protein chain in which the VL and VH domains pair to form monovalent molecules (known as single chain Fv (scFv)). Also within the present disclosure are antigen-binding molecules comprising a VH and/or a VL. In the case of a VH, the molecule may also comprise one or more of a CH1, hinge, CH2, or CH3 region. Such single chain antibodies are also intended to be encompassed within the term "antigen-binding portion" of an antibody. Other forms of single chain antibodies, such as diabodies, are also encompassed. Diabodies are bivalent, bi-specific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites.

Antibody portions, such as Fab and F(ab')$_2$ fragments, can be prepared from whole antibodies using conventional techniques, such as papain or pepsin digestion of whole antibodies. Moreover, antibodies, antibody portions and immunoadhesion molecules can be obtained using standard recombinant DNA techniques, e.g., as described herein.

The class (isotype) and subclass of anti-CD73 antibodies may be determined by any method known in the art. In general, the class and subclass of an antibody may be determined using antibodies that are specific for a particular class and subclass of antibody. Such antibodies are available commercially. The class and subclass can be determined by ELISA or Western blot as well as other techniques. Alternatively, the class and subclass may be determined by sequencing all or a portion of the constant region of the heavy and/or light chains of the antibodies, comparing their amino acid sequences to the known amino acid sequences of various classes and subclasses of immunoglobulins, and determining the class and subclass of the antibodies.

Unless otherwise indicated, all antibody amino acid residue numbers referred to in this disclosure are those under the IMGT® numbering scheme (EU numbering).

Anti-CD73 Antibodies

The present disclosure provides antibodies directed against CD73, and antigen-binding portions thereof. In a particular embodiment, the antibodies disclosed herein are human antibodies generated from transgenic animals (e.g., rats) that are able to produce antibodies encoded by rearranged human antibody genes. In certain embodiments, the human antibodies may contain certain mutations, e.g., to change primer-derived mutations back to the germline sequence (see, e.g., the "Symplex-corrected" variant sequences in Table 1).

In some embodiments, the anti-CD73 antibodies of the present disclosure have the "LALA" mutations (L234A/L235A) in the Fc region. These mutations attenuate the antibodies' binding to human FcγR (Fc gamma receptors). Such antibodies are advantageous because they have a low level of secondary effector functions and do not deplete effector T cells or target other non-malignant cells.

In some embodiments, the anti-CD73 antibody or antigen-binding portion competes or cross-competes for binding to human CD73 with, or binds to the same epitope of human CD73 as, an antibody comprising:

a) an HC with the amino acid sequences of SEQ ID NOs: 9 and 41 and an LC with the amino acid sequences of SEQ ID NOs: 13 and 42;

b) an HC with the amino acid sequences of SEQ ID NOs: 10 and 41 and an LC with the amino acid sequences of SEQ ID NOs: 14 and 42;

c) an HC with the amino acid sequences of SEQ ID NOs: 11 and 41 and an LC with the amino acid sequences of SEQ ID NOs: 15 and 42; or d) an HC with the amino acid sequences of SEQ ID NOs: 12 and 41 and an LC with the amino acid sequences of SEQ ID NOs: 16 and 42.

In some embodiments, the anti-CD73 antibody or antigen-binding portion has a heavy chain CDR3 (H-CDR3) amino acid sequence of SEQ ID NO: 19, 25, 31, or 37.

In some embodiments, the anti-CD73 antibody or antigen-binding portion has heavy chain CDR1-3 (H-CDR1-3) comprising the amino acid sequences of SEQ ID NOs: 17-19, 23-25, 29-31, or 35-37, respectively.

In some embodiments, the anti-CD73 antibody or antigen-binding portion has a heavy chain variable domain (VH) amino acid sequence that is at least 90%, 92%, 95%, 96%, 97%, 98%, or 99% identical to the amino acid sequence of any one of SEQ ID NOs: 9-12.

In some embodiments, the anti-CD73 antibody or antigen-binding portion has a VH comprising the amino acid sequence of any one of SEQ ID NOs: 9-12.

In some embodiments, the anti-CD73 antibody has a VH amino acid sequence that is at least 90%, 92%, 95%, 96%, 97%, 98%, or 99% identical to the amino acid sequence of any one of SEQ ID NOs: 9-12; and a heavy chain constant region amino acid sequence that is at least 90%, 92%, 95%, 96%, 97%, 98%, or 99% identical to the amino acid sequence of SEQ ID NO: 41.

In some embodiments, the anti-CD73 antibody comprises a VH amino acid sequence of any one of SEQ ID NOs: 9-12 and a heavy chain constant region amino acid sequence of SEQ ID NO: 41.

In some embodiments, the anti-CD73 antibody or antigen-binding portion has a light chain CDR3 (L-CDR3) amino acid sequence of SEQ ID NO: 22, 28, 34, or 40.

In some embodiments, the anti-CD73 antibody or antigen-binding portion has light chain CDR1-3 (L-CDR1-3) comprising the amino acid sequences of SEQ ID NOs: 20-22, 26-28, 32-34, or 38-40, respectively.

In some embodiments, the anti-CD73 antibody or antigen-binding portion has a light chain variable domain (VL) amino acid sequence that is at least 90%, 92%, 95%, 96%, 97%, 98%, or 99% identical to the amino acid sequence of any one of SEQ ID NOs: 13-16.

In some embodiments, the anti-CD73 antibody or antigen-binding portion has a VL comprising the amino acid sequence of any one of SEQ ID NOs: 13-16.

In some embodiments, the anti-CD73 antibody has a VL amino acid sequence that is at least 90%, 92%, 95%, 96%, 97%, 98%, or 99% identical to the amino acid sequence of any one of SEQ ID NOs: 13-16; and a light chain constant region amino acid sequence that is at least 90%, 92%, 95%, 96%, 97%, 98%, or 99% identical to the amino acid sequence of SEQ ID NO: 42.

In some embodiments, the anti-CD73 antibody comprises a VL amino acid sequence of any one of SEQ ID NOs: 13-16 and a light chain constant region amino acid sequence of SEQ ID NO: 42.

In certain embodiments, the anti-CD73 antibody comprises any one of the above-described heavy chains and any one of the above-described light chains.

In some embodiments, the anti-CD73 antibody or antigen-binding portion of the present disclosure comprises the H-CDR1-3 and L-CDR1-3 amino acid sequences of:
a) SEQ ID NOs: 17-22, respectively;
b) SEQ ID NOs: 23-28, respectively;
c) SEQ ID NOs: 29-34, respectively; or
d) SEQ ID NOs: 35-40, respectively.

In some embodiments, the anti-CD73 antibody or antigen-binding portion of the present disclosure comprises a VH and a VL that are 80%, 85%, 90%, 91%, 92%, 93%, 94%, 95%, 96%, 97%, 98%, or 99% identical to the amino acid sequences of:
a) SEQ ID NOs: 9 and 13, respectively;
b) SEQ ID NOs: 10 and 14, respectively;
c) SEQ ID NOs: 11 and 15, respectively; or
d) SEQ ID NOs: 12 and 16, respectively.

In some embodiments, the anti-CD73 antibody or antigen-binding portion of the present disclosure comprises a VH and a VL that comprise the amino acid sequences of:
a) SEQ ID NOs: 9 and 13, respectively;
b) SEQ ID NOs: 10 and 14, respectively;
c) SEQ ID NOs: 11 and 15, respectively; or
d) SEQ ID NOs: 12 and 16, respectively.

In some embodiments, the anti-CD73 antibody of the present disclosure comprises:
a) an HC with the amino acid sequences of SEQ ID NOs: 9 and 41 and an LC with the amino acid sequences of SEQ ID NOs: 13 and 42;
b) an HC with the amino acid sequences of SEQ ID NOs: 10 and 41 and an LC with the amino acid sequences of SEQ ID NOs: 14 and 42;
c) an HC with the amino acid sequences of SEQ ID NOs: 11 and 41 and an LC with the amino acid sequences of SEQ ID NOs: 15 and 42; or
d) an HC with the amino acid sequences of SEQ ID NOs: 12 and 41 and an LC with the amino acid sequences of SEQ ID NOs: 16 and 42.

The present disclosure also provides an anti-CD73 antibody or an antigen-binding portion thereof that competes or cross-competes for binding with, or binds to the same epitope as, antibody 21028, 21046, 21127, or 21163.

In some embodiments, the anti-CD73 antibody or antigen-binding portion of the present disclosure comprises the H-CDR1-3 and L-CDR1-3 amino acid sequences of antibody 21028, 21046, 21127, or 21163.

In some embodiments, the anti-CD73 antibody or antigen-binding portion of the present disclosure comprises a VH and VL that are at least 90% identical in amino acid sequence to the VH and VL, respectively, of antibody 21028, 21046, 21127, or 21163.

In some embodiments, the anti-CD73 antibody or antigen-binding portion of the present disclosure comprises a VH and VL that are the VH and VL, respectively, of antibody 21028, 21046, 21127, or 21163.

In some embodiments, the anti-CD73 antibody of the present disclosure is antibody 21028, 21046, 21127, or 21163, or an antibody with the same amino acid sequences as said antibody.

The class of an anti-CD73 antibody obtained by the methods described herein may be changed or switched with another class or subclass. In some embodiments of the present disclosure, a nucleic acid molecule encoding VL or VH is isolated using methods well known in the art such that it does not include nucleic acid sequences encoding CL or CH, respectively. The nucleic acid molecules encoding VL or VH then are operatively linked to a nucleic acid sequence encoding a CL or CH, respectively, from a different class of immunoglobulin molecule. This may be achieved using a vector or nucleic acid molecule that comprises a CL or CH sequence, as described above. For example, an anti-CD73 antibody that was originally IgM may be class switched to IgG. Further, the class switching may be used to convert one IgG subclass to another, e.g., from $IgG_1$ to $IgG_2$. A κ light chain constant region can be changed, e.g., to a λ light chain constant region, or vice-versa. An exemplary method for producing an antibody of the present disclosure with a desired Ig isotype comprises the steps of isolating a nucleic acid molecule encoding the heavy chain of an anti-CD73 antibody and a nucleic acid molecule encoding the light chain of an anti-CD73 antibody, obtaining the variable domain of the heavy chain, ligating a coding sequence for the variable domain of the heavy chain with a coding sequence for the constant region of a heavy chain of the desired isotype, expressing the light chain and the heavy chain encoded by the ligated sequence in a cell, and collecting the anti-CD73 antibody with the desired isotype.

The anti-CD73 antibody of the present disclosure can be an IgG, an IgM, an IgE, an IgA, or an IgD molecule, but is typically of the IgG isotype, e.g., of IgG subclass $IgG_1$, $IgG_2a$ or $IgG_2b$, $IgG_3$ or $IgG_4$. In some embodiments, the antibody is of the isotype subclass $IgG_1$. In some embodiments, the antibody is of the isotype subclass IgG2.

In some embodiments, the anti-CD73 antibody may comprise at least one mutation in the Fc region. A number of different Fc mutations are known, where these mutations alter the antibody's effector function. For example, in many cases it will be desirable to reduce or eliminate effector function, e.g., where ligand/receptor interactions are undesired or in the case of antibody-drug conjugates.

In some embodiments, the anti-CD73 antibody comprises at least one mutation in the Fc region that reduces effector function, e.g., mutations at one or more of positions 228, 233, 234 and 235, where amino acid positions are numbered according to the IMGT® numbering scheme.

In some embodiments, e.g., where the antibody is of the $IgG_1$ subclass, one or both of the amino acid residues at positions 234 and 235 may be mutated, for example from Leu to Ala (L234A/L235A). These mutations reduce effector function of the Fc region of $IgG_1$ antibodies. The amino acid positions are numbered according to the IMGT® numbering scheme.

In some embodiments, e.g., where the antibody is of the $IgG_4$ subclass, it may comprise the mutation S228P, where the amino acid position is numbered according to the IMGT® numbering scheme. This mutation is known to reduce undesired Fab arm exchange.

In some embodiments, an anti-CD73 antibody of the invention, or an antigen-binding portion thereof, binds to an epitope of CD73 that includes at least one (e.g., at least one, at least two, at least three, at least four, or at least five) of the following residues of SEQ ID NO: 43: R73, R109, D168, I301, S302, and H304. In certain embodiments, the antibody or antigen-binding portion binds to an epitope of CD73 that comprises or consists of residues R73, R109, and D168 (such as antibody 21127). In certain embodiments, the antibody or antigen-binding portion binds to an epitope of CD73 that comprises or consists of residue R109 (such as antibody 21163). In certain embodiments, the antibody or antigen-binding portion binds to an epitope of CD73 that comprises or consists of residues I301, S302, and H304 (such as antibody 21046).

In some embodiments, an anti-CD73 antibody of the invention, or an antigen-binding portion thereof, binds to an epitope of CD73 that comprises residues 27-31, 61-70, 61-75, 161-170, 266-270, and/or 291-305 of SEQ ID NO: 43. In certain embodiments, the antibody or antigen-binding portion binds to an epitope of CD73 that comprises or consists of residues 27-31, 61-75, and 161-170 (such as antibody 21127). In certain embodiments, the antibody or antigen-binding portion binds to an epitope of CD73 that comprises or consists of residues 61-70 and 161-170 (such as antibody 21163). In certain embodiments, the antibody or antigen-binding portion binds to an epitope of CD73 that comprises or consists of residues 27-31, 266-270, and 291-305 (such as antibody 21046).

In some embodiments, the antibody or portion binds to an epitope comprising residues 27-31 (or a fragment thereof, such as a 1, 2, 3, or 4 residue fragment), of SEQ ID NO: 43 (such as antibodies 21127 and 21046). In some embodiments, the antibody or portion binds to an epitope comprising residues 61-75 (or a fragment thereof, such as a 1, 2, 3, 4, 5, 6, 7, 8, 9, 10, 11, 12, 13, or 14 residue fragment, e.g., residues 61-70) of SEQ ID NO: 43 (such as antibodies 21127 and 21163). In some embodiments, the antibody or portion binds to an epitope comprising residues 161-170 (or a fragment thereof, such as a 1, 2, 3, 4, 5, 6, 7, 8, or 9 residue fragment) of SEQ ID NO: 43 (such as antibodies 21127 and 21163). In some embodiments, the antibody or portion binds to an epitope comprising residues 266-270 (or a fragment thereof, such as a 1, 2, 3, or 4 residue fragment) of SEQ ID NO: 43 (such as antibody 21046). In some embodiments, the antibody or portion binds to an epitope comprising residues 291-305 (or a fragment thereof, such as a 1, 2, 3, 4, 5, 6, 7, 8, 9, 10, 11, 12, 13, or 14 residue fragment) of SEQ ID NO: 43 (such as antibody 21046).

An epitope with any combination of the above residues, or the residues shown in Table 9, is also contemplated.

In some embodiments, an amino acid sequence comprising a CD73 epitope as described herein can be used as an immunogen (e.g., administered to an animal or as an antigen for screening antibody libraries) to generate or identify anti-CD73 antibodies or antigen-binding portions thereof that bind to said epitope.

In some embodiments (e.g., at a concentration of 10 µg/mL), an anti-CD73 antibody or antigen-binding portion described herein inhibits the activity of soluble CD73 by at least 40%, 50%, 60%, 70%, 80%, 90%, or 100% (e.g., by at least 40%). In some embodiments, at a concentration of 1, 2, 3, 4, 5, 7, 10, 15, 20, 30, 40, 50, or 100 µg/mL, an anti-CD73 antibody or antigen-binding portion described herein inhibits the activity of soluble CD73 by at least 90%.

In some embodiments (e.g., at a concentration of 10 µg/mL), an anti-CD73 antibody or antigen-binding portion described herein inhibits the activity of CD73 on Calu-6 cells by at least 70%, 75%, 80%, 85%, 90%, 95%, or 100% (e.g., by at least 75%).

In some embodiments (e.g., at a concentration of 10 µg/mL), an anti-CD73 antibody or antigen-binding portion described herein inhibits the activity of CD73 on H292 cells by at least 70%, 75%, 80%, 85%, 90%, 95%, or 100% (e.g., by at least 80%).

In some embodiments, an anti-CD73 antibody or antigen-binding portion described herein specifically binds to human CD73, cynomolgus CD73, or both, expressed on CHO-S cells.

In some embodiments, an anti-CD73 antibody or antigen-binding portion described herein binds to the extracellular domain (ECD) of human CD73 with a $K_D$ of 1, 0.9, 0.8, 0.7, 0.6, 0.5, 0.4, 0.3, 0.2, 0.1, 0.09, 0.08, 0.07, 0.06, 0.05, 0.04, 0.03, 0.02, or 0.01 nM or less (e.g., 1 nM or less) as measured by surface plasmon resonance (SPR).

In some embodiments, an anti-CD73 antibody or antigen-binding portion described herein binds to the extracellular domain (ECD) of cynomolgus CD73 with a $K_D$ of 1, 0.9, 0.8, 0.7, 0.6, 0.5, 0.4, 0.3, 0.2, 0.1, 0.09, 0.08, 0.07, 0.06, 0.05, 0.04, 0.03, 0.02, or 0.01 nM or less (e.g., 0.7 nM or less) as measured by surface plasmon resonance (SPR).

In some embodiments, an anti-CD73 antibody or antigen-binding portion described herein does not bind to the same epitope of CD73 as oleclumab, CPX006, 11E1, or any combination thereof.

In some embodiments, an anti-CD73 antibody or antigen-binding portion described herein binds an epitope on the CD73 homodimer in a manner that gives rise to a 1:1 complex. In certain embodiments, the antibody/CD73 binding gives rise only to a 1:1 complex. In certain embodiments, the antibody/CD73 binding gives rise mostly to a 1:1 complex. In particular embodiments, the binding of the antibody or antigen-binding portion to CD73 gives rise to a 1:1 complex independent of CD73 concentration.

In some embodiments, e.g., at a concentration of 1, 3, 5, 10, 20, 30, 40, 50, 60, 70, 80, 90, or 100 µg/mL or less (such as at a concentration of 10 µg/mL or less), an anti-CD73 antibody or antigen-binding portion described herein inhibits soluble CD73 activity. In certain embodiments (e.g., at a concentration of 10 µg/mL), the anti-CD73 antibody or antigen-binding portion inhibits said CD73 activity more effectively than oleclumab. In particular embodiments (e.g., with the antibody or antigen-binding portion at one of the above-listed concentrations), CD73 activity is inhibited by at least 10, 20, 30, 40, 50, 60, 70, 80, 90, or 100%. For example, the antibody or antigen-binding portion may inhibit CD73 activity by 100% at a concentration of 3 µg/mL.

In some embodiments, e.g., at a concentration of 1, 2, 3, 4, 5, 6, 7, 8, 9, 10, 15, 20, 25, 30, 40, 50, 75, or 100 µg/mL or less (such as at a concentration of 3 µg/mL or less), an anti-CD73 antibody or antigen-binding portion described herein inhibits CD73 activity on Calu-6, H292, Cynom-K1 cells, or any combination thereof. In certain embodiments, the anti-CD73 antibody or antigen-binding portion inhibits said CD73 activity more effectively than oleclumab. In certain embodiments, the anti-CD73 antibody or antigen-binding portion remains more effective than oleclumab after additional incubation of 3, 6, or 24 hours. In particular embodiments (e.g., with the antibody or antigen-binding portion at one of the above-listed concentrations), CD73 activity is inhibited by at least 10, 20, 30, 40, 50, 60, 70, 80, 90, or 100%.

In some embodiments (e.g., at a concentration of 25 µg/mL), an anti-CD73 antibody or antigen-binding portion described herein inhibits CD73 activity on any cell line or combination of cell lines shown in Table 11. In certain embodiments, the anti-CD73 antibody or antigen-binding portion inhibits CD73 activity on Calu-6, NCI-H1775 cells, KYSE-30 cells, Capan-2 cells, or any combination thereof. In certain embodiments, the anti-CD73 antibody or antigen-binding portion inhibits said CD73 activity more effectively than oleclumab.

In some embodiments, e.g., at a concentration of 0.01, 0.05, 0.1, 0.5, 1, 5, 10, 15, 20, or 25 µg/mL or less (such as at a concentration of 0.01 µg/mL or less), an anti-CD73 antibody or antigen-binding portion described herein inhibits survival and/or proliferation of MDA-MB-231 cells, MDA-MB-468 cells, or both, in vitro. In certain embodiments (e.g., at a concentration of 0.5 µg/mL or more), the anti-CD73 antibody or antigen-binding portion inhibits said survival/proliferation more effectively than oleclumab. In particular embodiments (e.g., with the antibody or antigen-binding portion at one of the above-listed concentrations), the number of viable cells is decreased by at least 10, 20, 30, 40, 50, 60, 70, 80, 90, or 100%.

In some embodiments, e.g., at a concentration of 0.01, 0.05, 0.1, 0.5, 1, 5, 10, 15, 20, or 25 µg/mL or less (such as at a concentration of 0.1 µg/mL or less), an anti-CD73 antibody or antigen-binding portion described herein inhibits its CD73 activity on primary CD4$^+$ cells, CD8$^+$ T cells, CD19$^+$ B cells, or any combination thereof. In particular embodiments (e.g., with the antibody or antigen-binding portion at one of the above-listed concentrations), CD73 activity is inhibited, e.g., by at least 10, 20, 30, 40, 50, 60, 70, 80, 90, or 100%.

In some embodiments, e.g., at a concentration of 0.05, 0.1, 0.5, or 1 µg/mL or less (such as at a concentration of 0.01 µg/mL or less), an anti-CD73 antibody or antigen-binding portion described herein restores proliferation of CD4$^+$ T cells. In some embodiments, e.g., at a concentration of 0.1, 0.5, 1, 10, 15, 20, 25, 30, 40, 50, or 100 µg/mL or less (such as at a concentration of 25 µg/mL or less), an anti-CD73 antibody or antigen-binding portion described herein restores proliferation of CD4$^+$ T cells to 100%. In some embodiments (e.g., at a concentration of 0.1 µg/mL or more), the anti-CD73 antibody or antigen-binding portion restores proliferation of CD4$^+$ T cells more effectively than oleclumab. In certain embodiments (e.g., with the antibody or antigen-binding portion at one of the above-listed concentrations), T cell proliferation is restored to at least 10, 20, 30, 40, 50, 60, 70, 80, 90, or 100%.

In some embodiments, e.g., at a concentration of 0.001, 0.005, 0.01, 0.05, 1, 5, 10, 15, or 25 µg/mL or less (such as at a concentration of 1 µg/mL or less), an anti-CD73 antibody or antigen-binding portion described herein activates CD4$^+$ and CD8$^+$ T cells. In some embodiments (e.g., at a concentration of 0.1 µg/mL or more), the anti-CD73 antibody or antigen-binding portion activates CD4$^+$ and CD8$^+$ T cells more effectively than oleclumab.

In some embodiments, e.g., at a concentration of 0.01, 0.05, 0.1, 0.5, 1, 5, or 10 µg/mL or less (such as at a concentration of 0.01 µg/mL or less), an anti-CD73 antibody or antigen-binding portion described herein, in combination with an anti-PD-1 antibody, restores T cell proliferation in the presence of AMP in a one-way mixed lymphocyte reaction (MLR). In certain embodiments (e.g., at a concentration of 1 µg/mL or less), the anti-CD73 antibody or antigen-binding portion, in combination with the anti-PD-1 antibody, fully restores T cell proliferation. In certain embodiments (e.g., at a concentration of 0.1 µg/mL or more), the anti-CD73 antibody or antigen-binding portion, in combination with the anti-PD-1 antibody, restores T cell proliferation more effectively than oleclumab. In particular embodiments (e.g., with the antibody or antigen-binding portion at one of the above-listed concentrations, in combination with an anti-PD-1 antibody), T cell proliferation is restored to at least 10, 20, 30, 40, 50, 60, 70, 80, 90, or 100%.

In some embodiments, e.g., at a concentration of 0.5, 1, 5, 10, 15, or 25 µg/mL or less (such as at a concentration of 1 µg/mL or less), an anti-CD73 antibody or antigen-binding portion described herein enhances T cell activation in the presence of AMP, in a one-way MLR. In some embodiments, the anti-CD73 antibody or antigen-binding portion, in combination with an anti-PD-1 antibody (such as 12819), enhances T cell activation in the presence of AMP in a one-way MLR.

In some embodiments (e.g., at a concentration of 10 µg/mL), an anti-CD73 antibody or antigen-binding portion described herein does not stimulate B cell activation in vitro. In some embodiments (e.g., at a concentration of 10 µg/mL), an anti-CD73 antibody or antigen-binding portion described herein stimulates B cell activation in vitro. B cell activation may be determined by looking at markers such as, for example, CD25, CD69, and/or CD83.

In some embodiments (e.g., at a concentration of 25 µg/mL), an anti-CD73 antibody or antigen-binding portion described herein does not reduce levels of CD73 in H292 cells in vitro. In some embodiments (e.g., at a concentration of 25 µg/mL), an anti-CD73 antibody or antigen-binding portion described herein reduces levels of CD73 in H292 cells in vitro, e.g., to no more than 40%, 50%, 60%, 70%, 80%, or 90% as compared to an untreated control. In some embodiments (e.g., at a concentration of 25 µg/mL), an anti-CD73 antibody or antigen-binding portion described herein only modestly reduces levels of CD73 in H292 cells in vitro. For example, in certain embodiments, the levels of CD73 are reduced by no more than, e.g., 5%, 10%, 15%, 20%, 25%, 30%, or 35% (e.g., 25%).

In some embodiments, an anti-CD73 antibody or antigen-binding portion described herein inhibits CD73 activity in tumors harvested from PBMC-humanized mice engrafted with A375 cells (e.g., where the mice are dosed with the antibody or antigen-binding portion at 5 mg/kg, 20 mg/kg, or 50 mg/kg three times weekly for one or two weeks). In certain embodiments, the inhibition of CD73 activity is maintained for at least 20, 24, 28, 32, 36, 40, 44, 50, 75, 100, 125, 150, 175, or 200 days (e.g., at least 28 days) after treatment has ended.

In some embodiments, an anti-CD73 antibody or antigen-binding portion described herein inhibits tumor growth in NOD-scid mice engrafted with MDA-MB-231 cells (e.g., where the mice are dosed with the antibody or antigen-binding portion at 10 mg/kg twice weekly for a total of 16 treatments). In certain embodiments, the tumor growth inhibition is maintained with limited gain in tumor volume (e.g., less than 10, 20, 30, 40, or 50 mm$^3$) for at least 10, 20, 30, 40, 50, 60, 70, 80, 90, 100, 120, 140, 160, 180, or 200 days (e.g., at least 60 days) after treatment has ended.

In some embodiments, an anti-CD73 antibody or antigen-binding portion described herein inhibits tumor growth in PBMC-humanized mice engrafted with Calu-6 or A375 cells (e.g., where the mice are dosed with the antibody or antigen-binding portion at 10 mg/kg three times weekly for a total of six treatments).

The present disclosure also contemplates an anti-CD73 antibody or antigen-binding portion with any combination of the above properties.

In some embodiments, an anti-CD73 antibody or antigen-binding portion described herein has at least one (e.g., 1, 2, 3, 4, 5, 6, 7, 8, 9, 10, 11, 12, 13, 14, 15, 16, 17, 18, 19, 20, 21, 22, or all 23) of the following properties:
a) inhibits the activity of soluble CD73 in vitro;
b) inhibits the activity of CD73 on Calu-6 cells in vitro;
c) inhibits the activity of CD73 on H292 cells in vitro;
d) specifically binds to human and cynomolgus CD73 expressed on CHO-S cells;
e) binds to the ECD of human CD73 with a $K_D$ of 1 nM or less as measured by SPR;
f) binds to the ECD of cynomolgus CD73 with a $K_D$ of 0.7 nM or less as measured by SPR;
g) does not bind to the same epitope of CD73 as oleclumab, CPX006, and/or 11E1,
h) binds an epitope on the CD73 homodimer in a manner that gives rise to a 1:1 complex;
i) inhibits soluble CD73 activity more effectively than oleclumab in vitro;
j) inhibits CD73 activity on Calu-6, H292, and Cynom-K1 cells in vitro;
k) inhibits CD73 activity on Calu-6, NCI-H1775, KYSE-30, and Capan-2 cells in vitro;
l) inhibits survival and/or proliferation of MDA-MB-231 and MDA-MB-468 cells in vitro;
m) inhibits CD73 activity on primary CD4$^+$ and CD8$^+$ T cells and CD19$^+$ B cells in vitro;
n) restores proliferation of CD4$^+$ T cells in vitro;
o) activates CD4$^+$ and CD8$^+$ T cells in vitro;
p) in combination with an anti-PD-1 antibody, restores T cell proliferation in a one-way mixed lymphocyte reaction (MLR) in the presence of AMP;
q) enhances T cell activation in the presence of AMP in combination with an anti-PD-1 antibody, in a one-way MLR;
r) does not stimulate B cell activation in vitro;
s) does not reduce levels of CD73 in H292 cells in vitro by more than 25%;
t) inhibits CD73 activity in tumors harvested from PBMC-humanized mice engrafted with A375 cells;
u) inhibits tumor growth in vivo in NOD-scid mice engrafted with MDA-MB-231 cells;
v) inhibits tumor growth in vivo in PBMC-humanized mice engrafted with Calu-6 cells; and
w) inhibits tumor growth in vivo in PBMC-humanized mice engrafted with A375 cells.

In some embodiments, the anti-CD73 antibody or antigen-binding portion has all of properties a)-w). In some embodiments, the anti-CD73 antibody or antigen-binding portion has at least properties a)-k), n), and s). In some embodiments, the anti-CD73 antibody or antigen-binding portion has at least properties a)-g), i)-k), and n). In some embodiments, the anti-CD73 antibody or antigen-binding portion has at least properties a)-d), i)-k), n), and s).

In some embodiments, an anti-CD73 antibody or antigen-binding portion described herein may inhibit tumor growth and/or induce tumor growth regression in vivo, may slow down or reverse metastasis in a cancer patient, and/or may prolong survival of a cancer patient. Any combination of the above properties is also contemplated.

In some embodiments, an anti-CD73 antibody or antigen-binding portion described herein increases T cell proliferation and/or decreases CD73 activity more effectively than anti-CD73 antibodies currently in clinical trials. For example, in certain embodiments, the anti-CD73 antibody or antigen-binding portion has at least one of the following properties:

at a concentration of 0.1 µg/mL, increases proliferation of activated CD4$^+$ T cells cultured with 100 µM AMP more than an antibody with HC and LC amino acid sequences comprising:
SEQ ID NOs: 17 and 19, respectively, of U.S. Patent Publication 2016/0129108;
SEQ ID NOs: 14 and 13, respectively, of U.S. Patent Publication 2018/0009899; or
SEQ ID NOs: 3 and 4, respectively, of U.S. Patent Publication 2018/0030144;
and/or
at a concentration of 10 µg/mL or higher, decreases CD73 activity in H292 cells after 24 hours of incubation more than an antibody with HC and LC amino acid sequences comprising:
SEQ ID NOs: 17 and 19, respectively, of U.S. Patent Publication 2016/0129108;
SEQ ID NOs: 14 and 13, respectively, of U.S. Patent Publication 2018/0009899; or
SEQ ID NOs: 3 and 4, respectively, of U.S. Patent Publication 2018/0030144.

In certain embodiments, an antibody or antigen-binding portion thereof of the present disclosure may be part of a larger immunoadhesin molecule, formed by covalent or noncovalent association of the antibody or antibody portion with one or more other proteins or peptides. Examples of such immunoadhesin molecules include use of the streptavidin core region to make a tetrameric scFv molecule (Kipriyanov et al., *Human Antibodies and Hybridomas* 6:93-101 (1995)) and use of a cysteine residue, a marker peptide and a C-terminal polyhistidine tag to make bivalent and biotinylated scFv molecules (Kipriyanov et al., *Mol. Immunol.* 31:1047-1058 (1994)). Other examples include where one or more CDRs from an antibody are incorporated into a molecule either covalently or noncovalently to make it an immunoadhesin that specifically binds to an antigen of interest. In such embodiments, the CDR(s) may be incorporated as part of a larger polypeptide chain, may be covalently linked to another polypeptide chain, or may be incorporated noncovalently.

In some embodiments, a fusion antibody or immunoadhesin may be made that comprises all or a portion of an anti-CD73 antibody of the present disclosure linked to another polypeptide. In certain embodiments, only the variable domains of the anti-CD73 antibody are linked to the polypeptide. In certain embodiments, the VH domain of an anti-CD73 antibody is linked to a first polypeptide, while the VL domain of an anti-CD73 antibody is linked to a second polypeptide that associates with the first polypeptide in a manner such that the VH and VL domains can interact with one another to form an antigen-binding site. In some embodiments, the VH domain is separated from the VL domain by a linker such that the VH and VL domains can interact with one another (e.g., single-chain antibodies). The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bi-specific antibody.

To create a single chain antibody (scFv), the VH- and VL-encoding DNA fragments are operatively linked to another fragment encoding a flexible linker, e.g., encoding the amino acid sequence (Gly4-Ser)3 (SEQ ID NO: 44), such that the VH and VL sequences can be expressed as a contiguous single-chain protein, with the VL and VH domains joined by the flexible linker. See, e.g., Bird et al., *Science* 242:423-426 (1988); Huston et al., *Proc. Natl. Acad. Sci. USA* 85:5879-5883 (1988); and McCafferty et al., *Nature* 348:552-554 (1990). The single chain antibody may be monovalent, if only a single VH and VL are used; bivalent, if two VH and VL are used; or polyvalent, if more than two VH and VL are used. Bi-specific or polyvalent antibodies may be generated that bind specifically to human CD73 and to another molecule, for instance.

In other embodiments, other modified antibodies may be prepared using anti-CD73 antibody-encoding nucleic acid molecules. For instance, "kappa bodies" (Ill et al., *Protein Eng.* 10:949-57 (1997)), "minibodies" (Martin et al., *EMBO J.* 13:5303-9 (1994)), "diabodies" (Holliger et al., *Proc. Natl. Acad. Sci. USA* 90:6444-6448 (1993)), or "Janusins" (Traunecker et al., *EMBO J.* 10:3655-3659 (1991) and Traunecker et al., *Int. J. Cancer* (Suppl.) 7:51-52 (1992)) may be prepared using standard molecular biological techniques following the teachings of the specification.

An anti-CD73 antibody or antigen-binding portion of the present disclosure can be derivatized or linked to another molecule (e.g., another peptide or protein). In general, the antibodies or portions thereof are derivatized such that CD73 binding is not affected adversely by the derivatization or labeling. Accordingly, the antibodies and antibody portions of the present disclosure are intended to include both intact and modified forms of the human anti-CD73 antibodies described herein. For example, an antibody or antibody portion of the present disclosure can be functionally linked (by chemical coupling, genetic fusion, noncovalent association or otherwise) to one or more other molecular entities, such as another antibody (e.g., a bi-specific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, e.g., to create bi-specific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available, e.g., from Pierce Chemical Company, Rockford, Ill.

An anti-CD73 antibody or antigen-binding portion can also be derivatized with a chemical group such as polyethylene glycol (PEG), a methyl or ethyl group, or a carbohydrate group. These groups may be useful to improve the biological characteristics of the antibody, e.g., to increase serum half-life.

An antibody or antigen-binding portion according to the present disclosure may also be labeled. As used herein, the terms "label" or "labeled" refer to incorporation of another molecule in the antibody. In some embodiments, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In some embodiments, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., 3H, 14C, 15N, 35S, 90Y, 99Tc, 111In, 125I, 131I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

In some embodiments, an antibody or antigen-binding portion according to the present disclosure may be conjugated to a cytotoxic agent to form an immunoconjugate. In some embodiments, an antibody or antigen-binding portion according to the present disclosure may be conjugated to a radioisotope.

In certain embodiments, the antibodies of the present disclosure may be present in a neutral form (including zwitterionic forms) or as a positively or negatively-charged species. In some embodiments, the antibodies may be complexed with a counterion to form a pharmaceutically acceptable salt.

The term "pharmaceutically acceptable salt" refers to a complex comprising one or more antibodies and one or more counterions, wherein the counterions are derived from pharmaceutically acceptable inorganic and organic acids and bases.

Anti-CD73 Antibody Compositions

The present disclosure also provides a combination therapy (e.g., a composition) that comprises one, two, three, four, or more of the anti-CD73 antibodies or antigen-binding portions thereof described herein. In certain embodiments, the combination therapy (e.g., composition) comprises two of the anti-CD73 antibodies or antigen-binding portions. The combination therapy may take the form of, e.g., a method of treatment using said antibodies or antigen-binding portions or a pharmaceutical composition comprising said antibodies or antigen-binding portions.

In some embodiments, the present disclosure provides a composition comprising a first anti-CD73 antibody or an antigen-binding portion thereof and a second anti-CD73 antibody or an antigen-binding portion thereof, wherein the first and second antibodies are:
  antibodies 21028 and 21046, respectively;
  antibodies 21028 and 21127, respectively;
  antibodies 21028 and 21163, respectively;
  antibodies 21046 and 21127, respectively;
  antibodies 21046 and 21163, respectively; or
  antibodies 21127 and 21163, respectively.

In some embodiments, the composition comprises antibodies or antigen-binding portions thereof that bind to the same epitope as, or compete for binding with, said first and second antibodies.

In some embodiments, the composition comprises an antibody or an antigen-binding portion thereof that comprises the H-CDR1-3 and L-CDR1-3 amino acid sequences of said first antibody, and an antibody or an antigen-binding portion thereof that comprises the H-CDR1-3 and L-CDR1-3 amino acid sequences of said second antibody.

In some embodiments, the composition comprises an antibody or an antigen-binding portion thereof that comprises a VH and a VL with amino acid sequences that are at least 80%, 85%, 90%, 91%, 92%, 93%, 94%, 95%, 96%, 97%, 98%, or 99% identical to the VH and VL amino acid sequences, respectively, of said first antibody, and an antibody or an antigen-binding portion thereof that comprises a VH and a VL with amino acid sequences that are at least 80%, 85%, 90%, 91%, 92%, 93%, 94%, 95%, 96%, 97%, 98%, or 99% identical to the VH and VL amino acid sequences, respectively, of said second antibody.

In some embodiments, the composition comprises an antibody or an antigen-binding portion thereof that comprises the VH and VL amino acid sequences of said first antibody, and an antibody or an antigen-binding portion thereof that comprises the VH and VL amino acid sequences of said second antibody.

In some embodiments, the composition comprises an antibody or an antigen-binding portion thereof that comprises the HC and LC amino acid sequences of said first antibody, and an antibody or an antigen-binding portion thereof that comprises the HC and LC amino acid sequences of said second antibody.

In certain embodiments, said composition may comprise one, two, or more antibodies or antigen-binding portions thereof selected from the group consisting of:
a) an antibody comprising H-CDR1-3 that comprise the amino acid sequences of SEQ ID NOs: 17-19, 23-25, 29-31, or 35-57, respectively;
b) an antibody whose VH is at least 90% identical in sequence to the amino acid sequence of SEQ ID NO: 9, 10, 11, or 12;
c) an antibody whose VH comprises the amino acid sequence of SEQ ID NO: 9, 10, 11, or 12;
d) an antibody whose HC comprises the amino acid sequences of SEQ ID NOs: 9 and 41, 10 and 41, 11 and 41, or 12 and 41;
e) an antibody comprising L-CDR1-3 that comprise the amino acid sequences of SEQ ID NOs: 20-22, 26-28, 32-34, or 38-40, respectively;
f) an antibody whose VL is at least 90% identical in sequence to the amino acid sequence of SEQ ID NO: 13, 14, 15, or 16;
g) an antibody whose VL comprises the amino acid sequence of SEQ ID NO: 13, 14, 15, or 16;
h) an antibody whose LC comprises the amino acid sequences of SEQ ID NOs: 13 and 42, 14 and 42, 15 and 42, or 16 and 42;
i) an antibody whose H-CDR1-3 and L-CDR1-3 comprise the amino acid sequences of SEQ ID NOs: 17-22, 23-28, 29-34, or 35-40, respectively;
j) an antibody comprising VH and VL that comprise amino acid sequences at least 90% identical to the amino acid sequences of SEQ ID NOs: 9 and 13, 10 and 14, 11 and 15, or 12 and 16, respectively;
k) an antibody comprising VH and VL that comprise the amino acid sequences of SEQ ID NOs: 9 and 13, 10 and 14, 11 and 15, or 12 and 16, respectively; and
l) an antibody comprising HC and LC that comprise the amino acid sequences of SEQ ID NOs: 9 and 41, and 13 and 42; 10 and 41, and 14 and 42; 11 and 41, and 15 and 42; or 12 and 41, and 16 and 42; respectively.

In some embodiments, an anti-CD73 antibody composition described herein may inhibit tumor growth and/or induce tumor growth regression in vivo, may slow down or reverse metastasis in a cancer patient, and/or may prolong survival of a cancer patient. Any combination of the above properties is also contemplated.

The present disclosure also provides a method for producing an anti-CD73 antibody composition described herein, comprising providing a first anti-CD73 antibody or antigen-binding portion and a second anti-CD73 antibody or antigen-binding portion, and admixing the two antibodies or portions.

Bi-Specific Binding Molecules

The present disclosure also provides a bi-specific binding molecule having the binding specificity (e.g., comprising the antigen-binding portions, such as the six CDRs or the VH and VL) of an anti-CD73 antibody described herein. In some embodiments, the bi-specific binding molecule additionally has the binding specificity of another, distinct anti-CD73 antibody (e.g., another anti-CD73 antibody described herein) or an antibody that targets a different protein, such as a cancer antigen or another cell surface molecule whose activity mediates a disease condition such as cancer. Such bi-specific binding molecules are known in the art, and examples of different types of bi-specific binding molecules are given elsewhere herein. In certain embodiments, the bi-specific binding molecule may bind to CD73 and PD-1, CD73 and PD-L1, or CD73 and CTLA-4.

Nucleic Acid Molecules and Vectors

The present disclosure also provides nucleic acid molecules and sequences encoding anti-CD73 antibodies or antigen-binding portions thereof described herein. In some embodiments, different nucleic acid molecules encode the heavy chain and light chain amino acid sequences of the anti-CD73 antibody or antigen-binding portion. In other embodiments, the same nucleic acid molecule encodes the heavy chain and light chain amino acid sequences of the anti-CD73 antibody or antigen-binding portion.

A reference to a nucleotide sequence encompasses its complement unless otherwise specified. Thus, a reference to a nucleic acid having a particular sequence should be understood to encompass its complementary strand, with its complementary sequence. The term "polynucleotide" as referred to herein means a polymeric form of nucleotides of at least 10 bases in length, either ribonucleotides or deoxynucleotides or a modified form of either type of nucleotide. The term includes single- and double-stranded forms.

In some embodiments, the present disclosure provides a nucleic acid molecule comprising a nucleotide sequence that encodes the heavy chain or an antigen-binding portion thereof, or a nucleotide sequence that encodes the light chain or an antigen-binding portion thereof, or both, of an anti-CD73 antibody or antigen-binding portion thereof described herein.

The present disclosure also provides nucleotide sequences that are at least 70%, 75%, 80%, 85%, 90%, 95%, 97%, 98% or 99% identical to one or more nucleotide sequences recited herein, e.g., to a nucleotide sequence selected from the group consisting of SEQ ID NOs: 1-8, or to a nucleotide sequence encoding an amino acid sequence selected from the group consisting of SEQ ID NOs: 9-16. The term "percent sequence identity" in the context of nucleic acid sequences refers to the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (see, e.g., Pearson, *Methods Enzymol.* 183:63-98 (1990); Pearson, *Methods Mol. Biol.* 132:185-219 (2000); Pearson, *Methods Enzymol.* 266:227-258 (1996); and Pearson, *J. Mol. Biol.* 276:71-84 (1998); incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

In some embodiments, the present disclosure provides a nucleic acid molecule comprising a nucleotide sequence selected from the group consisting of SEQ ID NOs: 1-8. In certain embodiments, the nucleic acid molecule comprises the nucleotide sequences of SEQ ID NOs: 1 and 5, SEQ ID NOs: 2 and 6, SEQ ID NOs: 3 and 7, or SEQ ID NOs: 4 and 8.

In any of the above embodiments, the nucleic acid molecules may be isolated. Nucleic acid molecules referred to herein as "isolated" or "purified" are nucleic acids which (1) have been separated away from the nucleic acids of the genomic DNA or cellular RNA of their source of origin; and/or (2) do not occur in nature.

In some embodiments, the present disclosure provides a vector suitable for expressing one or both of the chains of an antibody or antigen-binding portion thereof as described herein. The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The present disclosure provides vectors comprising nucleic acid molecules that encode the heavy chain, the light chain, or both the heavy and light chains of an anti-CD73 antibody as described herein or an antigen-binding portion thereof. In certain embodiments, a vector of the present disclosure comprises a nucleic acid molecule described herein. The present disclosure further provides vectors comprising nucleic acid molecules encoding fusion proteins, modified antibodies, antibody fragments, and probes thereof. The vector may further comprise an expression control sequence.

The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

A nucleic acid molecule encoding the heavy and/or light chain of an anti-CD73 antibody or antigen-binding portion thereof as described herein can be isolated from any source that produces such an antibody or portion. In some embodiments, the nucleic acid molecules are isolated from B cells that express an anti-CD73 antibody isolated from an animal immunized with a human CD73 antigen, or from an immortalized cell produced from such a B cell. Methods of isolating nucleic acids encoding an antibody are well-known in the art. mRNA may be isolated and used to produce cDNA for use in polymerase chain reaction (PCR) or cDNA cloning of antibody genes. In certain embodiments, a nucleic acid molecule as described herein can be synthesized rather than isolated.

In some embodiments, a nucleic acid molecule as described herein comprises a nucleotide sequence encoding a VH domain from an anti-CD73 antibody or antigen-binding portion as described herein joined in-frame to a nucleotide sequence encoding a heavy chain constant region from any source. Similarly, a nucleic acid molecule as described herein can comprise a nucleotide sequence encoding a VL domain from an anti-CD73 antibody or antigen-binding portion as described herein joined in-frame to a nucleotide sequence encoding a light chain constant region from any source.

In some embodiments of the present disclosure, nucleic acid molecules encoding the VH and/or VL may be "converted" to full-length antibody genes. In certain embodiments, nucleic acid molecules encoding the VH or VL domains are converted to full-length antibody genes by insertion into an expression vector already encoding heavy chain constant (CH) or light chain constant (CL) regions, respectively, such that the VH segment is operatively linked to the CH segment(s) within the vector, and/or the VL segment is operatively linked to the CL segment within the vector. In some embodiments, nucleic acid molecules encoding the VH and/or VL domains are converted into full-length antibody genes by linking, e.g., ligating, a nucleic acid molecule encoding a VH and/or VL domain to a nucleic acid molecule encoding a CH and/or CL region using standard molecular biological techniques. Nucleic acid molecules encoding the full-length heavy and/or light chains may then be expressed from a cell into which they have been introduced and the anti-CD73 antibody isolated.

The nucleic acid molecules may be used to recombinantly express large quantities of anti-CD73 antibodies. The nucleic acid molecules also may be used to produce chimeric antibodies, bi-specific antibodies, single chain antibodies, immunoadhesins, diabodies, mutated antibodies and antibody derivatives, as described herein.

In some embodiments, a nucleic acid molecule of the present disclosure is used as a probe or PCR primer for a specific antibody sequence. For instance, the nucleic acid can be used as a probe in diagnostic methods or as a PCR primer to amplify regions of DNA that could be used, inter alia, to isolate additional nucleic acid molecules encoding variable domains of anti-CD73 antibodies. In some embodiments, the nucleic acid molecules are oligonucleotides. In some embodiments, the oligonucleotides are from highly variable domains of the heavy and light chains of the antibody of interest. In some embodiments, the oligonucleotides encode all or a part of one or more of the CDRs of the anti-CD73 antibodies or antigen-binding portions thereof of the present disclosure as described herein.

In some embodiments, the nucleic acid molecules and vectors may be used to make mutated anti-CD73 antibodies. The antibodies may be mutated in the variable domains of the heavy and/or light chains, e.g., to alter a binding property of the antibody. For example, a mutation may be made in one or more of the CDRs to increase or decrease the $K_D$ of the anti-CD73 antibody, to increase or decrease $k_{off}$, or to alter the binding specificity of the antibody. In some embodiments, one or more mutations are made at an amino acid residue that is known to be changed compared to the germline in a monoclonal antibody of the present disclosure. The mutations may be made in a CDR or framework region of a variable domain, or in a constant region. In certain embodiments, the mutations are made in a variable domain. In particular embodiments, one or more mutations are made at an amino acid residue that is known to be changed compared to the germline in a CDR or framework region of a variable domain of an antibody or antigen-binding portion thereof of the present disclosure.

In some embodiments, the framework region(s) are mutated so that the resulting framework region(s) have the amino acid sequence of the corresponding germline gene. A mutation may be made in a framework region or constant region, e.g., to increase the half-life of the anti-CD73 antibody. See, e.g., PCT Publication WO 00/09560. A mutation in a framework region or constant region also can be made to alter the immunogenicity of the antibody, and/or to provide a site for covalent or non-covalent binding to another molecule. According to the present disclosure, an antibody may have mutations in any one or more of the CDRs or framework regions of the variable domain or in the constant region.

In some embodiments, the anti-CD73 antibodies of the present disclosure or antigen-binding portions thereof are expressed by inserting DNAs encoding partial or full-length light and heavy chains, obtained as described above, into expression vectors such that the genes are operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody coding sequence may be ligated into a vector such that transcriptional and translational control sequences within the vector serve their intended function of regulating the transcription and translation of the antibody coding sequence. The expression vector and expression control sequences may be chosen to be compatible with the expression host cell used. The antibody light chain coding sequence and the antibody heavy chain coding sequence can be inserted into the same or separate vectors, and may be operatively linked to the same or different expression control sequences (e.g., promoters). In some embodiments, both coding sequences are inserted into the same expression vector and may be operatively linked to the same expression control sequences (e.g., a common promoter), to separate identical expression control sequences (e.g., promoters), or to different expression control sequences (e.g., promoters). The antibody coding sequences may be inserted into the expression vector by standard methods (e.g., ligation of complementary restriction sites on the antibody gene fragment and vector, or blunt end ligation if no restriction sites are present).

A convenient vector is one that encodes a functionally complete human CH or CL immunoglobulin sequence, with appropriate restriction sites engineered so that any VH or VL sequence can easily be inserted and expressed, as described above. The HC- and LC-encoding genes in such vectors may contain intron sequences that will result in enhanced overall antibody protein yields by stabilizing the related mRNA. The intron sequences are flanked by splice donor and splice acceptor sites, which determine where RNA splicing will occur. Location of intron sequences can be either in variable or constant regions of the antibody chains, or in both variable and constant regions when multiple introns are used. Polyadenylation and transcription termination may occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors of the present disclosure may carry regulatory sequences that control the expression of the antibody chain genes in a host cell. It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see, e.g., U.S. Pat. Nos. 5,168,062, 4,510,245 and 4,968,615. Methods for expressing antibodies in plants, including a description of promoters and vectors, as well as transformation of plants, are known in the art. See, e.g., U.S. Pat. No. 6,517,529. Methods of expressing polypeptides in bacterial cells or fungal cells, e.g., yeast cells, are also well known in the art.

In addition to the antibody chain genes and regulatory sequences, the recombinant expression vectors of the present disclosure may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. For example, selectable marker genes include the dihydrofolate reductase (DHFR) gene (for use in dhfr-host cells with methotrexate selection/amplification), the neo gene (for G418 selection), and the glutamate synthetase gene.

Host Cells and Methods of Antibody and Antibody Composition Production

The present disclosure also provides methods for producing the antibody compositions and antibodies and antigen-binding portions thereof described herein. In some embodiments, the present disclosure relates to a method for producing an anti-CD73 antibody or antigen-binding portion as described herein, comprising providing a recombinant host cell comprising a nucleotide sequence that encodes the heavy chain or an antigen-binding portion thereof, and a nucleotide sequence that encodes the light chain or an antigen-binding portion thereof, of an anti-CD73 antibody or antigen-binding portion described herein; cultivating said host cell under conditions suitable for expression of the antibody or antigen-binding portion; and isolating the resulting antibody or antigen-binding portion. Antibodies or antigen-binding portions produced by such expression in such recombinant host cells are referred to herein as "recombinant" antibodies or antigen-binding portions. The present disclosure also provides progeny cells of such host cells, and antibodies or antigen-binding portions produced by same.

The term "recombinant host cell" (or simply "host cell"), as used herein, means a cell into which a recombinant expression vector has been introduced. By definition, a recombinant host cell does not occur in nature. The present disclosure provides host cells that may comprise, e.g., a vector as described herein. The present disclosure also provides host cells that comprise, e.g., a nucleotide sequence encoding the heavy chain or an antigen-binding portion thereof, a nucleotide sequence encoding the light chain or an antigen-binding portion thereof, or both, of an anti-CD73 antibody or antigen-binding portion thereof described herein. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

Nucleic acid molecules encoding anti-CD73 antibodies and antigen-binding portions thereof and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455. Methods of transforming plant cells are well known in the art, including, e.g., Agrobacterium-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NS0 cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected by determining which cell lines have high expression levels. Other cell lines that may be used are insect cell lines, such as Sf9 or Sf21 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Plant host cells include, e.g., Nicotiana, Arabidopsis, duckweed, corn, wheat, potato, etc. Bacterial host cells include E. coli and *Streptomyces* species. Yeast host cells include *Schizosaccharomyces pombe, Saccharomyces cerevisiae* and *Pichia pastoris*.

Further, expression of antibodies of the present disclosure or antigen-binding portions thereof from production cell lines can be enhanced using a number of known techniques. For example, the glutamine synthetase gene expression system (the GS system) is a common approach for enhancing expression under certain conditions. The GS system is discussed in whole or part in connection with EP Patents 0 216 846, 0 256 055, 0 323 997 and 0 338 841.

It is likely that antibodies expressed by different cell lines or in transgenic animals will have different glycosylation patterns from each other. However, all antibodies encoded by the nucleic acid molecules provided herein, or comprising the amino acid sequences provided herein are part of the present disclosure, regardless of the glycosylation state of the antibodies, and more generally, regardless of the presence or absence of post-translational modification(s).

Pharmaceutical Compositions

Another aspect of the present disclosure is a pharmaceutical composition comprising as an active ingredient (or as the sole active ingredient) an anti-CD73 antibody or antigen-binding portion thereof, bi-specific binding molecule, or antibody composition of the present disclosure. The pharmaceutical composition may additionally comprise a pharmaceutically acceptable excipient. In some embodiments, the pharmaceutical compositions are intended for amelioration, prevention, and/or treatment of cancer, e.g., a cancer described herein. In certain embodiments, the cancer is in a tissue such as skin, lung, intestine, colon, ovary, brain, prostate, kidney, soft tissues, the hematopoietic system, head and neck, liver, bone, bladder, breast, stomach, uterus, cervix, and pancreas. In certain embodiments, the cancer is melanoma, head and neck cancer, breast cancer (e.g., triple negative breast cancer), bladder cancer, lung cancer (e.g., non-small cell lung cancer), pancreatic cancer (e.g., pancreatic ductal adenocarcinoma), ovarian cancer, renal cell carcinoma, prostate cancer, colorectal cancer, cholangiocarcinoma, thyroid cancer, or testicular cancer.

Pharmaceutical compositions of the present disclosure will comprise one or more anti-CD73 antibodies, antigen-binding portions, antibody compositions, or bi-specific binding molecules of the present disclosure, e.g., one or two anti-CD73 antibodies, antigen-binding portions, or bi-specific binding molecules. In some embodiments, the composition comprises a single anti-CD73 antibody of the present disclosure or an antigen-binding portion thereof. In some embodiments, the composition comprises two distinct anti-CD73 antibodies of the present disclosure or antigen-binding portions thereof.

In some embodiments, the pharmaceutical composition may comprise at least one anti-CD73 antibody or antigen-binding portion thereof of the present disclosure, e.g., one anti-CD73 antibody or portion, and one or more additional antibodies that target one or more relevant cell surface receptors, e.g., one or more cancer-relevant receptors.

Generally, the antibodies, antigen-binding portions, and bi-specific binding molecules of the present disclosure are suitable to be administered as a formulation in association with one or more pharmaceutically acceptable excipient(s), e.g., as described below.

The term "excipient" is used herein to describe any ingredient other than the compound(s) of the present disclosure. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

Pharmaceutical compositions of the present disclosure and methods for their preparation will be readily apparent to those skilled in the art. Such compositions and methods for their preparation may be found, for example, in *Remington's Pharmaceutical Sciences,* 19th Edition (Mack Publishing Company, 1995). Pharmaceutical compositions are preferably manufactured under GMP (good manufacturing practices) conditions.

A pharmaceutical composition of the present disclosure may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Formulations of a pharmaceutical composition suitable for parenteral administration typically comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In some embodiments of a formulation for parenteral administration, the active ingredient is provided in dry (i.e., powder or granular) form for reconstitution with a suitable vehicle (e.g., sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release.

Modified release formulations include delayed-, sustained-, pulsed-, controlled-, targeted and programmed release.

In some embodiments, sterile injectable solutions can be prepared by incorporating the anti-CD73 antibody, antigen-binding portion thereof, bi-specific binding molecule, or antibody composition in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yield a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts or gelatin, and/or by using modified-release coatings (e.g., slow-release coatings).

The antibodies of the present disclosure can also be administered intranasally or by inhalation, typically in the form of a dry powder (either alone, as a mixture, or as a mixed component particle, for example, mixed with a suitable pharmaceutically acceptable excipient) from a dry powder inhaler; as an aerosol spray from a pressurised container, pump, spray, atomiser (preferably an atomiser using electrohydrodynamics to produce a fine mist), or nebuliser, with or without the use of a suitable propellant; or as nasal drops.

The antibodies and antibody portions of the present disclosure may also be formulated for an oral route administration. Oral administration may involve swallowing, so that the compound enters the gastrointestinal tract, and/or buccal, lingual, or sublingual administration by which the compound enters the blood stream directly from the mouth. Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches. Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Therapeutic Uses of Antibodies and Compositions of the Present Disclosure

In some embodiments, the anti-CD73 antibodies and antigen-binding portions thereof, anti-CD73 compositions, and bi-specific binding molecules of the present disclosure are used to decrease CD73 activity in a mammal (e.g., a human) in need thereof. For example, a physician can boost anti-tumor activity in a patient by administering an anti-CD73 antibody of the present disclosure, alone or in combination with other therapeutic agents (sequentially or concurrently). The anti-CD73 antibody decreases the activity of CD73, inhibiting a pathway that suppresses the patient's anti-tumor response.

In certain embodiments, the antibodies or antigen-binding portions thereof, compositions, or bi-specific binding molecules are for use in the treatment of a CD73-positive cancer. The cancer may be in one or more tissues such as skin, lung, intestine, colon, ovary, brain, prostate, kidney, soft tissues, the hematopoietic system, head and neck, liver, bone, bladder, breast, stomach, uterus, cervix, and pancreas.

In some embodiments, cancers treated by the anti-CD73 antibodies, antigen-binding portions, bi-specific binding molecules, and/or antibody compositions of the present disclosure may include, e.g., melanoma (e.g., advanced or metastatic melanoma), skin basal cell cancer, glioblastoma, glioma, gliosarcoma, astrocytoma, meningioma, neuroblastoma, adrenocortical cancer, head and neck squamous cell cancer, oral cancer, salivary gland cancer, nasopharyngeal cancer, breast cancer, thyroid cancer, lung cancer (e.g., non-small cell lung cancer, small cell lung cancer, and squamous cell lung cancer), esophageal cancer, gastroesophageal junction cancer, gastric cancer, gastrointestinal cancer, primary peritoneal cancer, liver cancer, hepatocellular carcinoma, biliary tract cancer, cholangiocarcinoma, colon cancer, colorectal carcinoma, ovarian cancer, fallopian tube cancer, bladder cancer, upper urinary tract cancer, urothelial cancer, renal cell carcinoma, kidney cancer, genitourinary cancer, cervical cancer, prostate cancer, testicular cancer, fibrosarcoma, liposarcoma, rhabdomyosarcoma, osteosarcoma, histiocytoma, pancreatic cancer, endometrial cancer, cancer of the appendix, advanced Merkel cell cancer, multiple myeloma, sarcoma, choriocarcinoma, erythroleukemia, acute lymphoblastic leukemia, acute monocytic leukemia, acute promyelocytic leukemia, acute myeloid leukemia, chronic myeloid leukemia, chronic lymphocytic leukemia, acute lymphoblastic leukemia, mast cell leukemia, small lymphocytic lymphoma, Burkitt's lymphoma, Hodgkin's lymphoma, non-Hodgkin's lymphoma, diffuse large B cell lymphoma, follicular lymphoma, monocytic lymphoma, HTLV-associated T cell leukemia/lymphoma, mesothelioma, and solid tumors. The cancer may be, e.g., at an early, intermediate, late, locally advanced, or metastatic stage, and may be relapsed or refractory to other therapeutics (e.g., other anti-CD73 therapeutics) or there may be no standard therapy available.

In some embodiments, cancers treated by the anti-CD73 antibodies, antigen-binding portions, compositions, and/or bi-specific binding molecules of the present disclosure may include, e.g., melanoma, head and neck cancer, breast cancer (e.g., triple negative breast cancer), bladder cancer, lung cancer (e.g., non-small cell lung cancer), pancreatic cancer (e.g., pancreatic ductal adenocarcinoma), ovarian cancer, renal cell carcinoma, prostate cancer, colorectal cancer, cholangiocarcinoma, thyroid cancer, and testicular cancer.

"Treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

"Therapeutically effective amount" refers to the amount of the therapeutic agent being administered that will relieve to some extent one or more of the symptoms of the disorder being treated. A therapeutically effective amount of an anti-cancer therapeutic may, for example, result in delayed tumor growth, tumor shrinkage, increased survival, elimination of cancer cells, slowed or decreased disease progression, reversal of metastasis, or other clinical endpoints desired by healthcare professionals.

The anti-CD73 antibodies or antigen-binding portions thereof, antibody compositions, or bi-specific binding molecules described herein may be administered alone or in combination with one or more other drugs or antibodies (or as any combination thereof). The pharmaceutical compositions, methods and uses described herein thus also encompass embodiments of combinations (co-administration) with other active agents, as detailed below.

As used herein, the terms "co-administration," "co-administered" and "in combination with," referring to the anti-CD73 antibodies and antigen-binding portions thereof, antibody compositions, and bi-specific binding molecules of the present disclosure with one or more other therapeutic agents, is intended to mean, and does refer to and include the following:
a) simultaneous administration of such combination of antibody/antigen-binding portion/antibody composition/bi-specific binding molecule of the present disclosure and therapeutic agent(s) to a patient in need of treatment, when such components are formulated together into a single dosage form which releases said components at substantially the same time to said patient,
b) substantially simultaneous administration of such combination of antibody/antigen-binding portion/antibody composition/bi-specific binding molecule of the present disclosure and therapeutic agent(s) to a patient in need of treatment, when such components are formulated apart from each other into separate dosage forms which are taken at substantially the same time by said patient, whereupon said components are released at substantially the same time to said patient,
c) sequential administration of such combination of antibody/antigen-binding portion/antibody composition/bi-specific binding molecule of the present disclosure and therapeutic agent(s) to a patient in need of treatment, when such components are formulated apart from each other into separate dosage forms which are taken at consecutive times by said patient with a significant time interval between each administration, whereupon said components are released at substantially different times to said patient; and
d) sequential administration of such combination of antibody/antigen-binding portion/antibody composition/bi-specific binding molecule of the present disclosure and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

The anti-CD73 antibodies or antigen-binding portions thereof, antibody compositions, or bi-specific binding molecules of the present disclosure may be administered without additional therapeutic treatments, i.e., as a stand-alone therapy (monotherapy). Alternatively, treatment with the anti-CD73 antibodies or antigen-binding portions thereof, antibody compositions, or bi-specific binding molecules of the present disclosure may include at least one additional therapeutic treatment (combination therapy), e.g., an immunostimulatory agent, an anti-cancer agent (e.g., a chemotherapeutic agent, an anti-neoplastic agent, an anti-angiogenic agent, or a tyrosine kinase inhibitor), or a vaccine (e.g., a tumor vaccine).

In some embodiments, the antibody or antigen-binding portion thereof, antibody composition, or bi-specific binding molecule may be co-administered or formulated with another medication/drug for the treatment of cancer. The additional therapeutic treatment may comprise, e.g., an immunostimulatory agent, a vaccine, a chemotherapeutic agent, an anti-neoplastic agent, an anti-angiogenic agent, a tyrosine kinase inhibitor, and/or radiation therapy. In some embodiments, the additional therapeutic treatment may comprise a different anti-cancer antibody.

Pharmaceutical articles comprising an anti-CD73 antibody or antigen-binding portion thereof, antibody composition, or bi-specific binding molecule described herein and at least one other agent (e.g., a chemotherapeutic, anti-neoplastic, or anti-angiogenic agent) may be used as a combination treatment for simultaneous, separate or successive administration in cancer therapy. The other agent may by any agent suitable for treatment of the particular cancer in question, for example, an agent selected from the group consisting of alkylating agents, e.g., platinum derivatives such as cisplatin, carboplatin and/or oxaliplatin; plant alkoids, e.g., paclitaxel, docetaxel and/or irinotecan; antitumor antibiotics, e.g., doxorubicin (adriamycin), daunorubicin, epirubicin, idarubicin mitoxantrone, dactinomycin, bleomycin, actinomycin, luteomycin, and/or mitomycin; topoisomerase inhibitors such as topotecan; antimetabolites, e.g., fluorouracil and/or other fluoropyrimidines; FOLFOX; osimertinib; cyclophosphamide; anthracycline; dacarbazine; gemcitabine; or any combination thereof. In some embodiments, the anti-CD73 antibody or antigen-binding portion thereof, antibody composition, or bi-specific binding molecule described herein reestablishes responsiveness to the other agent.

An anti-CD73 antibody or antigen-binding portion thereof, antibody composition, or bi-specific binding molecule of the present disclosure may also be used in combination with other anti-cancer therapies such as vaccines, cytokines, enzyme inhibitors, immunostimulatory compounds, and T cell therapies. In the case of a vaccine, it may be, e.g., a protein, peptide or DNA vaccine containing one or more antigens which are relevant for the cancer being treated, or a vaccine comprising dendritic cells along with an antigen. Suitable cytokines include, for example, IL-2, IFN-gamma and GM-CSF. An example of a type of enzyme inhibitor that has anti-cancer activity is an indoleamine-2, 3-dioxygenase (IDO) inhibitor, for example, 1-methyl-D-tryptophan (1-D-MT). Adoptive T cell therapy refers to various immunotherapy techniques that involve expanding or engineering patients' own T cells to recognize and attack their tumors.

It is also contemplated that an anti-CD73 antibody or antigen-binding portion thereof, antibody composition, or bi-specific binding molecule of the present disclosure may be used in adjunctive therapy in connection with tyrosine kinase inhibitors. These are synthetic, mainly quinazoline-derived, low molecular weight molecules that interact with the intracellular tyrosine kinase domain of receptors and inhibit ligand-induced receptor phosphorylation, e.g., by competing for the intracellular Mg-ATP binding site.

In some embodiments, the antibody or antigen-binding portion thereof, antibody composition, or bi-specific binding molecule may be used in combination with a medication/drug that mediates immune system activation, including, but not limited to, an agent that modulates the expression or activity of A2AR, A1AR, A2BR, A3AR, ADA, ALP, BTLA, B7-H3, B7-H4, CTLA-4, CD27, CD28, CD39, CD40, CD47, CD55, CD122, CD137, CD160, CGEN-15049, CHK1, CHK2, CTLA-3, CEACAM (e.g., CEACAM-1 and/or CEACAM-5), GAL9, GITR, HVEM, LAG-3, LY108, LAIR1, ICOS, IDO, KIR, NKG2A, PAP, PD-1/PD-L1/PD-L2, OX40, TIGIT, TIM-3, TGFR-beta, TNFR2, VISTA, LILRB2, CMTM6 and/or 2B4. In some embodiments, the agent modulates the expression of CD39, NKG2A, LAG-3, TIM-3, or TNFR2. In certain embodiments, the agent is a small molecule inhibitor. In certain embodiments, the agent is an antibody or an antigen-binding fragment thereof that binds to one of the above molecules. In particular embodiments, the agent is an anti-PD-L1 antibody (e.g., durvalumab or atezolizumab), an anti-PD-1 antibody, or an anti-CTLA-4 antibody. It is also contemplated that an anti-CD73 antibody or antigen-binding portion thereof, antibody composition, or bi-specific binding molecule of the present disclosure may be used in combination with a cytokine (e.g., IL-1, IL-2, IL-12, IL-15 or IL-21), an EGFR inhibitor, a VEGF inhibitor, etc.

In certain embodiments, the antibodies and antigen-binding portions, antibody compositions, or bi-specific binding molecules of the present disclosure may be administered in combination with another inhibitor of the adenosinergic pathway, which may target, e.g., CD73, CD39, or CD38, or an adenosine receptor selected from A1R, A2AR, A2BR, and/or A3R. Such inhibitors include, without limitation, AR1 inhibitors (e.g., DPCPX, SCH58261, and FSPTP), A2AR inhibitors (e.g., PBF-509, CPI-444, AZD4635, ZM241385, AB928, istradefylline, SYN-115, ANR94, PSB1115, PSB603, and NIR178), A2B inhibitors (e.g., miR-128b, ATL801, aminophylline, MRS1754, IPDX, and PBF-1129), and A3R inhibitors (e.g., MRS1191, MRS1220, MRS1523, and CF-102). Other examples of such inhibitors include other anti-CD73 antibodies, as well as anti-CD39 and anti-CD38 antibodies. In some embodiments, an anti-CD73 antibody or antigen-binding portion thereof, bi-specific antibody, or antibody composition of the present disclosure may be administered in combination with A001421, APCP, oleclumab, CPX-006/CPI-006, CPX-016, NZV-930, BMS-986179, IPH53, PT199, durvalumab, atezolizumab, daratumumab, or isatuximab.

The present disclosure also contemplates the use of sequences (e.g., the six CDR or VH and VL sequences) of an anti-CD73 antibody or antigen-binding portion described herein in the preparation of a chimeric antigen receptor, which may be for use in CAR-T technology.

It is understood that the antibodies and antigen-binding portions thereof, antibody compositions, and bi-specific binding molecules of the present disclosure may be used in a method of treatment as described herein, may be for use in a treatment as described herein, and/or may be for use in the manufacture of a medicament for a treatment as described herein. The present disclosure also provides kits and articles of manufacture comprising the antibodies and antigen-binding portions thereof, antibody compositions, and bi-specific binding molecules described herein.

Dose and Route of Administration

The antibodies or antigen-binding portions thereof, antibody compositions, or bi-specific binding molecules of the present disclosure may be administered in an effective amount for treatment of the condition in question, i.e., at dosages and for periods of time necessary to achieve a desired result. A therapeutically effective amount may vary according to factors such as the particular condition being treated, the age, sex and weight of the patient, and whether the antibodies are being administered as a stand-alone treatment or in combination with one or more additional anti-cancer treatments.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the present disclosure are generally dictated by and directly dependent on (a) the unique characteristics of the therapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen are adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present disclosure.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the embodied composition. Further, the dosage regimen with the compositions of the present disclosure may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present disclosure encompasses intra-patient dose-escalation as determined by the skilled artisan. Determining of appropriate dosages and regimens is well-known in the relevant art and would be understood to be encompassed by the skilled artisan once provided the teachings disclosed herein.

An effective amount for tumor therapy may be measured by its ability to stabilize disease progression and/or ameliorate symptoms in a patient, and preferably to reverse disease progression, e.g., by reducing tumor size. The ability of an antibody, antigen-binding portion, antibody composition, or bi-specific binding molecule of the present disclosure to inhibit cancer may be evaluated by in vitro assays, e.g., as described in the examples, as well as in suitable animal models that are predictive of the efficacy in human tumors. Suitable dosage regimens will be selected in order to provide an optimum therapeutic response in each particular situation, for example, administered as a single bolus or as a continuous infusion, and with possible adjustment of the dosage as indicated by the exigencies of each case.

The antibodies or antigen-binding portions thereof, antibody compositions, or bi-specific binding molecules of the present disclosure may be administered by any method for administering peptides, proteins or antibodies accepted in the art, and are typically suitable for parenteral administration. As used herein, "parenteral administration" includes any route of administration characterized by physical breaching of a tissue of a subject and administration through the breach in the tissue, thus generally resulting in the direct administration into the blood stream, into muscle, or into an internal organ. Parenteral administration thus includes, but is not limited to, administration by injection, by application through a surgical incision, by application through a tissue-penetrating non-surgical wound, and the like. In particular, parenteral administration is contemplated to include, but is not limited to, subcutaneous, intraperitoneal, intramuscular, intrasternal, intracisternal, intravenous, intraarterial, intrathecal, intraurethral, intracranial, intratumoral, and intrasynovial injection or infusions. Particular embodiments include the intravenous and the subcutaneous routes.

Diagnostic Uses and Compositions

The antibodies and antigen-binding portions of the present disclosure also are useful in diagnostic processes (e.g., in vitro, ex vivo). For example, the antibodies and antigen-binding portions can be used to detect and/or measure the level of CD73 in a sample from a patient (e.g., a tissue sample, or a body fluid sample such as an inflammatory exudate, blood, serum, bowel fluid, saliva, or urine). Suitable detection and measurement methods include immunological methods such as flow cytometry, enzyme-linked immunosorbent assays (ELISA), chemiluminescence assays, radioimmunoassays, and immunohistology. The present disclosure further encompasses kits (e.g., diagnostic kits) comprising the antibodies and antigen-binding portions described herein.

Articles of Manufacture and Kits

The present disclosure also provides articles of manufacture, e.g., kits, comprising one or more containers (e.g., single-use or multi-use containers) containing a pharmaceutical composition of an anti-CD73 antibody or antigen-binding portion thereof, composition, or bi-specific binding molecule described herein, optionally an additional biologically active molecule (e.g., another therapeutic agent), and instructions for use. The antibody or antigen-binding portion, composition, or bi-specific binding molecule, and optional additional biologically active molecule, can be packaged separately in suitable packing such as a vial or ampule made from non-reactive glass or plastic. In certain embodiments, the vial or ampule holds a concentrated stock (e.g., 2×, 5×, 10× or more) of the antibody or antigen-binding portion, composition, or bi-specific binding molecule and optionally the biologically active molecule. In certain embodiments, the articles of manufacture such as kits include a medical device for administering the antibody or antigen-binding portion, composition, or bi-specific binding molecule and/or biologically active molecule (e.g., a syringe and a needle); and/or an appropriate diluent (e.g., sterile water and normal saline). The present disclosure also includes methods for manufacturing said articles.

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control.

Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein.

Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers.

All publications and other references mentioned herein are incorporated by reference in their entirety. Although a number of documents are cited herein, this citation does not constitute an admission that any of these documents forms part of the common general knowledge in the art.

In order that the present disclosure may be better understood, the following examples are set forth. These examples are for purposes of illustration only and are not to be construed as limiting the scope of the present disclosure in any manner.

EXAMPLES

Example 1. Cloning of Anti-CD73 Antibodies from Rat B Cells

Materials and Methods

Antibodies against human CD73 were isolated from an antibody repertoire derived from OmniRat® rats (Osborn et al., *J Immunol.* 190(4):1481-90 (2013)), a transgenic rat strain from Ligand Pharmaceuticals Inc. that produces antibodies with fully human idiotypes. Cloning of rat-derived antibody genes from single-cell sorted antibody-secreting B cells (ASC) was performed by means of Symplex™ antibody discovery technology (Meijer et al., *J Mol Biol* 358 (3):764-72 (2006)).

The antibody repertoire constructs encoding fully human immunoglobulins in $IgG_1$-LALA format (see below) were transfected into HEK293 cells. Cell supernatants were screened for binding to CD73 expressed on the surface of CHO cells using flow cytometry in a high-throughput format. CD73 reactive clones were analyzed by DNA sequencing and antibody-encoding DNA sequences were extracted. Selected antibody clones were expressed and tested functionally as described below.

Missense mutations in the amino termini of heavy and light chains that were introduced by the use of degenerate primers in the Symplex™ cloning of the antibody-encoding cDNA fragments were corrected back to germline sequence. Table 1 shows the heavy and light chain variable domain nucleotide sequences of the germlined antibodies designated 21028, 21046, 21127 and 21163. The correction process involves amino terminal sequence correction to germline as well as codon usage optimization. The targets for matching to human germline sequences were identified by blast homology searches for the heavy chain and the light chain variable regions.

Protein sequences of the variable domains, the constant regions and the complementarity determining regions (CDR) of antibodies 21028, 21046, 21127 and 21163 are shown in Table 2, Table 3 and Table 4, respectively.

Results

Table 1 shows nucleotide sequences encoding the variable domains of antibodies 21028, 21046, 21127 and 21163.

TABLE 1

Variable domain nucleotide sequences of antibodies 21028, 21046, 21127 and 21163

| | Sequence (5' to 3') |
|---|---|
| 21028 VH SEQ ID NO: 1 | GAGGTGCAGCTGGTGGAGTCTGGCGGCGGCCTGGTGCAGCCAGG CAGAAGCCTGAGACTGTCTTGTGCTGCCTCTGGCTTTTCCTTCGAC GATTACGCTATGCACTGGGTGCGGCAGGCTCCTGGCAAGGGCCTG GAGTGGGTGTCTGGCATCAGCTGGCACTCCGATAACATCGGCTAC GCTGATTCCGTGAAGGGCAGATTCACCATCTCCAGAGACAATGCCA AGAACTCCCTGTACCTGCAGATGAACTCCCTGAGAGCTGAGGATAC CGCCTTTTACTATTGCGCCAAGGATGGCCCAAGATATAGGGGCTCC TATTACTACTTCGACTATTGGGGCCAGGGCACACTGGTGACAGTCT CGAGT |
| 21046 VH SEQ ID NO: 2 | GAGGTGCAGCTGGTGGAGAGCGGCGGCGGCCTGGTGCAGCCTGG CAGATCTCTGAGACTGTCTTGCGTGGCTTCTGGTTTTACTTTTGATG ACTATGCCATGCACTGGGTGCGGCAGGCTCCAGGCAAGGGCCTGG AGTGGGTGTCTGGCATCAGCTGGAATTCCGGCTCTATCGGCTACG CTGACAGCGTGAAAGGCAGATTCACCATCTCCAGAGACAATGCCAA GAACAGCCTGTACCTGCAGATGAACTCCCTGAGAGCTGAGGATAC CGCTTTCTATTACTGCGCTCAGGGCGGCTATGCTATCCTGACCGCC CTGGAGTACTGGGGCCAGGGCACCCTGGTGACAGTCTCGAGT |
| 21127 VH SEQ ID NO: 3 | GAGGTGCAGCTGGTGGAGTCTGGCGGCGGCCTGGTGCAACCAGG CAGAAGCCTGAGACTGTCTTGTGCTGCCTCCGGTTTTACTTTCGAT GACTTCGCTATGCATTGGGTGCGGCAGGCCCCTGGCAAGGGCCTG GAGTGGGTGTCTGGCATCTCTTGGAATAGCGGCAACATCGGCTAC GCCGACTCTGTGAAGGGCAGATTCACCATCTCCAGAGACAACGCC AAGAACTCCCTGTATCTCCAAATGAACTCCCTGAGAGCTGAGGATA CCGCTCTGTACTATTGCGCCAAGGATAAGTCCGGCTCTCCTTACTA TTACTACGGCATGGACGTGTGGGGCCAGGGCACAATGGTGACCGT CTCGAGT |
| 21163 VH SEQ ID NO: 4 | GAGGTGCAGCTGGTGGAGTCTGGCGGCGGCCTGGTGCAGCCAGG CGGCTCCCTGAGACTGTCTTGTGCTGCCTCCGGCTTTAGCTTCTCC ACCTATTGGATGAACTGGGTGCGCCAGGCCCCAGGCAAGGGCCTG GAGTGGGTGGCCAATATCAAGCAGGATGGCTCCGAGAAGTACTAT GTGGACTCCGTGAAGGGCAGATTCACCATCTCCAGAGACAATGCC AAGAACTCCCTGTATCTGCAGATGAACTCCCTGAGAGCCGAGGATA CCGCCGTGTACTATTGTGCCAGGGATATCAGCTCCTCTTGGTTTTA CTATTACGGCATGGACGTGTGGGGCCAGGGCACAACCGTGACCGT CTCGAGT |
| 21028 VL SEQ ID NO: 5 | GACATCCAGATGACCCAGAGCCCTTCTACACTGTCCGCCAGCGTG GGCGATAGGGTGACCATCACATGCCGGGCCTCTCAGTCCATCAGC AACTGGCTGGCTTGGTACCAGCAGAAGCCCGGCAAGGCCCCTAAG CTGCTGATCTATAAGGCTTCCAGCCTGGAGAGCGGCGTGCCATCTA GATTCTCTGGCTCCGGCAGCGGCACCGAGTTTACCCTGACAATCTC TTCCCTGCAGCCAGACGATTTCGCTACATACTATTGTCAGCAGTAC AATTCTTATTCCCCCATCACCTTTGGCCAGGGCACACGCCTGGAGA TCAAG |
| 21046 VL SEQ ID NO: 6 | GACATCCAGATGACCCAGTCCCCTTCCAGCCTGTCCGCCTCCGTG GGCGATAGGGTGACCATCACATGCCGGGCCTCTCAGGGCATCTCC AACTACCTGGCTTGGTTCCAGCAGAAGCCCGGCAAGGCCCCTAAG AGCCTGATCTATGCCGCTTCTAGCCTGCAAAGCGGCGTGCCATCTA AGTTCTCTGGCTCCGGCAGCGGCACCGACTTTACCCTGACAATCAG CTCTCTGCAGCCAGAGGATTTCGCCACATACTATTGTCAGCAGTAC AATTCTTATCCCCTGACATTCGGCGGTGGAACTAAGGTGGAGATCA AG |
| 21127 VL SEQ ID NO: 7 | GACATCCAGATGACCCAGAGCCCCTCCTCCGTGTCCGCCTCCGTG GGCGATAGAGTGACCATCACATGCAGGGCTACACAGGGAATCTCT AGGCGGCTGGCTTGGTACCAGCAGAAGCCCGGCAAGGCCCCTAA GCTGCTGATCTATGCCGCTTCTAGCCTGCAATCTGGCGTGCCATCC AGGTTCTCTGGATCCGGAAGCGGAACCGACTTTACCCTGACAATCA GCTCTCTGCAGCCAGAGGATTTCGCCACATACTATTGTCAGCAGGC TAACTCCTTCCCCCTGACTTTCGGCGGTGGAACAAAAGTGGAGATC AAG |

TABLE 1-continued

Variable domain nucleotide sequences of
antibodies 21028, 21046, 21127 and 21163

| | Sequence (5' to 3') |
|---|---|
| 21163 VL<br>SEQ ID NO: 8 | GACATCCAGCTGACACAGAGCCCATCTTTCCTGTCCGCCTCCGTGG<br>GCGATAGGGTGACCATCACATGCCGGGCCTCTCAGGGCATCTCCA<br>GCTACCTGGCTTGGTATCAGCAGAAGCCAGGCAAGGCCCCCAAGC<br>TGCTGATCTACGCTGCTTCTACCCTGCAGTCCGGAGTGCCTAGCAG<br>GTTCTCTGGCTCCGGCAGCGGCACAGAGTTTACCCTGACAATCTCT<br>AGCCTGCAACCAGAGGACTTCGCCACCTACTATTGTCAGCAGCTGA<br>ACTCCTATCCCCCTACATTCGGCGGTGGAACCAAAGTCGAAATCAA<br>G |

Table 2 shows the deduced amino acid sequences of antibodies 21028, 21046, 21127 and 21163. CDRs are in bold/underlined.

TABLE 2

Variable domain amino acid sequences of
21028, 21046, 21127 and 21163

| | Sequence (N-terminal to C-terminal) |
|---|---|
| 21028 VH<br>SEQ ID NO: 9 | EVQLVESGGGLVQPGRSLRLSCAASGFSFDDYAMHWVRQAPGKGLE<br>WVSGISWHSDNIGYADSVKGRFTISRDNAKNSLYLQMNSLRAEDTAFY<br>YCAKDGPRYRGSYYYFDYWGQGTLVTVSS |
| 21046 VH<br>SEQ ID NO: 10 | EVQLVESGGGLVQPGRSLRLSCVASGFTFDDYAMHWVRQAPGKGLE<br>WVSGISWNSGSIGYADSVKGRFTISRDNAKNSLYLQMNSLRAEDTAFY<br>YCAQGGYAILTALEYWGQGTLVTVSS |
| 21127 VH<br>SEQ ID NO: 11 | EVQLVESGGGLVQPGRSLRLSCAASGFTFDDFAMHWVRQAPGKGLE<br>WVSGISWNSGNIGYADSVKGRFTISRDNAKNSLYLQMNSLRAEDTALY<br>YCAKDKSGSPYYYYGMDVWGQGTMVTVSS |
| 21163 VH<br>SEQ ID NO: 12 | EVQLVESGGGLVQPGGSLRLSCAASGFSFSTYWMNVVVRQAPGKGLE<br>VVVANIKQDGSEKYYVDSVKGRFTISRDNAKNSLYLQMNSLRAEDTAV<br>YYCARDISSSWFYYYGMDVWGQGTTVTVSS |
| 21028 VL<br>SEQ ID NO: 13 | DIQMTQSPSTLSASVGDRVTITCRASQSISNWLAWYQQKPGKAPKLLI<br>YKASSLESGVPSRFSGSGSGTEFTLTISSLQPDDFATYYCQQYNSYSP<br>ITFGQGTRLEIK |
| 21046 VL<br>SEQ ID NO: 14 | DIQMTQSPSSLSASVGDRVTITCRASQGISNYLAWFQQKPGKAPKSLIY<br>AASSLQSGVPSKFSGSGSGTDFTLTISSLQPEDFATYYCQQYNSYPLT<br>FGGGTKVEIK |
| 21127 VL<br>SEQ ID NO: 15 | DIQMTQSPSSVSASVGDRVTITCRATQGISRRLAWYQQKPGKAPKLLI<br>YAASSLQSGVPSRFSGSGSGTDFTLTISSLQPEDFATYYCQQANSFPL<br>TFGGGTKVEIK |
| 21163 VL<br>SEQ ID NO: 16 | DIQLTQSPSFLSASVGDRVTITCRASQGISSYLAWYQQKPGKAPKLLIY<br>AASTLQSGVPSRFSGSGSGTEFTLTISSLQPEDFATYYCQQLNSYPPT<br>FGGGTKVEIK |

Table 3 shows heavy and light chain constant region amino acid sequences (CH and CL, respectively). "IgG₁ LALA" refers to the presence of "LALA" mutations in the heavy chain (L234A/L235A, numbered according to the Kabat numbering scheme) that are known to reduce effector function of the Fc region of IgG₁ antibodies (Hezareh et al., *J Virol.* 75(24):12161-68 (2001); Hessell et al., *Nature* 449(7158):101-04 (2007)).

TABLE 3

Constant region amino acid sequences of
antibodies 21028, 21046, 21127 and 21163

| Fragment | Sequence (N-terminal to C-terminal) |
|---|---|
| IgG₁-LALA CH<br>added to the VH<br>SEQ ID NO: 41 | ASTKGPSVFPLAPSSKSTSGGTAALGCLVKDYFPEPVTVSWNSGALT<br>SGVHTFPAVLQSSGLYSLSSWTVPSSSLGTQTYICNVNHKPSNTKVD<br>KRVEPKSCDKTHTCPPCPAPEAAGGPSVFLFPPKPKDTLMISRTPEV<br>TCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPP |

TABLE 3-continued

Constant region amino acid sequences of
antibodies 21028, 21046, 21127 and 21163

| Fragment | Sequence (N-terminal to C-terminal) |
|---|---|
| | SREEMTKNQVSLTCLVKGFYPSDIAVEWESNGQPENNYKTTPPVLDS DGSFFLYSKLTVDKSRWQQGNVFSCSVMHEALHNHYTQKSLSLSPG K |
| Kappa CL added to the VL SEQ ID NO: 42 | RTVAAPSVFIFPPSDEQLKSGTASVVCLLNNFYPREAKVQWKVDNAL QSGNSQESVTEQDSKDSTYSLSSTLTLSKADYEKHKVYACEVTHQGL SSPVTKSFNRGEC |

Table 4 shows heavy and light chain CDR amino acid sequences of antibodies 21028, 21046, 21127, and 21163, wherein the CDRs are defined according to the IMGT system.

TABLE 4

CDR amino acid sequences of antibodies 21028, 21046, 21127 and 21163

Sequence (N-terminal to C-terminal)

| Name | H-CDR1 | H-CDR2 | H-CDR3 | L-CDR1 | L-CDR2 | L-CDR3 |
|---|---|---|---|---|---|---|
| 21028 | GFSFDDYA SID 17 | ISWHSDNI SID 18 | CAKDGPRYRGSYYYFDYW SID 19 | QSISNW SID 20 | KAS SID 21 | CQQYNSYSPITF SID 22 |
| 21046 | GFTFDDYA SID 23 | ISWNSGSI SID 24 | CAQGGYAILTALEYW SID 25 | QGISNY SID 26 | AAS SID 27 | CQQYNSYPLTF SID 28 |
| 21127 | GFTFDDFA SID 29 | ISWNSGNI SID 30 | CAKDKSGSPYYYYGMDVW SID 31 | QGISRR SID 32 | AAS SID 33 | CQQANSFPLTF SID 34 |
| 21163 | GFSFSTYW SID 35 | IKQDGSEK SID 36 | CARDISSSWFYYYGMDVW SID 37 | QGISSY SID 38 | AAS SID 39 | CQQLNSYPPTF SID 40 |

SID: SEQ ID NO:

Table 5 shows SEQ ID NO information for antibodies 21028, 21046, 21127 and 21163. Unless otherwise stated, the sequences are amino acid sequences.

TABLE 5

SEQ ID NOs for antibodies 21028, 21046, 21127 and 21163

| Name | VH nt | VL nt | VH aa | VL aa | H-CDR1 | H-CDR2 | H-CDR3 | L-CDR1 | L-CDR2 | L-CDR3 |
|---|---|---|---|---|---|---|---|---|---|---|
| 21028 | 1 | 5 | 9 | 13 | 17 | 18 | 19 | 20 | 21 | 22 |
| 21046 | 2 | 6 | 10 | 14 | 23 | 24 | 25 | 26 | 27 | 28 |
| 21127 | 3 | 7 | 11 | 15 | 29 | 30 | 31 | 32 | 33 | 34 |
| 21163 | 4 | 8 | 12 | 16 | 35 | 36 | 37 | 38 | 39 | 40 | nt: nucleotide
aa: amino acid

Example 2. Screening of Anti-CD73 Antibodies in Soluble CD73 Activity Assay

A panel of anti-CD73 antibodies was evaluated for the ability to inhibit the enzymatic activity of soluble recombinant CD73. Anti-CD73 antibodies were incubated at a concentration of 10 μg/mL with recombinant CD73 (Sino-Biological Incorporated), AMP, and ATP for 30 minutes at 37° C. CD73 activity was investigated by measuring AMP inhibition of ATP detection using CellTiter-Glo® 2.0 (Promega Corporation) as described in Sachsenmeier et al., *Journal of Biomolecular Screening* 17(7):993-998 (2012).

The inhibition of CD73 enzymatic activity after treatment with the anti-CD73 antibodies is seen in FIG. 1. It is evident that CD73 activity after treatment with the different anti-CD73 antibodies varied strongly, showing that some antibodies had no functionality in this assay, whereas other antibodies strongly inhibited CD73 activity.

Example 3. Screening of Anti-CD73 Antibodies in a Cell-Based CD73 Activity Assay A panel of anti-CD73 antibodies was evaluated for the ability to inhibit the activity of CD73 expressed on cancer cell lines. Anti-CD73 antibodies were incubated at a concentration of 10 μg/mL with CD73-expressing cell lines for 30 minutes at 37° C. followed by addition of the CD73 substrate, AMP, and additional incubation for 3 hours at 37° C. CD73 activity was investigated by adding ATP to supernatants and measuring AMP inhibition of ATP detection using CellTiter-Glo® 2.0 (Promega Corporation) as described in Sachsenmeier et al., supra.

Figure 2:
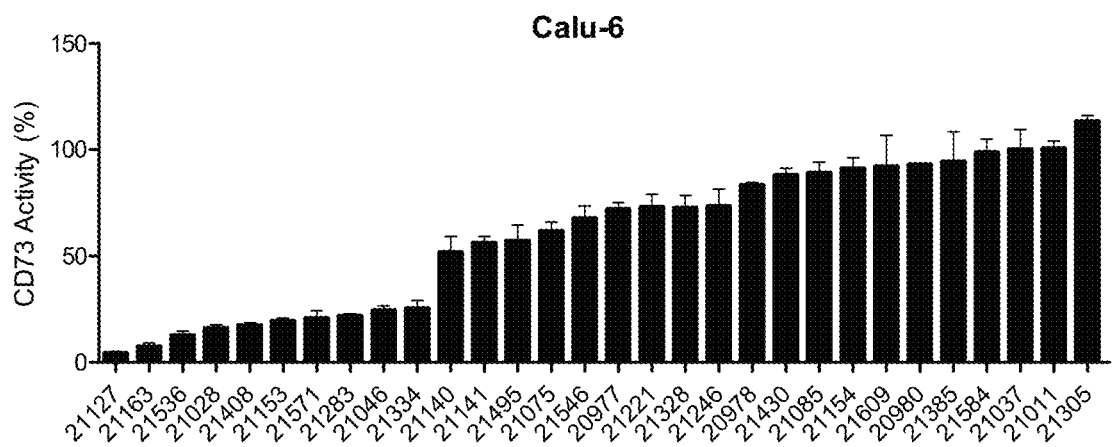
FIG. 2 is a pair of graphs showing the activity of CD73 expressed on Calu-6 cells (top) or H292 cells (bottom) after treatment with the indicated anti-CD73 antibodies. Data are normalized to untreated controls and presented as mean±SEM.
Figure 2:
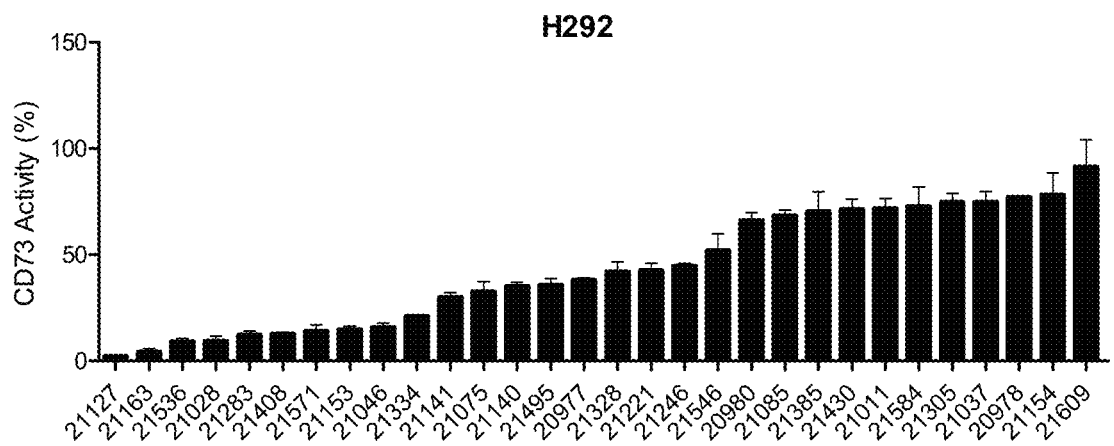

The activity of CD73 expressed on two different cancer cell lines after treatment with the anti-CD73 antibodies is shown in FIG. 2. It is evident that CD73 activity after treatment with the different anti-CD73 antibodies varied strongly; some antibodies had no functionality in this assay, whereas other antibodies strongly inhibited CD73 activity. Notably, the same ten antibodies showed the most activity in both cell lines.

Example 4. Cloning of Anti-CD73 Reference Antibody Analogues

Materials and Methods

The amino acid sequences encoding the heavy and light chain variable domains of the antibody analogues in Table 6 were obtained from the listed patents or patent applications. The protein sequences were reverse translated to DNA sequences with human codon usage. The corresponding DNA sequences were gene synthesized and cloned into expression vectors containing human heavy or light chain constant regions, resulting in expression of full-length antibody chains. The human antibody isotype selected for expression is listed in the antibody format column together with additional mutations introduced in the Fc region where applicable. CHO cells were transfected with the resulting expression plasmids using a standard protein expression system. The corresponding antibody supernatants were purified using standard protein A purification column chromatography.

TABLE 6

Listing of gene-synthesized antibody analogues and the corresponding antibody format

| Antibody | Antibody format | Source |
|---|---|---|
| MEDI9447 (oleclumab, Medimmune) | IgG$_1$-TM (effector-function attenuated triple mutant L234F, L235E and P331S) | U.S. Patent Publication 2016/0129108 A1 (SEQ ID NOs: 17 and 19) |
| CPX006 (Corvus) | IgG$_1$-N297Q (non-glycosylated) | U.S. Patent Publication 2018/0009899 A1 (SEQ ID NOs: 14 and 13) |
| 11E1 (Innate Pharma) | IgG$_1$-LALA | U.S. Patent Publication 2018/0030144 A1 (SEQ ID NOs: 3 and 4) |

Example 5. Direct Binding of Anti-CD73 Antibodies to CHO-S Cells Transfected with Human or Cynomolgus CD73 Protein The binding of anti-CD73 antibodies 21028, 21046, 21127, and 21163 to human or cynomolgus CD73 protein expressed on CHO-S cells was evaluated and compared to that of an oleclumab analogue.

The anti-CD73 antibodies were incubated with the hamster CHO-S cell line transiently expressing human or cynomolgus CD73 for 30 minutes at 4° C. The cells were washed twice and subsequently incubated for an additional 20 minutes with AF647-conjugated secondary anti-human IgG (H+L) antibody. After the washing step, antibody binding was detected using the high-throughput flow cytometer iQue Screener PLUS (Sartorius) measuring the GeoMean of AF647 signal in each well. Every concentration was assayed in triplicate and a 12-point titration curve was generated for each antibody.

Figure 3:
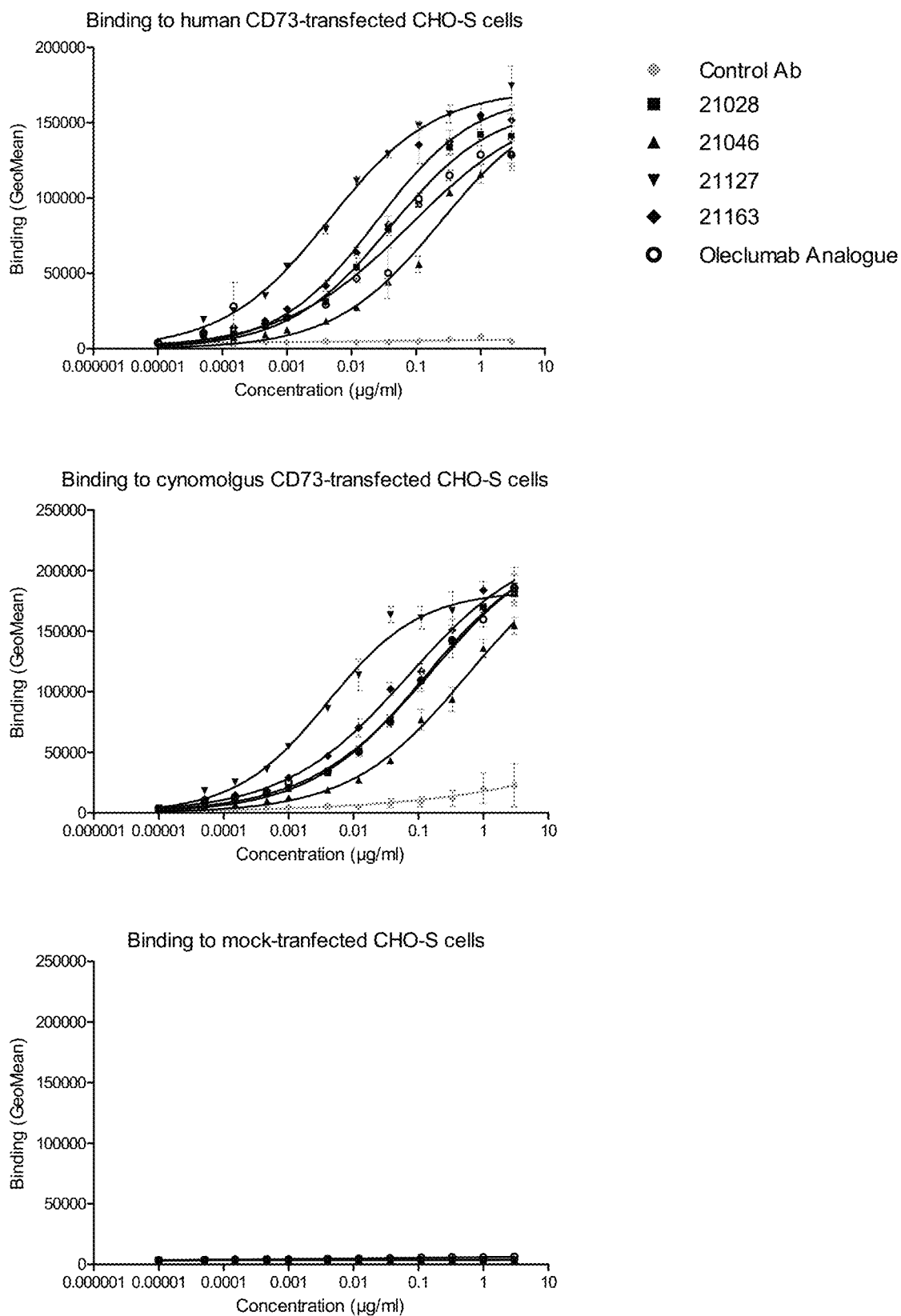
FIG. 3 is a set of graphs showing the binding of the indicated anti-CD73 antibodies and a reference antibody (oleclumab) analogue to human and cynomolgus CD73 expressed on CHO-S cells. Mock transfected CHO-S cells were used as a negative control. The "Control Ab" is a non-CD73-specific FcγR-deficient IgG$_1$-LALA isotype antibody. Data are presented as mean±SEM.

The binding curves of the antibodies to human or cynomolgus CD73 expressed on cells are shown in FIG. 3. The assayed antibodies bind to cell-displayed human and cynomolgus CD73 protein with differing potency and efficacy. In particular, mAb 21127 binds to human and cynomolgus CD73 with the highest potency of the antibodies tested.

Example 6. Measurement of Antibody and Fab Fragment Affinities for Human and Cynomolgus CD73 Extracellular Domain (ECD)

This example demonstrates the binding of anti-CD73 Fab fragments and antibodies to recombinant human and cynomolgus CD73 extracellular domains (ECDs) as measured by surface plasmon resonance (SPR).

Materials and Methods

Kinetic binding analysis of anti-CD73 mAbs and Fab fragments was performed by Surface Plasmon Resonance (SPR), using a Continuous Flow Microspotter (CFM, Wasatch Microfluidics, Salt Lake City, US) combined with an IBIS MX96 SPR instrument (IBIS Technologies, The Netherlands). CD73 cDNAs coding for the extracellular domains of human and cynomolgus CD73 were synthesized and each cloned into a vector containing a CMV promoter and either a C-terminal 6x histidine sequence (SEQ ID NO: 45) for His-tagged CD73 ECD, or a human IgG1 Fc sequence (AA P101-K330), resulting in fusion of IgG1 Fc C-terminally to the cloned CD73 ECD. The His-tagged and Fc-fusion constructs were transiently expressed using an ExpiCHO™ expression system and purified either by standard Ni-NTA chromatography or standard MabSelect™ SuRe™ procedures, respectively. Anti-CD73 Fab fragments were generated by digesting full-length IgG1 antibodies with GingisKHAN enzyme, using a kit provided by Genovis (Sweden). Affinities of Fab fragments were measured by capturing Fc-tagged antigens on a G-a-hu-IgG Fc SensEye® for 15 minutes using the CFM. After spotting, the SensEye® was positioned in the IBIS MX96 biosensor and immobilized antigens were fixed by SensEye FixIt kit. Kinetic analysis was performed by injecting monomeric Fab fragments at increasing concentrations from 0.8 nM to 300 nM. After each cycle of Fab fragment injection, the surface was regenerated by 10 mM glycine pH 3, 10% glycerol. Fab association was performed for 15 minutes and antigen dissociation was performed for 15 minutes. Affinities of full-length monoclonal antibodies (mAbs) were measured by capturing mAbs on a G-a-hu-IgG Fc SensEye® (Ssens BV, The Netherlands) for 15 minutes using a Continuous Flow Microspotter (CFM, Wasatch Microfluidics, Salt Lake City, US). After spotting, the SensEye was docked in the IBIS MX96 and spotted mAbs were fixed by SensEye FixIt kit (Ssens BV, The Netherlands). Kinetic analysis was performed by applying a kinetic titration series injecting increasing concentrations of His-tagged antigens from 0.16 nM to 10 nM as 2-fold dilutions. The surface was regenerated before the next cycle of cynomolgus antigen injections by 100 mM $H_3PO_4$, pH 3. MAb association was performed for 15 minutes and antigen dissociation was performed for 45 minutes. The recorded binding responses were fitted to a simple Langmuir 1:1 binding model with Scrubber 2.0 software for calculation of the on-rate ($k_{on}$ or $k_a$), off-rate ($k_{off}$ or $k_d$) and affinity ($K_D$) constants. Binding kinetic parameters were measured as an average of six independent measuring points.

Results

The binding affinities and kinetic parameters of the anti-CD73 Fab fragments and full-length antibodies are shown in Table 7 and Table 8, respectively. The full-length antibodies bound human CD73 with high affinities in the sub-nanomolar range. All antibodies recognized human and cynomolgus CD73 with comparable binding kinetics to the reference antibodies (analogues of 11E1, oleclumab, and CPX006). All antibodies were characterized by very slow dissociation rate constants, contributing to the high affinities measured. The monovalent binding affinities of the Fab fragments were 20 to 245 times weaker than those of the corresponding full-length antibodies. Dissociation rates (kd) were strongly affected by the change in format, with the Fab fragments displaying much faster dissociation from CD73 than the intact antibodies.

The differences in binding kinetics of intact antibodies and Fab fragments suggest that the antibodies bind a CD73 homodimer and that the high affinity measured for the full-length antibodies is due to avidity effects. CD73 is known to exist as a non-covalent homodimer (Knapp et al., Structure 20(12): 2161-2173 (2012)), and binding of the 11E1 and oleclumab analogues has previously been found to depend on bivalent binding to the CD73 homodimer with similar differences in binding kinetics between the full-length antibodies and Fab fragments as described here (Perrot, *Cell Reports* 27(8):2411-2425 (2019)).

The SPR analysis of the anti-CD73 antibodies and Fab fragments showed that anti-CD73 antibodies depend on bivalent binding to dimeric CD73, and that the binding affinities of the full-length antibodies exemplified herein were comparable to those of the reference mAbs when binding to a CD73 homodimer.

TABLE 7

Binding kinetics of anti-CD73 Fab fragments to human (Hs) and cynomolgus (Cy) CD73 ECD as measured by SPR

| Fab fragment | CD73 ECD | $K_a$ (M$^{-1}$ s$^{-1}$) | kd (s$^{-1}$) | $K_D$ (nM) |
|---|---|---|---|---|
| 21127 | Hs | 2.9E+05 | 1.6E-02 | 54.6 |
|  | Cy | 3.1E+05 | 1.7E-02 | 55.3 |
| 21163 | Hs | 2.0E+05 | 1.5E-02 | 78.3 |
|  | Cy | 2.0E+05 | 1.6E-02 | 77.6 |
| 21046 | Hs | 6.1E+05 | 5.0E-04 | 0.8 |
|  | Cy | 6.2E+05 | 5.2E-04 | 0.8 |
| 11E1 analogue | Hs | 2.9E+05 | 2.8E-03 | 9.8 |
|  | Cy | 3.2E+05 | 2.8E-03 | 8.7 |
| Oleclumab analogue | Hs | 5.6E+05 | 3.4E-05 | 0.06 |
|  | Cy | 5.8E+05 | 4.3E-05 | 0.07 |
| CPX006 analogue | Hs | 6.6E+03 | 5.3E-04 | 80.3 |
|  | Cy | 6.7E+03 | 4.8E-04 | 71.6 |

TABLE 8

Binding kinetics of anti-CD73 antibodies to human (Hs) and cynomolgus (Cy) CD73 ECD as measured by SPR

| mAb | CD73 ECD | $K_a$ (M$^{-1}$ s$^{-1}$) | kd (s$^{-1}$) | $K_D$ (nM) |
|---|---|---|---|---|
| 21127 | Hs | 3.2E+05 | 7.0E-05 | 0.22 |
|  | Cy | 3.8E+05 | 9.0E-05 | 0.24 |
| 21163 | Hs | 6.5E+04 | 5.5E-05 | 0.91 |
|  | Cy | 1.0E+05 | 6.2E-05 | 0.66 |
| 21046 | Hs | 1.9E+05 | 8.3E-06 | 0.04 |
|  | Cy | 2.1E+05 | 1.1E-05 | 0.05 |
| 11E1 analogue | Hs | 5.7E+04 | 5.6E-06 | 0.10 |
|  | Cy | 8.4E+04 | 1.3E-05 | 0.14 |
| Oleclumab analogue | Hs | 1.1E+05 | 2.5E-06 | 0.02 |
|  | Cy | 1.4E+05 | 6.6E-06 | 0.06 |
| CPX006 analogue | Hs | 1.7E+05 | 2.4E-06 | 0.02 |
|  | Cy | 2.8E+04 | 1.4E-05 | 0.33 |

Example 7. Epitope Binning of Anti-CD73 Antibodies

Figure 4:
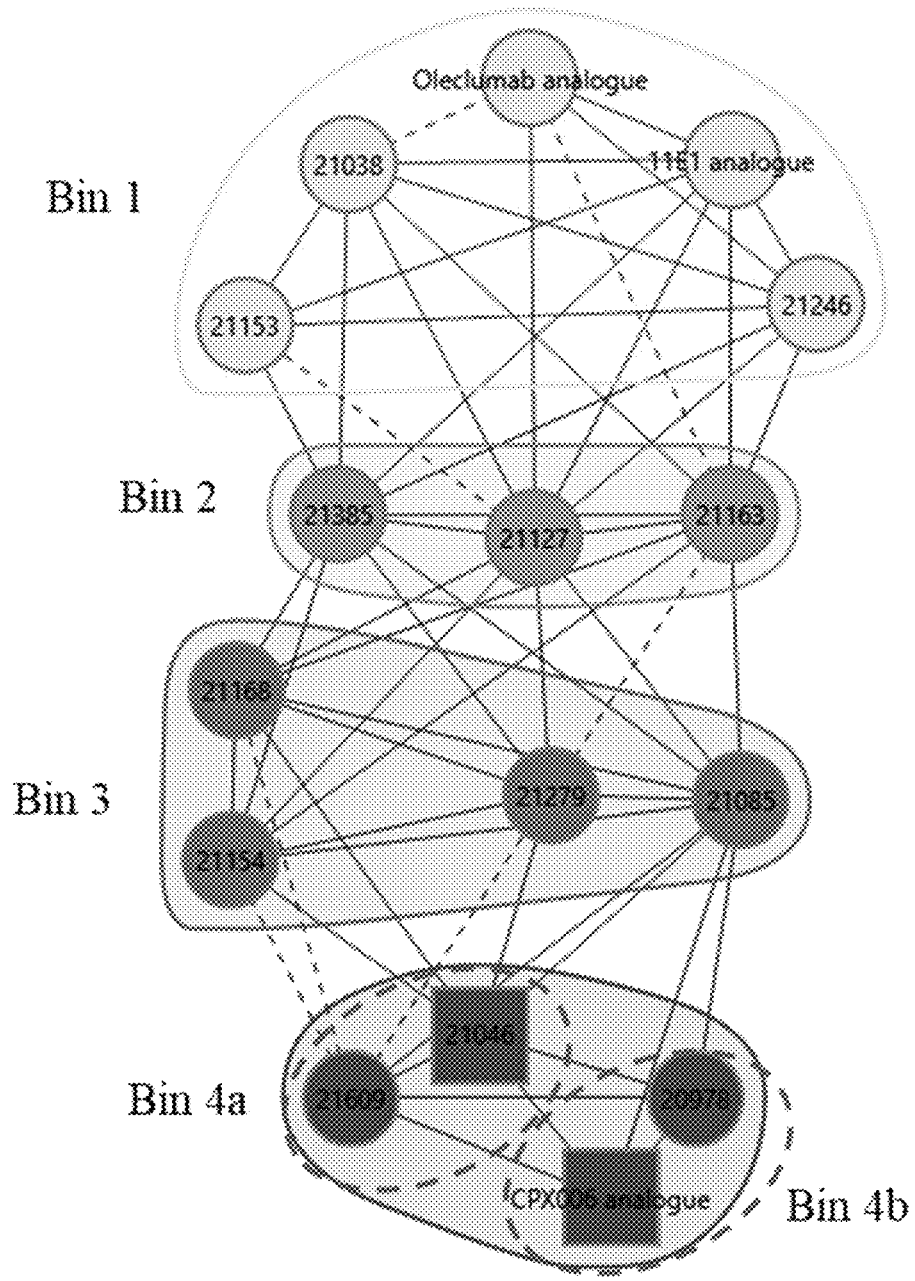
FIG. 4 is a schematic showing competition patterns and epitope bins identified for the indicated anti-CD73 antibodies. Connecting black lines indicate cross-blocking activity. Connecting dotted lines indicate antibodies that only block in one direction. Antibodies are grouped according to competition patterns with other anti-CD73 antibodies.

This example describes the grouping of anti-CD73 antibodies into epitope bins based on paired competition patterns. Antibodies belonging to different epitope bins recognize different epitopes on the ECD of CD73.
Materials and Methods Investigation of paired antibody competition was performed by SPR using an IBIS-MX96 instrument (IBIS, Netherlands). Anti-CD73 antibodies were diluted to 3 µg/mL in PBS and spotted onto a G-a-hu-IgG Fc SensEye® by capturing for 15 minutes using a Continuous Flow Microspotter, followed by blocking of residual binding sites by Herceptin (trastuzumab) and chemical cross-linking by SensEye FixIt kit (IBIS, Netherlands). After sensor preparation, antibody competition analysis was performed using a classical sandwich assay. CD73-His ECD antigen was diluted in PBS, 0.05% Tween 20, and 200 nM Herceptin running buffer, then injected at a 10 nM concentration and captured by the conjugated array of anti-CD73 antibodies. Next, individual injections of each of the CD73 antibodies diluted to 100 nM in running buffer were performed to establish antibody competition patterns. Data was analyzed by Epitope Binning 2.0 (Wasatch, USA).
Results The competition pattern of 16 anti-CD73 antibodies is presented in FIG. 4. The tested anti-CD73 antibodies group in four overlapping main epitope bins: 1, 2, 3, and 4. Bin 1 included the oleclumab and 11E1 analogues, which cross-blocked each other. Oleclumab and the 11E1 antibody have been shown to bind overlapping epitopes at the top of the N-terminal domain and opposite to the catalytic site of CD73 (Geoghegan et al., *MABS* 8(3):454-467 (2016), and Perrot et al., *Cell Reports* 27:2411-2425 (2019)). All antibodies in bin 1 cross-blocked the antibodies grouped in bin 2. Bin 2 included antibodies 21385, 21127, and 21163, which displayed comparable competition patterns, suggesting that the antibodies bind similar epitopes. The antibodies in bin 2 cross-blocked all the tested antibodies except antibodies in bin 4. The bin 4 antibodies could be divided into two sub-bins; bin 4a and 4b competing with one or more antibodies in bin 3. Antibody 21046 (bin 4a) and the CPX006 analogue (bin 4b) competed with different antibodies in bin 3, showing that the two antibodies have closely related but not identical binding epitopes.

In conclusion, antibodies 21127 and 21163 (bin 2) bind unique epitope(s) of CD73 that have some overlap with the epitope(s) of the 11E1 and oleclumab analogues (bin 1). The epitope(s) of antibodies 21127 and 21163 are distinct from that of the CPX006 analogue (bin 4). Antibody 21046 (bin 4a) binds an epitope that is similar to the CPX006 analogue epitope (bin 4b), but different from the epitopes of antibodies 21127 and 21163 (bin 2) and the 11E1 and oleclumab analogues (bin 1).

Example 8. Epitope Mapping of Anti-CD73 Antibodies by CD73 Mutagenesis

This example illustrates how the binding epitopes of antibodies 21127, 21163, and 21046 can be divided into linear epitopes and individual contact residues by measuring binding affinity and kinetics to 94 different CD73 mutants.
Materials and Methods The protein sequences of human and rat (*Rattus norvegicus*) CD73 were downloaded from UniProt (Accession Nos. P21589 and P21588, respectively). The full-length protein sequences of cynomolgus monkey (*Macaca fascicularis*) and chicken (*Gallus gallus*) CD73 were downloaded from NCBI (XP_005552488.1, and XP 004940453.1, respectively). The publicly available CD73 structures PDB 4H2F (open), 4H2G (open), and 4H2I (closed) were used to map surface-exposed amino acid residues. Surface-exposed residue positions that differed between human and rat CD73 were mutated to alanine. To map linear antibody epitopes, CD73 chimeric proteins were generated in which 10 amino acids in the human CD73 ECD sequence were sequentially exchanged to chicken sequence in segments that overlapped by 5 amino acids.

The cDNA coding for the extracellular domain of human CD73 was synthesized and cloned into a vector containing CMV promoter and human Ig Fc sequence (residues P101-K330), resulting in fusion of Ig Fc C-terminally to the cloned CD73 ECD. Wild type (wt) and mutated human CD73 Fc fusion constructs were generated by standard gene synthesis techniques and proteins were expressed transiently in 2 mL cultures using an ExpiCHO™ expression system.

After the human CD73 Fc fusion constructs were harvested, supernatants were tested for binding to anti-CD73 Fabs by Surface Plasmon Resonance (SPR). Culture supernatants containing CD73 fusion proteins were immobilized onto a G-a-hu-IgG Fc SensEye® (Ssens BV, The Netherlands) for 15 minutes using a Continuous Flow Microspotter (CFM, Wasatch Microfluidics, Salt Lake City, US). After spotting, the SensEye® was positioned in an IBIS MX96 biosensor and captured proteins were fixed to the surface using FixIT kit (Ssens BV, The Netherlands). Kinetic analysis was performed by applying kinetic titration series where monomeric Fab fragments of the antibodies of the invention were injected in increasing concentrations from 0.8 nM up to 500 nM. After each cycle of Fab fragment injection, the surface was regenerated by 10 mM glycine pH 3, 10% glycerol. Fab association was performed for 15 minutes and antigen dissociation was performed for 15 minutes. The recorded binding responses were fitted to a simple Langmuir 1:1 binding model with Scrubber 2 software for calculation of the on-rate ($k_{on}$ or $k_a$), off-rate ($k_{off}$ or $k_d$) and affinity ($K_D$) constants.

Results

The epitopes of CD73 recognized by antibodies 21127, 21163 and 21046, and the 11E1, oleclumab, and CPX006 analogues were mapped using chimeric receptor constructs, in which 10-amino acid segments of the human CD73 sequence were replaced with chicken sequence; or by alanine scanning, where surface exposed amino acids that differed between human and rat CD73 were mutated to alanine. The binding affinities of the antibodies for wild-type CD73 and mutants were measured by SPR, and a cutoff of at least 5-fold affinity reduction compared to wt or deviation from the 1:1 binding model were used for finding constructs with significant loss of binding to anti-CD73 antibodies (Table 9).

TABLE 9

Summary of binding specificities of antibodies 21127, 21163, and 21046, and the 11E1, oleclumab, and CPX006 analogues

| Antibody | Linear Epitopes | Contact Residues |
| --- | --- | --- |
| 21127 | 27-31, 61-75, 161-170 | R73, R109, D168 |
| 21163 | 61-70, 161-170 | R109 |
| 21046 | 27-31, 266-270, 291-305 | I301, S302, H304 |
| 11E1 Analogue | 126-135, 156-170 | E129, K133, E134 |
| Oleclumab Analogue | 161-170, 206-215 | V170, K206, N211 |
| CPX006 Analogue | 206-210, 231-235, 266-270, 296-305 | R297, I301 |

Figure 5:
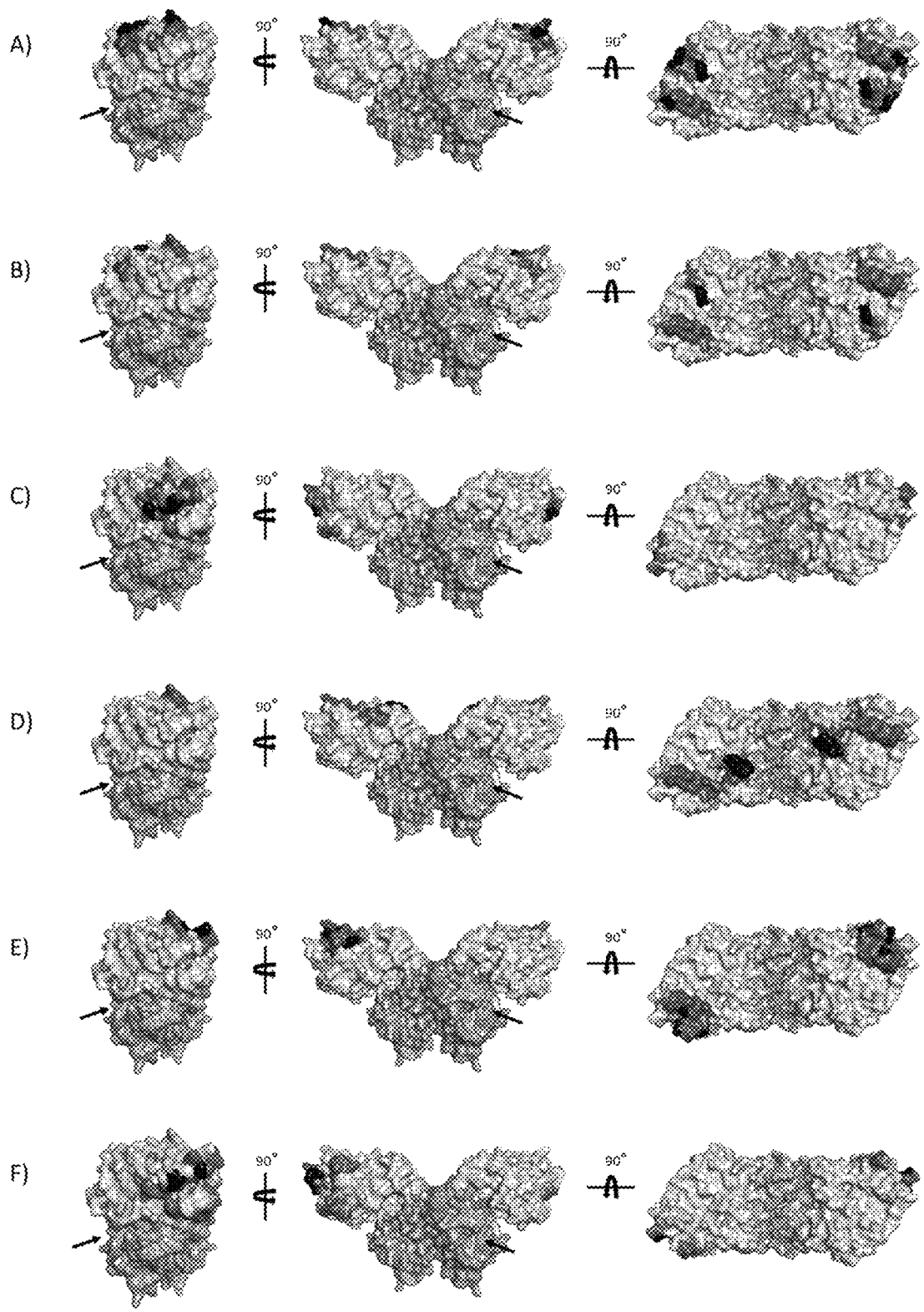
FIG. 5 depicts the binding epitopes of antibodies 21127 (panel A), 21163 (panel B), 21046 (panel C), 11E1 analogue (panel D), oleclumab analogue (panel E), and CPX006 analogue (panel F) mapped on the crystal structure of CD73 dimer (4H2G) in its open state. The structures are shown as a surface representation, with the N-terminal domain as light gray and the C-terminal domain as gray. Adenosine is shown as sticks in white (indicated by arrows). Linear epitopes are shown as dark gray and contact residues as black.

The identified linear epitopes and contact residues were mapped on the crystal structure of the CD73 homodimer in its open state (FIG. 5). The epitopes recognized by antibodies 21127, 21163, and 21046, and the 11E1, oleclumab, and CPX006 analogues were all found to be on the N-terminal domain of CD73 (FIG. 5). The epitopes of antibodies 21127 and 21163 and the 11E1 and oleclumab analogues were found to be located on a surface perpendicular to the dimerization interface of the CD73 homodimer and on the opposite side relative to the catalytic center (FIG. 5, panels A, B, D, and E). The epitopes of the four antibodies were found to be distinct by binding different contact residues and linear epitopes. Antibodies binding to the surface on top of CD73 may block enzyme activity by locking the enzyme in an open, inactive conformation, preventing the transition to the closed active state (Perrot et al., Cell Reports 27:2411-2425 (2019)).

The epitopes of antibody 21046 and the CPX006 analogue were found to be on the front of the N-terminal domain, just above the catalytic center of CD73 (FIG. 5, panels C and F). The two antibodies differ in terms of linear epitopes and contact residues recognized.

In summary, epitope mapping at single amino acid resolution showed that the exemplified anti-CD73 antibodies each have distinct binding epitopes. Antibodies 21127 and 21163 bind to similar epitopes on top of the CD73 N-terminal domain; these epitopes are distinct from the epitopes of the 11E1, oleclumab and CPX006 analogues. Antibody 21046 and the CPX006 analogue bind overlapping, but still distinct, epitopes on the front of the CD73 N-terminal domain.

Example 9. Stoichiometry of Antibody/CD73 Complexes Formed in Solution

This example describes the size of antibody/CD73 ECD complexes formed in solution as measured by SEC-MALS.

Materials and Methods

Anti-CD73 antibodies and His-tagged CD73 were analyzed in different ratios as well as individually to analyze the size of complexes formed between CD73 homodimer and anti-CD73 antibodies. Samples were prepared by mixing 900 μmol of CD73-His with 900, 450, 90 or 0 μmol of antibody diluted into PBS, pH 7.4. Samples were incubated for 30 min at room temperature followed by separation using a UHPLC UltiMate 3000 (Thermo Scientific) and SEC X-Bridge column (Waters) at a flow rate of 1.2 mL/min. Sample running buffer was 0.01 M Citrate, 250 mM L-Arginine.HCl, pH 6.0. Following HPLC separation, all samples were analyzed using a MiniDAWN TREOS MALS detector (Wyatt) and Optilab T-rEX refractive index detector (Wyatt). Data plots were generated using Graph Pad Prism.

Results

Figure 6A:
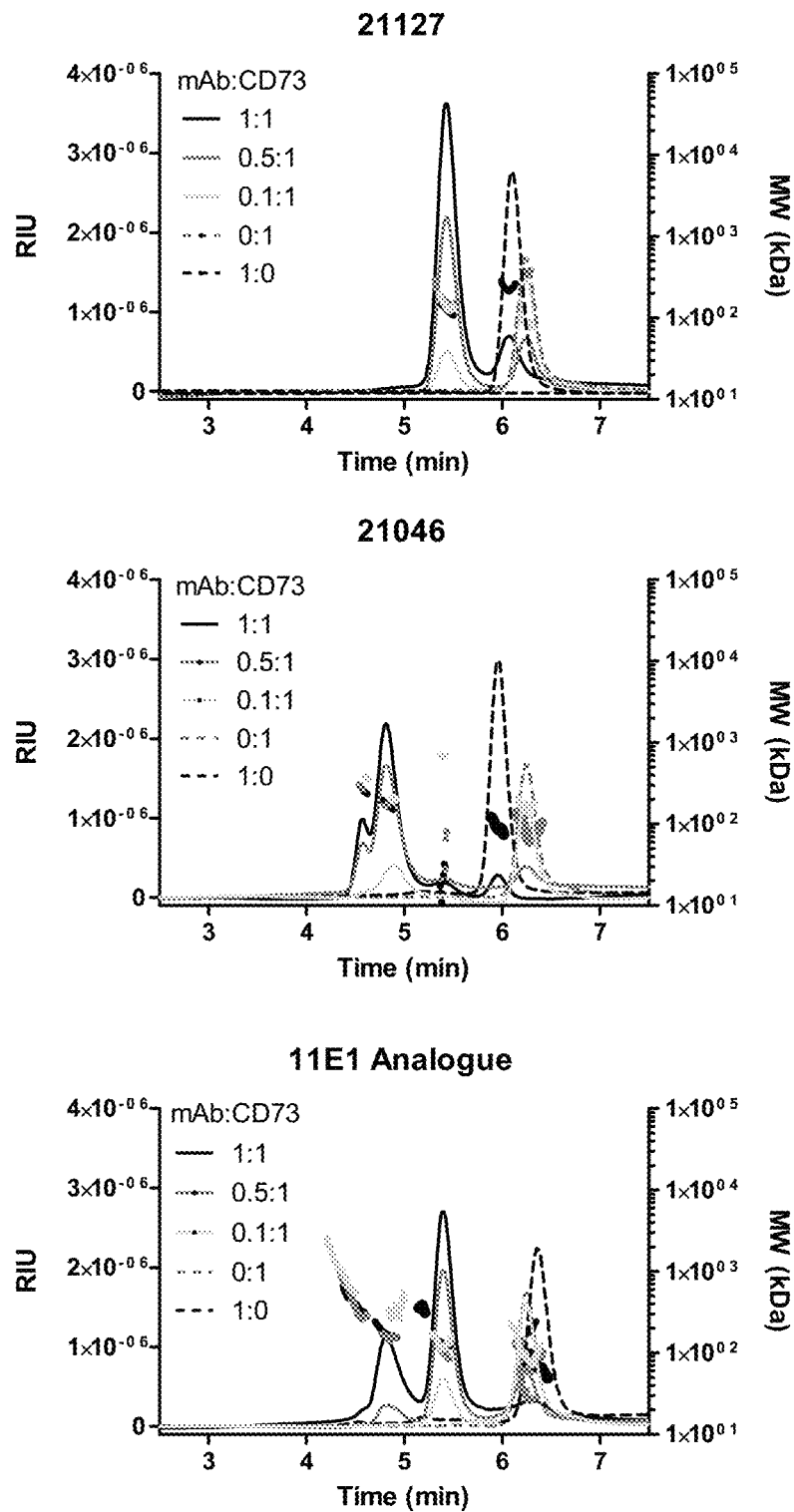
FIGS. 6A and 6B are a series of SEC-MALS profiles of antibodies 21127, 21163, 21046, and 11E1, oleclumab, and CPX006 analogues mixed with CD73 in the ratios mAb:CD73 1:1 (black lines), 0.5:1 (dark grey lines), 0.1:1 (light grey lines), 0:1 (grey dashed lines) and 1:0 (black dashed lines). The calculated sizes of the different peaks are shown in Table 10.
Figure 6B:
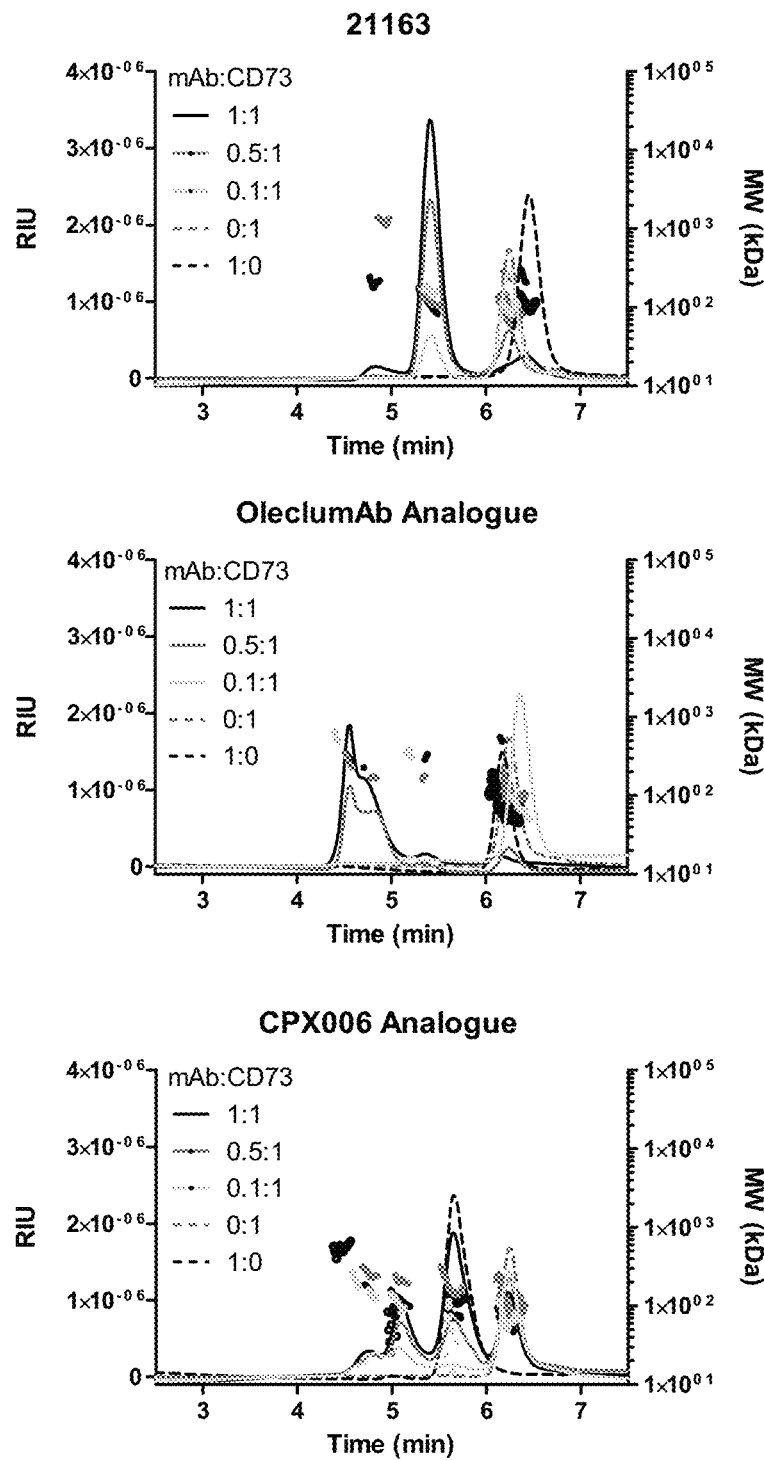

Bivalent binding of antibodies to the CD73 homodimer can lock the enzyme in an inactive conformation (Geoghegan et al., MABS 8(3):454-467 (2016) and Perrot et al., Cell Reports 27:2411-2425 (2019)). The blocking mechanism can be through cross-linking of CD73 homodimers or by binding a single CD73 dimer in the inactive state. To characterize the stoichiometry of antibody/CD73 complexes formed in solution, the sizes of the protein complexes were determined by SEC-MALS. The size of a 1:1 antibody/CD73 homodimer complex is in the range of 270-280 kDa, as calculated from the individual molecular weights of antibody and CD73 homodimer (approximately 150 and 125 kDa, respectively). FIGS. 6A and 6B and Table 10 show the SEC-MALS profiles and the sizes of formed complexes for antibodies 21127, 21163, and 21046 and the 11E1, oleclumab, and CPX006 analogues binding to the CD73 homodimer at various molecular ratios. The individual runs of CD73 and each of the antibodies show a monodisperse peak matching the expected sizes for the proteins, and confirm the absence of aggregates (FIGS. 6A and 6B, dashed lines). The SEC-MALS profile of antibody 21127 binding to CD73 shows one main peak (peak 2) with an average size of 276 kDa, corresponding to the size of the predicted 1:1 21127:CD73 homodimer complex, and one smaller peak (peak 1) corresponding to either excess of 21127 or CD73 dimers. Antibody 21163, and the 11E1 and CPX006 analogues, mainly formed 1:1 complexes but tended to form higher-order complexes at the highest antibody:CD73 ratio (1:1). Polydisperse higher-order complexes were most pronounced for the CPX006 and 11E1 analogues. Antibody 21046 and the oleclumab analogue formed large complexes, indicating that these antibodies mainly cross-link separate CD73 dimers, which has also been shown for oleclumab (MED19447) (Geoghegan et al, *MABS* 8(3):454-467 (2016)).

TABLE 10

Molecular masses (MW, kDa) of complexes formed when mixing CD73 and anti-CD73 antibodies at various ratios as measured by SEC-MALS

| Protein | Ratio mAb:CD73 (n:n) | Peak 1 (MW, kDa) | Peak 2 (MW, kDa) | Peak 3 (MW, kDa) | Peak 4 (MW, kDa) |
|---|---|---|---|---|---|
| CD73 | 0:1 | 124 | — | — | — |
| antibody | 1:0 | 151 | — | — | — |
| 21127 | 1:1 | 144 | 269 | — | — |
|  | 0.5:1 | 140 | 277 | — | — |
|  | 0.1:1 | 128 | 282 | — | — |
| 21163 | 1:1 | 197 | 280 | 606 | — |
|  | 0.5:1 | 143 | 278 | 464 | — |
|  | 0.1:1 | 129 | 279 | — | — |
| 21046 | 1:1 | 194 | 382 | 552 | 863 |
|  | 0.5:1 | 97 | 199 | 521 | 794 |
|  | 0.1:1 | 137 | 969 | 480 | 815 |
| 11E1 Analogue | 1:1 | 116 | 270 | 511 | 802 |
|  | 0.5:1 | 127 | 277 | 566 | 3372 |
|  | 0.1:1 | 123 | 265 | 704 | 11848 |
| Oleclumab Analogue | 1:1 | 116 | 389 | 682 | 1039 |
|  | 0.5:1 | 127 | 870 | 559 | 1007 |
|  | 0.1:1 | 123 | 194 | 432 | 821 |
| CPX006e Analogue | 1:1 | 124 | 148 | 246 | 363 |
|  | 0.5:1 | 118 | 143 | 245 | 349 |
|  | 0.1:1 | 120 | 121 | 236 | 339 |

The peaks in Table 10 correspond to peaks 1-4 seen on the chromatograms in FIGS. 6A and 6B as counted from right to left. Peak 1 corresponds to either unbound/excess CD73 homodimer (~125 kDa) or unbound/excess antibody (~150 kDa). Peaks 2-4 correspond to mAb:CD73 complexes of various size and stoichiometry, where a complex size of ~275 kDa represents a 1:1 stoichiometry.

As shown in Table 10 and FIGS. 6A and 6B, antibody 21127 binds an epitope on the CD73 homodimer in a manner that gives rise to a 1:1 complex, independent of CD73 concentration. Antibody 21163 and the 11E1 and CPX006 analogues primarily bind the CD73 dimer as a 1:1 complex, but also show a tendency to form higher-order complexes at various degrees. Antibody 21046 and the oleclumab analogue bind CD73 homodimer solely as oligomer complexes, indicating cross-linking of multiple CD73 dimers.

Example 10. Functionality of Anti-CD73 Antibodies in a Soluble CD73 Activity Assay The ability of anti-CD73 antibodies 21028, 21046, 21127, and 21163 to inhibit the enzymatic activity of soluble recombinant CD73 was evaluated in more detail and compared to an oleclumab analogue in a soluble CD73 activity assay. Anti-CD73 antibodies were incubated with recombinant CD73, AMP and ATP for 2 hours at 37° C. CD73 activity was investigated by measuring AMP inhibition of ATP detection using CellTiter-Glo® 2.0 (Promega Corporation) as described in Sachsenmeier et al., supra.

Figure 7:
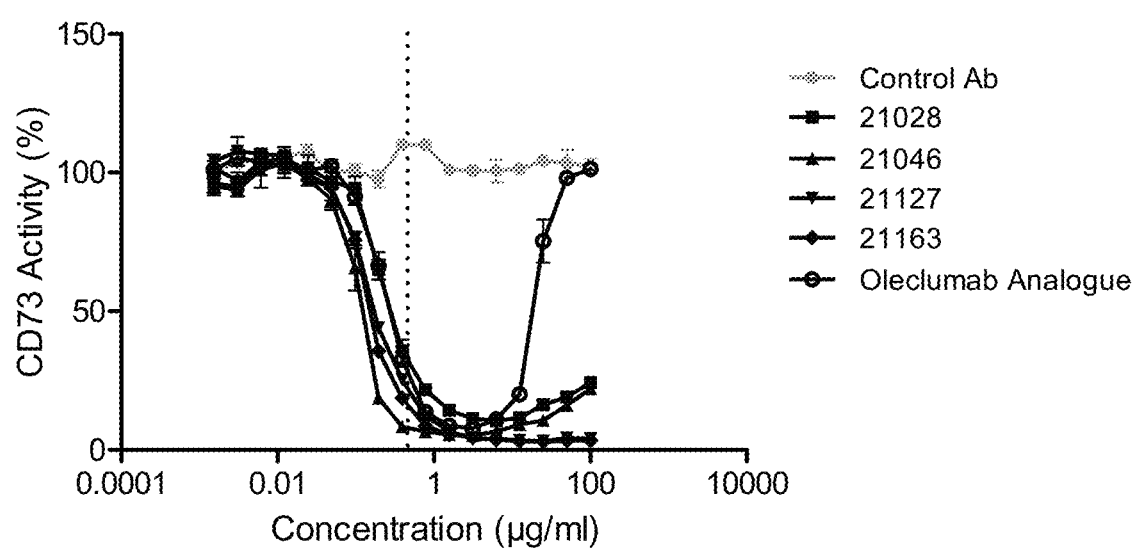
FIG. 7 is a graph showing the activity of soluble CD73 after treatment with the indicated anti-CD73 antibodies and a reference antibody (oleclumab) analogue. The "Control Ab" is a non-CD73-specific FcγR-deficient IgG$_1$-LALA isotype antibody. Data are normalized to untreated controls and presented as mean±SEM. The vertical dotted line indicates the antibody concentration that is equimolar to that of the soluble recombinant CD73.

The inhibition of CD73 enzymatic activity after treatment with the indicated concentrations of the anti-CD73 antibodies or the oleclumab analogue is shown in FIG. 7. It is evident that the inhibitory function of anti-CD73 antibodies is concentration dependent and that all of the anti-CD73 antibodies inhibit CD73 activity, albeit with differing potency and efficacy. Furthermore, the oleclumab analogue inhibits CD73 enzymatic activity less effectively at higher antibody concentrations. Similar results have been published for oleclumab (previously MED19447) by MedImmune (Geoghegan et al., *MABS* 8(3):454-467 (2016)). Antibodies 21028 and 21046 also inhibit CD73 enzymatic activity slightly less at higher concentrations as compared to intermediate concentrations. By contrast, antibodies 21127 and 21163 show maximum inhibition of CD73 enzymatic activity at all concentrations above approximately 3 µg/mL.

Example 11. Functionality of Anti-CD73 Antibodies in Cell-Based CD73 Activity Assays The ability of anti-CD73 antibodies 21028, 21046, 21127, and 21163 to inhibit the activity of CD73 expressed on cells was evaluated in more detail and compared to an oleclumab analogue. The anti-CD73 antibodies were incubated with CD73-expressing human cell lines (Calu-6 and H292) or a CD73-expressing cynomolgus cell line (Cynom-K1) for 30 minutes at 37° C. followed by addition of the CD73 substrate, AMP, and additional incubation for 3 hours at 37° C. CD73 activity was investigated by adding ATP to supernatants and measuring AMP inhibition of ATP detection using CellTiter-Glo® 2.0 (Promega Corporation) as described in Sachsenmeier et al., supra.

Figure 8:
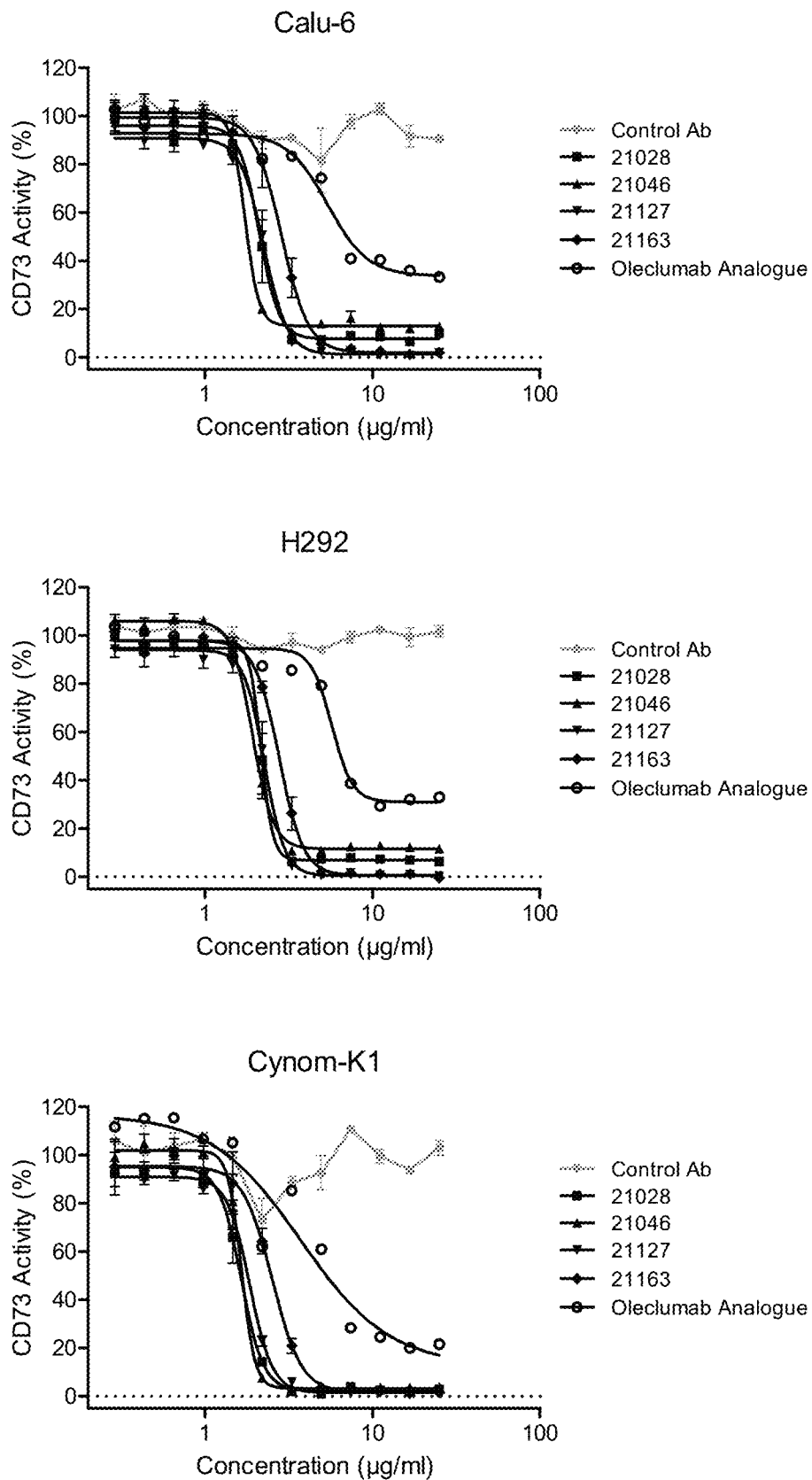
FIG. 8 is a set of graphs showing the activity of CD73 expressed on Calu-6 cells (top), H292 cells (middle), and Cynom-K1 cells (bottom) after treatment with the indicated anti-CD73 antibodies and a reference antibody (oleclumab) analogue. The "Control Ab" is a non-CD73-specific FcγR-deficient IgG$_1$-LALA isotype antibody. Data are normalized to untreated controls and presented as mean±SEM.

The inhibition of CD73 activity after treatment with the different anti-CD73 antibodies is shown in FIG. 8. It is evident that the inhibitory function of the anti-CD73 antibodies is concentration dependent and that all of the antibodies inhibit both human and cynomolgus CD73 activity, albeit with differing potency and efficacy. Antibodies 21127 and 21163 show the highest efficacy in the two human cell lines Calu-6 and H292, but all four tested antibodies are clearly superior to the oleclumab analogue in all three cell lines.

Example 12. Functionality of Anti-CD73 Antibodies in a Long-Term Cell-Based CD73 Activity Assay The ability of anti-CD73 antibodies 21028, 21046, 21127, and 21163 to inhibit the activity of CD73 expressed on cell lines was evaluated in more detail and compared to an oleclumab analogue in a long-term cell-based assay. The anti-CD73 antibodies were incubated with the CD73-expressing human cell line H292 for 30 minutes at 37° C. followed by addition of the CD73 substrate, AMP, and additional incubation for 3, 6 or 24 hours at 37° C. CD73 activity was investigated by adding ATP to supernatants and measuring AMP inhibition of ATP detection using CellTiter-Glo® 2.0 (Promega Corporation) as described in Sachsenmeier et al., supra.

Figure 9:
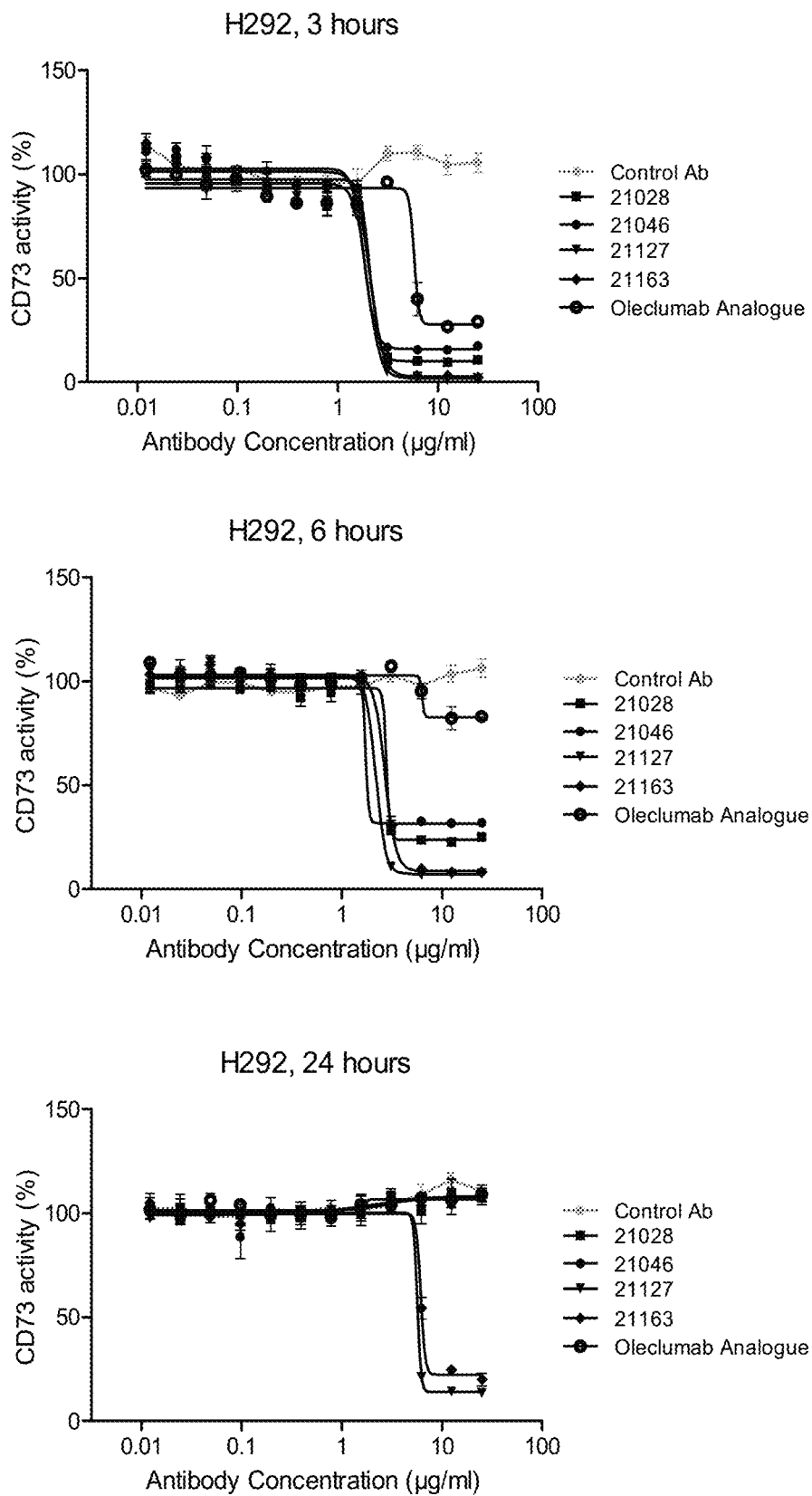
FIG. 9 is a set of graphs showing the activity of CD73 expressed on H292 cells after treatment with the indicated anti-CD73 antibodies and a reference antibody analogue (oleclumab) for 3 hours (top), 6 hours (middle), or 24 hours (bottom). Data are normalized to untreated controls and presented as mean±SEM.

The inhibition of CD73 activity after treatment with the different anti-CD73 antibodies is shown in FIG. 9. It is evident that the inhibitory function of anti-CD73 antibodies is concentration dependent and that all of the antibodies inhibit CD73 activity, albeit with differing potency and efficacy. Notably, incubating the cells with the antibodies for up to 24 hours further differentiates antibodies 21127 and 21163 from the oleclumab analogue (and from the other two anti-CD73 antibodies tested).

Example 13. Efficacy of Anti-CD73 Antibodies on Cancer Cell Lines

Figure 10:
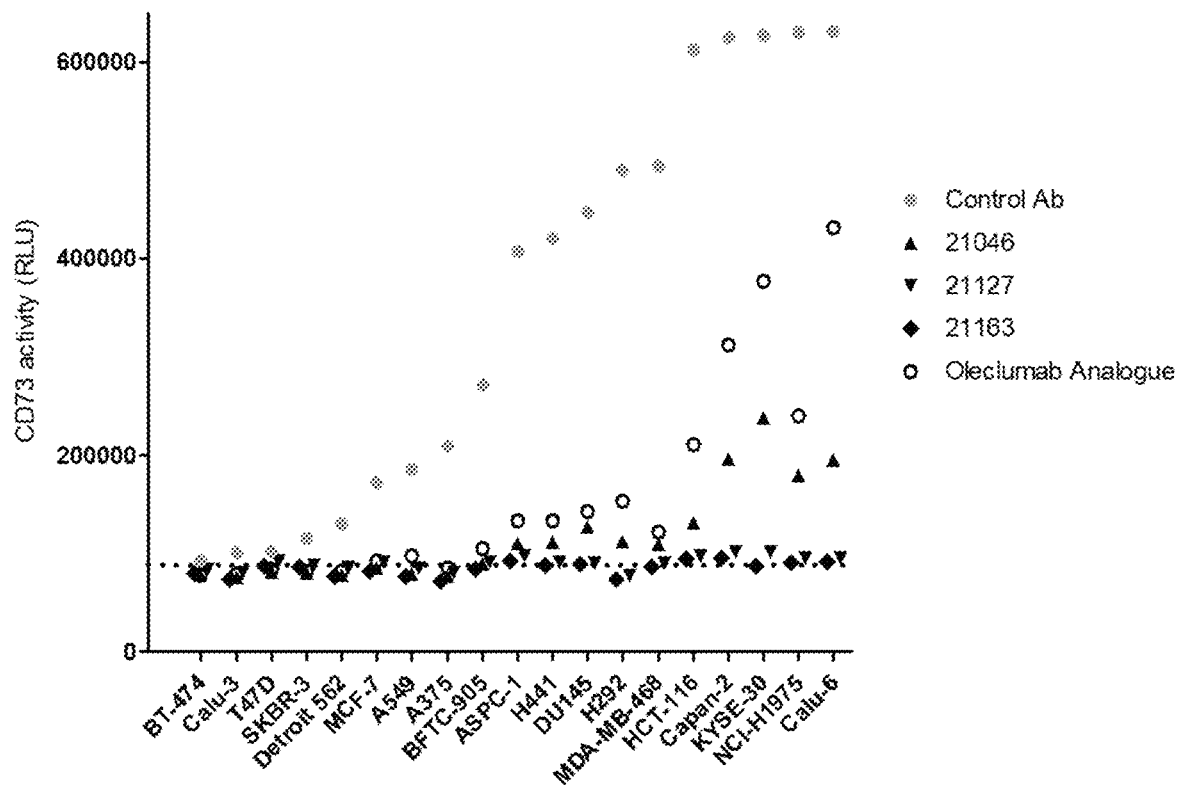
FIG. 10 is a graph showing the activity of CD73 expressed by 20 different cancer cell lines in the presence of the indicated antibodies as measured by the CellTiter-Glo assay. The "Control Ab" is a non-CD73-specific FcγR-deficient IgG1-LALA isotype antibody. Each datapoint represents the mean of three technical replicates.

Anti-CD73 antibodies 21127, 21046, 21163 were evaluated for the ability to inhibit the activity of CD73 expressed on a large panel of cancer cell lines representing a broad spectrum of CD73 expression and activity levels. The cell panel spans several cancer indications across multiple tissues of origin, as described in Table 11.
Materials and Methods Anti-CD73 antibodies were incubated at a concentration of 25 µg/mL with CD73-expressing cell lines for 30 minutes at 37° C. followed by addition of the CD73 substrate, AMP, and additional incubation for 3 hours at 37° C. Cellular CD73 activity was assessed by adding ATP to supernatants and measuring AMP inhibition of ATP detection using CellTiter-Glo® 2.0 (Promega Corporation) as described in Sachsenmeier et al., supra. CD73 activity is detected via luminescence.
Results The effect of the anti-CD73 antibodies on activity of CD73 expressed on 20 different cancer cell lines is shown in FIG. 10. It is evident that CD73 activity varied after treatment with the different anti-CD73 antibodies. Some antibodies (21046 and the oleclumab analogue) displayed some ability to inhibit CD73 at lower cellular CD73 activity levels, but failed to inhibit the enzyme at the highest activity levels, whereas other antibodies (21127 and 21163) strongly inhibited CD73 activity even at the highest activity levels observed in, e.g., the Calu-6, NCI-H1775, KYSE-30 and Capan-2 cell lines.

TABLE 11

List of cell lines and tissues of origin

| Cell line | Indication, Disease subtype (where applicable) |
|---|---|
| A375 | Skin Cancer, Carcinoma |
| A549 | Non-Small Cell Lung Cancer, Adenocarcinoma |
| ASPC-1 | Pancreas Cancer, Exocrine Adenocarcinoma |
| BFTC-905 | Bladder Cancer, Transitional Cell Carcinoma |
| BT-474 | Breast Cancer, Carcinoma |
| Calu-3 | Non-Small Cell Lung Cancer, Adenocarcinoma |
| Calu-6 | Non-Small Cell Lung Cancer |
| Capan-2 | Pancreas Cancer, Exocrine Adenocarcinoma |
| Detroit 562 | Head and Neck Cancer, Squamous Cell Carcinoma, Pharynx |
| DU145 | Prostate Cancer, Adenocarcinoma |
| H292 | Non-Small Cell Lung Cancer, Mucoepidermoid Carcinoma |
| H441 | Lung Cancer, Papillary Adenocarcinoma |
| HCT-116 | Colorectal Cancer, Adenocarcinoma |
| KYSE-30 | Esophageal Cancer, Squamous Cell Carcinoma |
| MCF-7 | Breast Cancer, Carcinoma |
| MDA-MB-468 | Breast Cancer, Carcinoma |
| NCI-H1975 | Non-Small Cell Lung Cancer, Adenocarcinoma |
| SKBR-3 | Breast Cancer, Carcinoma |
| T47D | Breast Cancer, Ductal Carcinoma |

Figure 11:
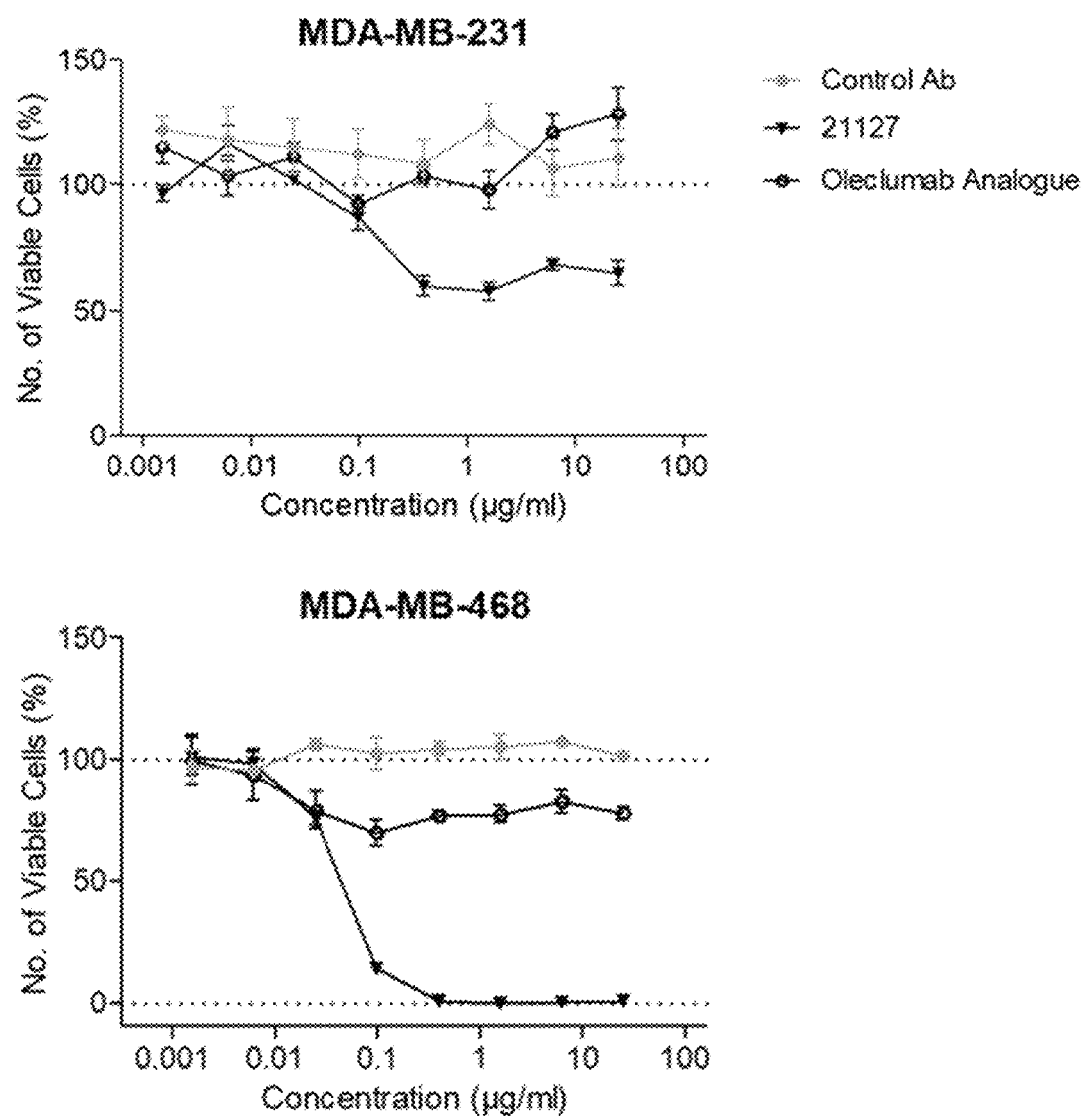
FIG. 11 is a pair of graphs showing the effect of blocking CD73 activity on viability of the two triple-negative breast cancer cell lines MBA-MB-231 (top panel) and MBA-MB-468 (bottom panel) grown in the presence of 300 μM AMP. The "Control Ab" is a non-CD73-specific FcγR-deficient IgG1-LALA isotype antibody. All counts are normalized to untreated cells, and data are presented as the mean of three technical replicates±SEM.

Example 14. In Vitro Test of Anti-CD73 Antibody Activity in a Cell-Based Viability Assay This example describes the in vitro functional characterization of antibody 21127 in a viability assay using two cancer cell lines grown in the presence of 300 µM AMP.
Materials and Methods Antibodies were evaluated in vitro for their ability to directly inhibit viability (survival and/or proliferation) of triple-negative breast cancer cell lines MDA-MB-231 and MDA-MB-468. The cells were seeded at 1000 cells/well in a 384 well plate in RPMI 1640 Glutamax (MDA-MB-231) or DMEM (MDA-MB-468) media supplemented with 2% FBS and 1% P/S, and incubated for four days in a humidified incubator at 37° C. with antibodies titrated from 25 µg/mL in the presence of AMP (adenosine monophosphate, Sigma-Aldrich) at 300 µM. Cell viability was quantified using WST-1 cell proliferation reagent (Roche) as per manufacturer's instructions.
Results It is apparent that 21127 and the oleclumab analogue differ with respect to functional readout (FIG. 11). Antibody 21127 displayed a pronounced effect on both cell lines, with MBA-MB-231 reduced to approximately 60% viable cells and MBA-MB-468 to 0% viable cells compared to untreated cells (i.e., no viable cells measurable over medium background). The oleclumab analogue displayed no significant effect on the viability of the MBA-MB-231 cell line, while the MBA-MB-468 was affected to some extent with viable cell numbers reduced to approx. 70-80% compared to untreated cells.

A similar effect may be expected in cancer cell lines derived from other tissues.

Figure 12:
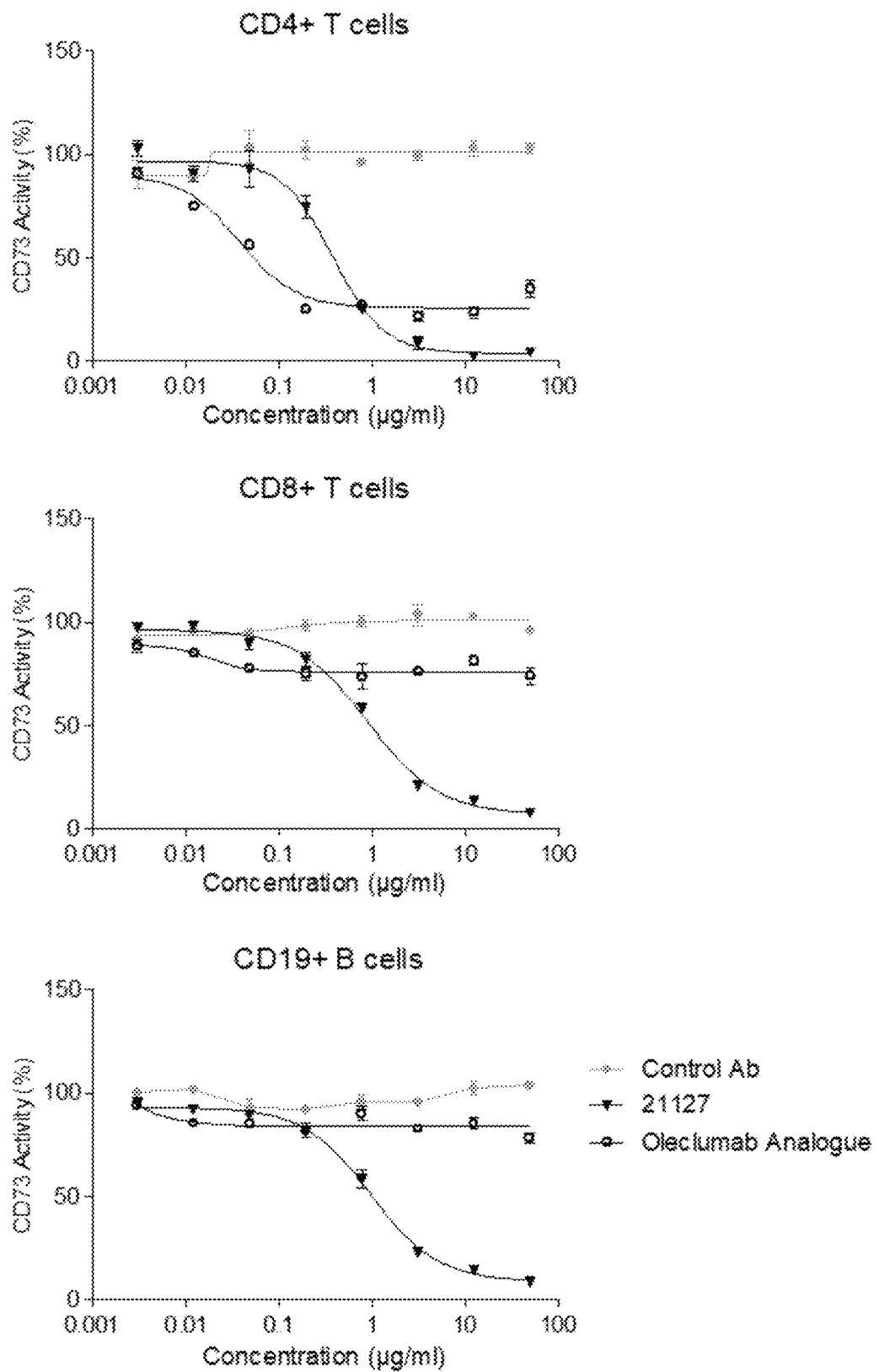
FIG. 12 is a set of graphs showing the activity of CD73 expressed by primary CD4$^+$ and CD8$^+$ T cells and CD19$^+$ B cells from healthy human donors in the presence of the indicated antibodies as measured by the CellTiter-Glo assay. Activity is normalized to untreated cells (100%). The "Control Ab" is a non-CD73-specific FcγR-deficient IgG1-LALA isotype antibody. Data are presented as the mean of three technical replicates±SEM.

Example 15. Inhibition of CD73 Expressed on Primary $CD4^+$ and $CD8^+$ T Cells and $CD19^+$ B Cells from Healthy Human Donors by Anti-CD73 Antibodies Anti-CD73 antibodies were evaluated for the ability to inhibit the activity of CD73 expressed on primary $CD4^+$ and $CD8^+$ T cells and $CD19^+$ B cells from healthy human donors.
Materials and Methods Primary $CD4^+$ and $CD8^+$ T cells and $CD19^+$ B cells were isolated from buffy coat PBMCs (peripheral blood mononuclear cells) using magnetic (MACS) beads with the relevant specificity according to manufacturer's instructions (Miltenyi Biotec). A four-fold dilution titration of anti-CD73 antibodies at a concentration from 50 to 0.003 µg/mL was incubated with isolated primary cells for 30 minutes at 37° C., followed by addition of the CD73 substrate, AMP, and additional incubation for 20 hours ($CD19^+$ B cells) or 40 hours ($CD4^+$ and $CD8^+$ T cells) at 37° C. CD73 activity was assessed by adding ATP to supernatants and measuring AMP inhibition of ATP detection using CellTiter-Glo® 2.0 (Promega Corporation) as described in Sachsenmeier et al., supra.
Results The activity of CD73 expressed on primary $CD4^+$ and $CD8^+$ T cells and $CD19^+$ B cells after treatment with the anti-CD73 antibodies is shown in FIG. 12. It is apparent that CD73 activity after treatment with antibody 21127 and the oleclumab analogue differed strongly. Higher concentrations of antibody 21127 demonstrated almost complete inhibition of CD73 activity in all primary cell types, while the oleclumab analogue showed very limited inhibition of CD73 activity in $CD19^+$ B cells and $CD8^+$ T cells and only partial inhibition in $CD4^+$ T cells. The ability of the oleclumab analogue to inhibit CD73 activity correlates with the level of CD73 expression, as peripheral blood $CD4^+$ T cells from healthy donors on average have limited CD73 expression, while $CD19^+$ B cells on average express high levels of CD73 and $CD8^+$ T cells on average express intermediate levels (Allard et al., *Immunol Rev* 276(1):121-144 (2017)).

Example 16. Functionality of Anti-CD73 Antibodies in a T Cell Proliferation Assay The ability of anti-CD73 antibodies 21028, 21046, 21127, and 21163 to inhibit the activity of CD73 expressed on $CD4^+$ T cells was evaluated and compared to an oleclumab analogue in an in vitro assay. CD4+ T cells were isolated from a healthy donor and activated with anti-CD3/CD28 beads (Thermo Fisher Scientific), AMP and anti-CD73 antibodies for 48 hours, followed by addition of 3H-thymidine (Perkin Elmer Corporation) for an additional 24 hours. T cell proliferation was measured as 3H-thymidine incorporation and normalized to controls not treated with AMP.

Figure 13:
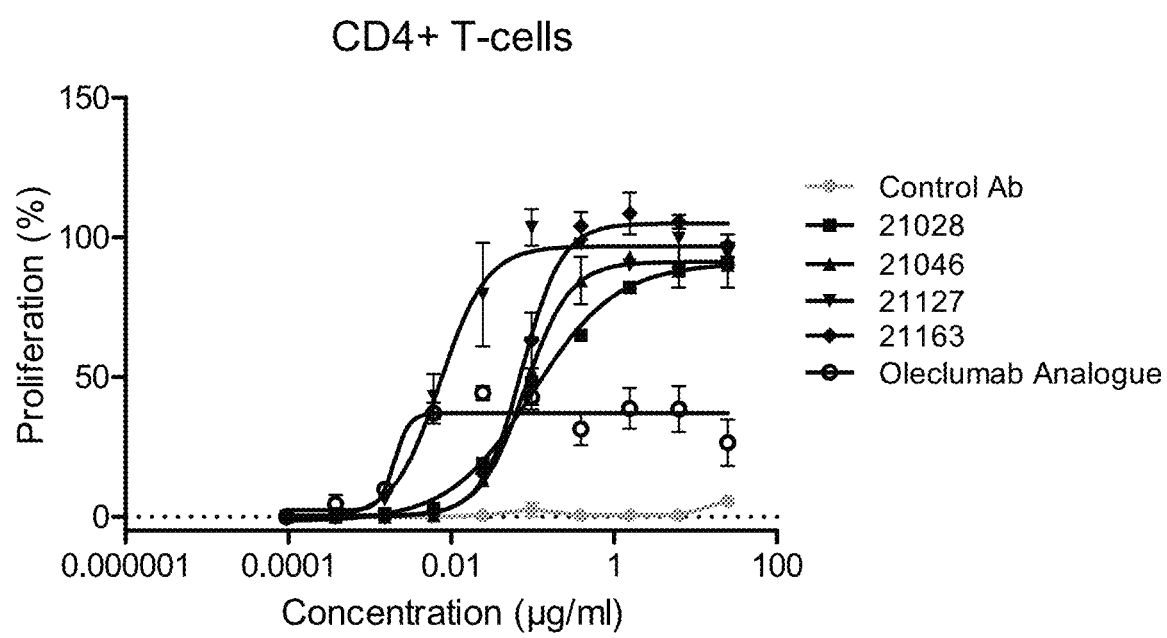
FIG. 13 is a graph showing the proliferation of CD4$^+$ T cells treated with anti-CD3/CD28 beads, AMP, and the indicated anti-CD73 antibodies and a reference antibody (oleclumab) analogue. Data are normalized to controls not treated with AMP and presented as mean±SEM.

T cell proliferation after treatment with the different anti-CD73 antibodies is shown in FIG. 13. It is evident that the stimulatory function of the anti-CD73 antibodies on T cell proliferation is concentration dependent and that all of the antibodies stimulate T cell proliferation, albeit with differing potency and efficacy. All antibodies except the oleclumab analogue fully restore T cell proliferation, with antibody 21127 doing so with the highest potency.

Example 17. Functionality of Anti-CD73 Antibodies in a T Cell Activation Assay The ability of an anti-CD73 antibody to inhibit the activity of CD73 expressed on CD4+ and CD8+ T cells was evaluated and compared to an oleclumab analogue in an in vitro assay.

CD4+ and CD8+ T cells were isolated from healthy donors and activated with anti-CD3/CD28 beads (Thermo Fisher Scientific), AMP and anti-CD73 antibodies for 72 hours, followed by harvest of supernatant. T cell activation was measured as IFN-$\gamma$ levels in supernatant using ELISA (Thermo Fisher Scientific).

Figure 14:
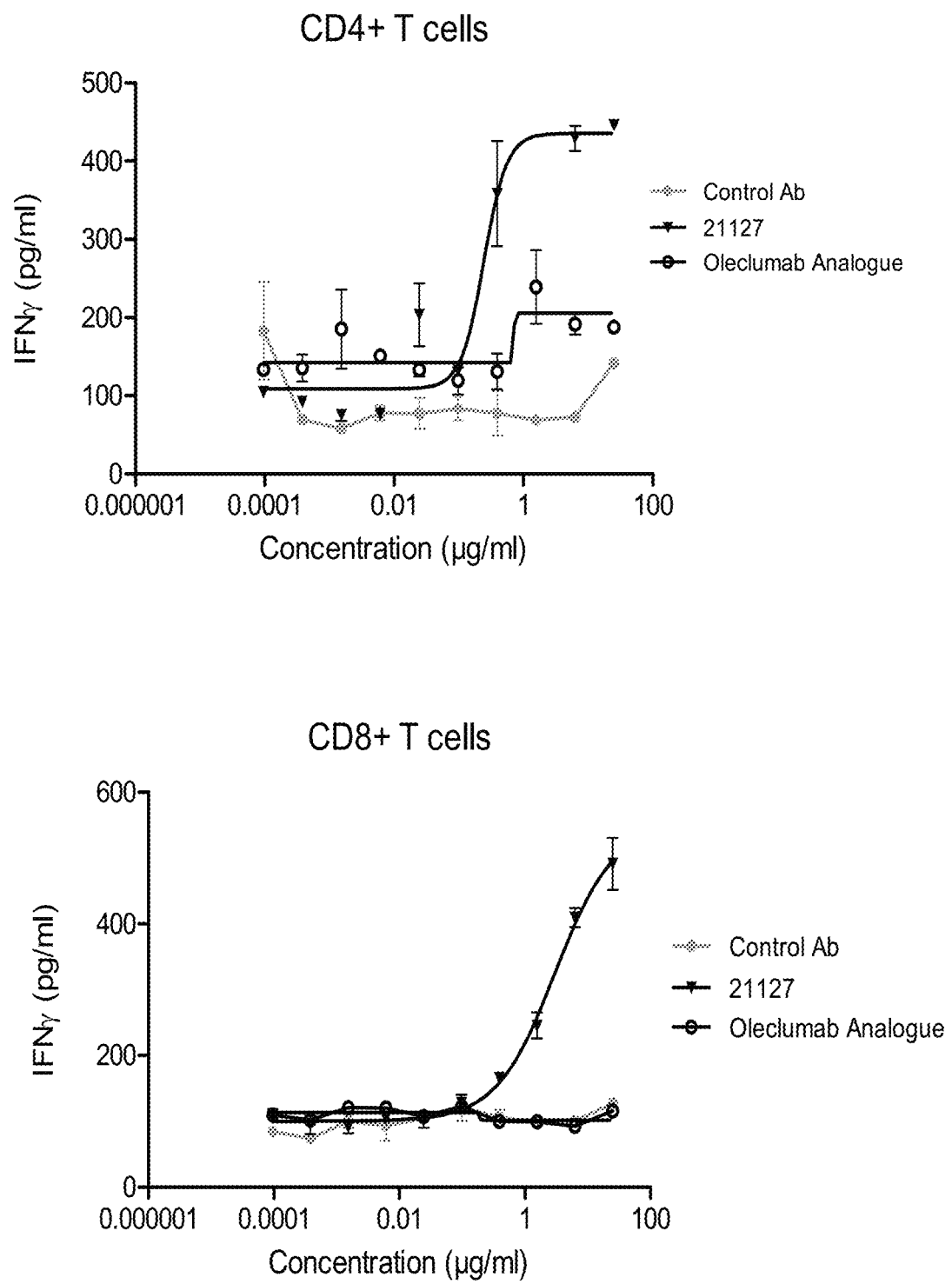
FIG. 14 is a pair of graphs showing the activation of CD4$^+$ (top panel) and CD8$^+$ (bottom panel) T cells treated with anti-CD3/CD28 beads, AMP and 21127 or a reference antibody (oleclumab) analogue. The "Control Ab" is a non-CD73-specific FcγR-deficient IgG1-LALA isotype antibody. Data are presented as mean±SEM.

T cell activation after treatment with the different anti-CD73 antibodies is shown in FIG. 14. It is evident that the stimulatory function of antibody 21127 on T cell activation is concentration dependent, and that 21127 results in higher IFN-$\gamma$ levels than the oleclumab analogue.

Example 18. Functionality of Anti-CD73 Antibodies in a One-Way MLR Assay

The ability of an anti-CD73 antibody to inhibit the activity of CD73 in a one-way mixed lymphocyte reaction (MLR) was evaluated and compared to an oleclumab analogue in an in vitro assay.

Dendritic cells (DCs) and CD4+ T cells isolated from two different healthy donors were co-cultured to induce an alloantigen specific reaction resulting in cytokine production and T cell activation and/or proliferation. DCs were differentiated from CD14+ monocytes by 7 days of culture with 20 ng/mL granulocyte-macrophage colony-stimulating factor (GM-CSF) and 20 ng/mL interleukin-4 (IL-4), and mixed in a 1:10 ratio with CD4+ T cells isolated from peripheral blood mononuclear cells (PBMCs) from healthy donor material. The one-way MLR was incubated with 25 µg/mL anti-PD-1 antibody (12819; see PCT Patent Publication WO 2017/055547), 50 µM AMP and the indicated concentration of anti-CD73 antibody for 48 hours, followed by addition of 3H-thymidine (PerkinElmer Corporation) for an additional 24 hours. Proliferation was measured as 3H-thymidine incorporation and normalized to controls not treated with AMP.

Figure 15:
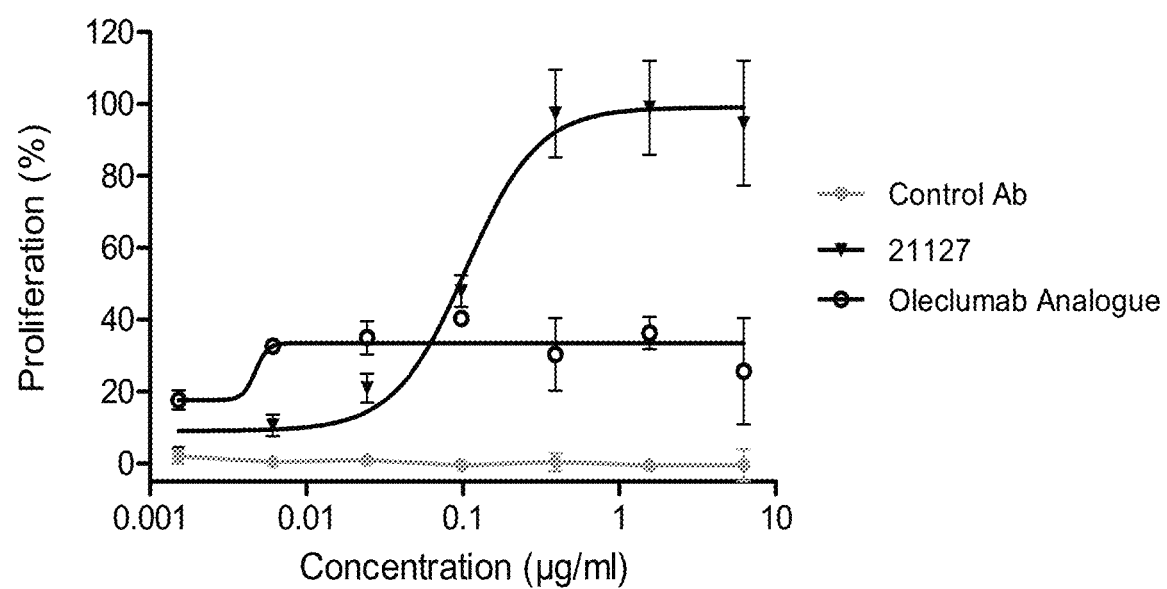
FIG. 15 is a graph showing T cell proliferation in a one-way mixed lymphocyte reaction (MLR) upon incubation with anti-PD-1 antibody (12819), AMP, and the indicated anti-CD73 antibody or a reference antibody (oleclumab) analogue. The "Control Ab" is a non-CD73-specific FcγR-deficient IgG1-LALA isotype antibody. Data are normalized to controls not treated with AMP and presented as mean±SEM.

T cell proliferation after treatment with the different anti-CD73 antibodies is shown in FIG. 15. It is evident that the stimulatory function of anti-CD73 antibodies on proliferation is concentration dependent and that both antibody 21127 and the oleclumab analogue stimulated T cell proliferation. However, only antibody 21127 fully restored proliferation.

Example 19. Combination of Anti-CD73 and Anti-PD-1 Antibodies in a One-Way MLR Assay This example examines the ability of a combination of an anti-PD-1 antibody (12819) and an anti-CD73 antibody (21127) to enhance T cell activation in a one-way mixed lymphocyte reaction (MLR).

Dendritic cells (DCs) and CD4+ T cells isolated from two different healthy donors were co-cultured to induce an alloantigen specific reaction resulting in cytokine production and T cell activation and/or proliferation. DCs were differentiated from CD14+ monocytes by 7 days of culture with 20 ng/mL granulocyte-macrophage colony-stimulating factor (GM-CSF) and 20 ng/mL interleukin-4 (IL-4), and mixed in a 1:10 ratio with CD4+ T cells isolated from peripheral blood mononuclear cells (PBMCs) from healthy donor material. The one-way MLR was incubated with or without 50 µM AMP and with anti-CD73 antibody 21127 and/or anti-PD-1 antibody (12819; see PCT Patent Publication WO 2017/055547) for 72 hours, followed by harvest of supernatant. The combination of anti-CD73 antibody 21127 and anti-PD-1 antibody 12819 was added in a 1:1 ratio of the two antibodies. T cell activation was measured by quantifying IFN-$\gamma$ levels in supernatant using ELISA (Thermo Fisher Scientific), and normalized to controls not treated with AMP.

Figure 16:
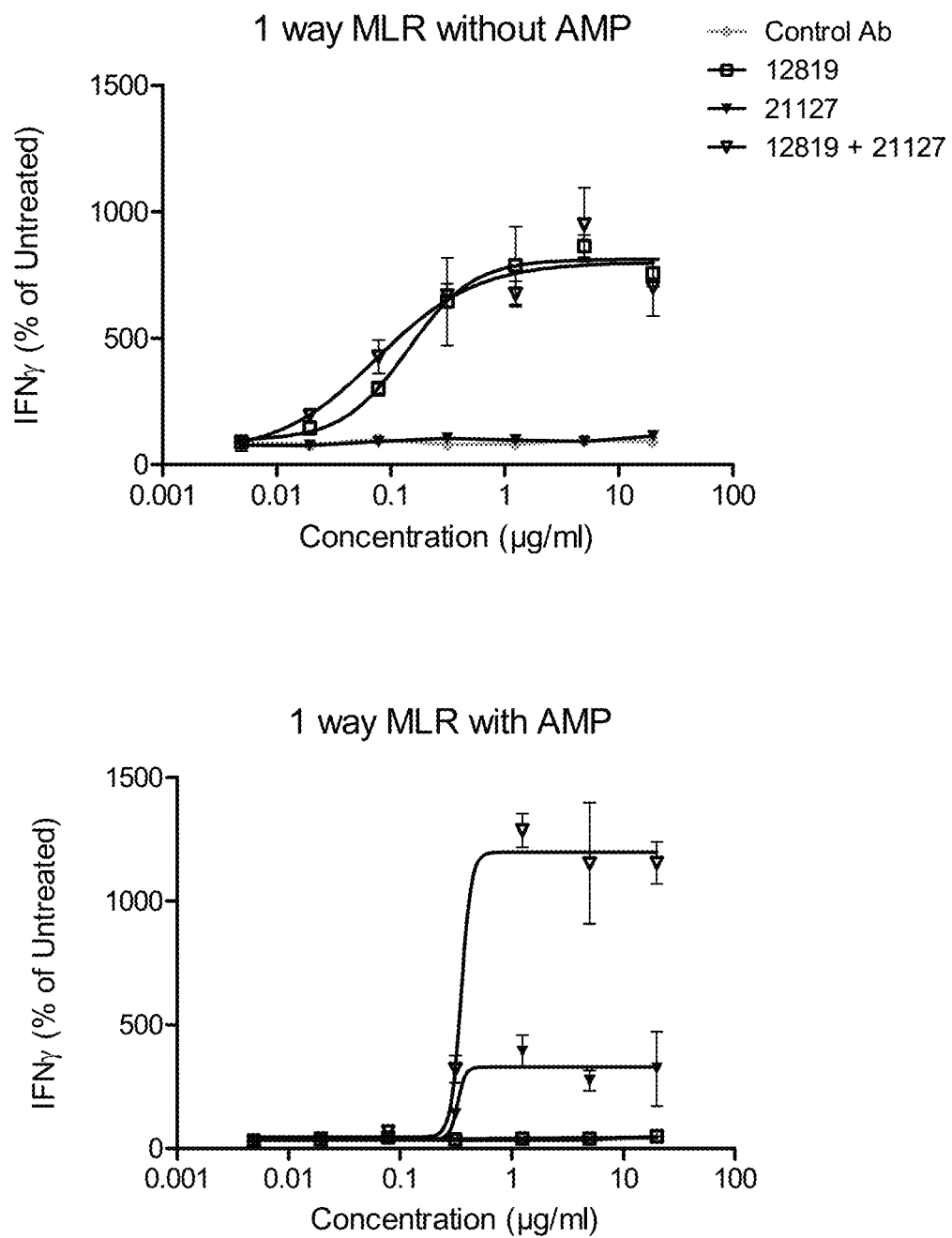
FIG. 16 is a pair of graphs showing T cell proliferation in a one-way MLR upon incubation with (bottom panel) or without (top panel) AMP and with the indicated concentrations of anti-PD-1 and/or anti-CD73 antibodies. The 12819+21127 combination is a 1:1 mixture of the two antibodies, and the indicated concentrations show total concentration of the mixture. The "Control Ab" is a non-CD73-specific FcγR-deficient IgG1-LALA isotype antibody. Data are normalized to controls not treated with AMP and presented as mean±SEM.

T cell activation in the one-way MLR, as measured by IFN-$\gamma$ levels after treatment with antibody 12819 and/or 21127, is shown in FIG. 16. It is evident that the anti-PD-1 antibody 12819 strongly activated the one-way MLR without AMP and both with and without simultaneous incubation with antibody 21127 (top panel). The activation of the one-way MLR with the anti-PD-1 antibody is considerably less when AMP is added to the one-way MLR (bottom panel). However, combining the anti-PD-1 antibody and anti-CD73 antibody 21127 at least partly restored strong T cell activation, highlighting the benefit of the anti-PD-1 antibody/anti-CD73 antibody combination.

Example 20. Functionality of Anti-CD73 Antibodies in a B Cell Activation Assay The ability of antibodies 21046 and 21127 to stimulate B cell activation was evaluated in an in vitro B cell activation assay. PBMCs from a healthy donor were stimulated overnight with 21046, 21127, or the oleclumab analogue (10 µg/mL) as well as CD40 ligand (0.5 µg/mL). Flow cytometry analysis was performed with gating on B cells (CD20+) and B cell activation evaluated as upregulation of the B cell activation markers CD25, CD69, and CD83.

Figure 17A:
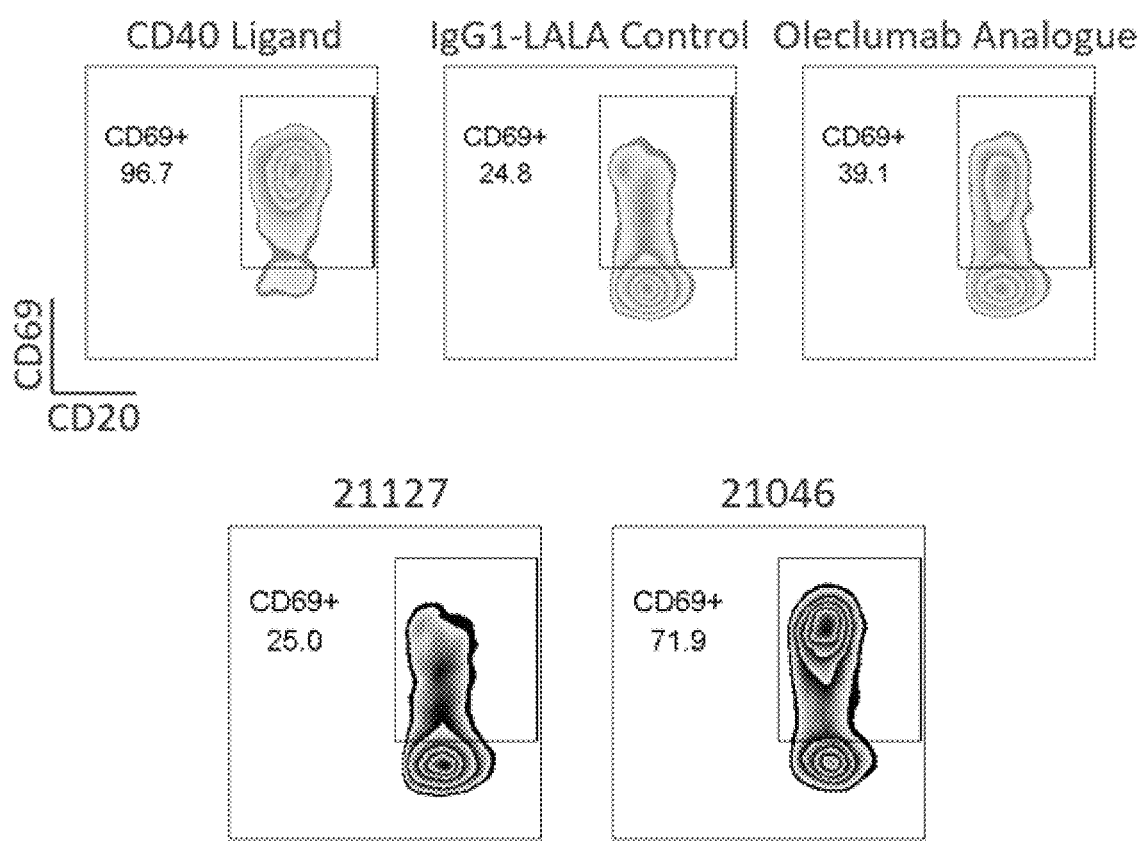
FIGS. 17A and 17B depict B cell activation in PBMCs from a healthy donor stimulated overnight with the indicated antibodies (10 μg/mL) and CD40 ligand (0.5 μg/mL).
Figure 17B:
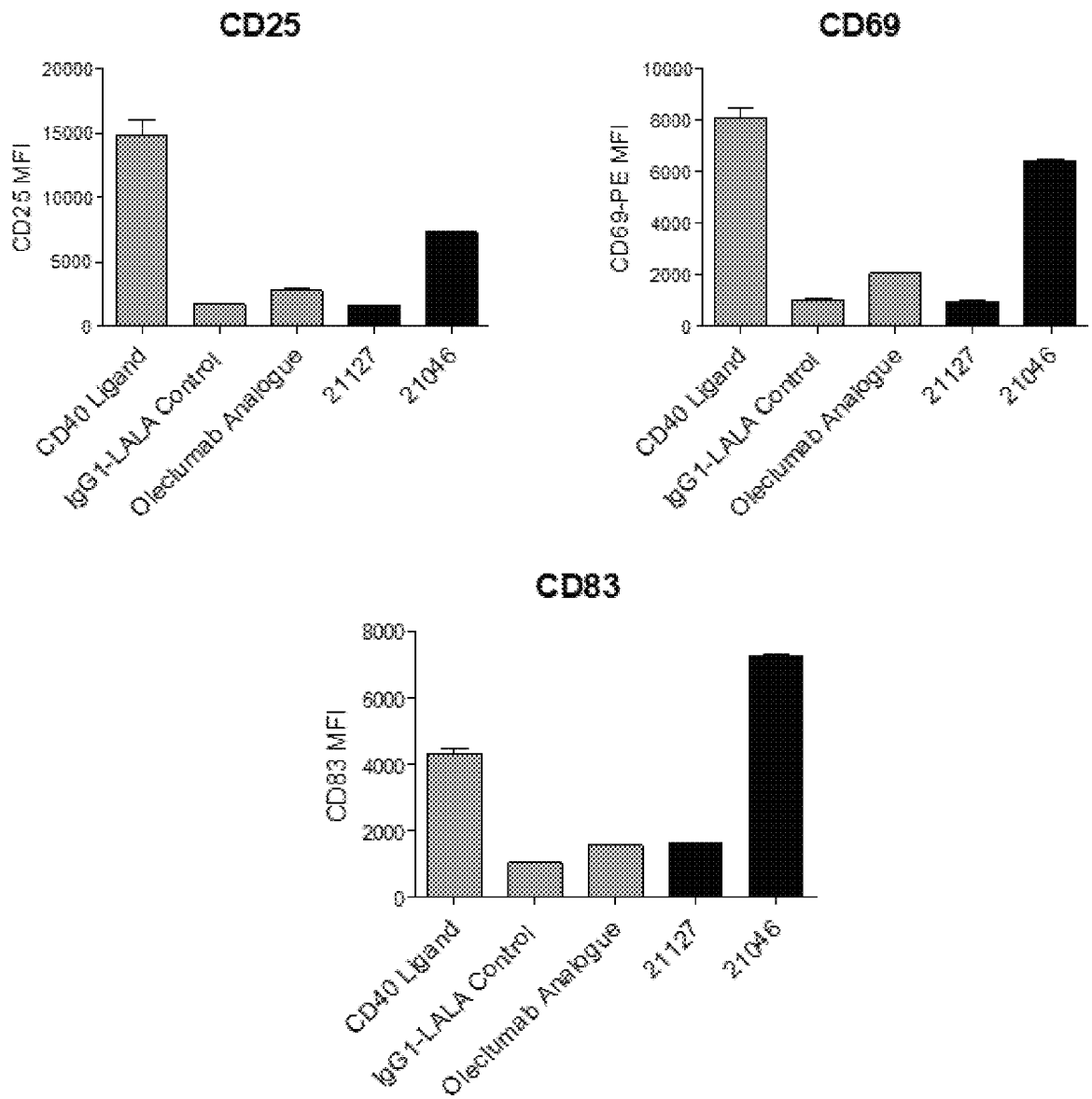

As shown in FIGS. 17A and 17B, antibody 21046 stimulates strong upregulation of the B cell activation markers CD25, CD69 and CD83, whereas antibody 21127 and the oleclumab analogue have limited effect on B cell activation.

Example 21. Anti-CD73 Antibody-Induced Decrease in CD73 Levels in H292 Cells The ability of anti-CD73 antibodies 21127, 21028, 21046, and 21163 to modulate CD73 levels in a cell line was evaluated and compared to oleclumab analogue. Anti-CD73 antibodies were incubated with human cell line H292 for 24 hours at 37° C. at 25 µg/mL followed by cell lysis and evaluation of CD73 levels using Simple Western technique (ProteinSimple).

Figure 18:
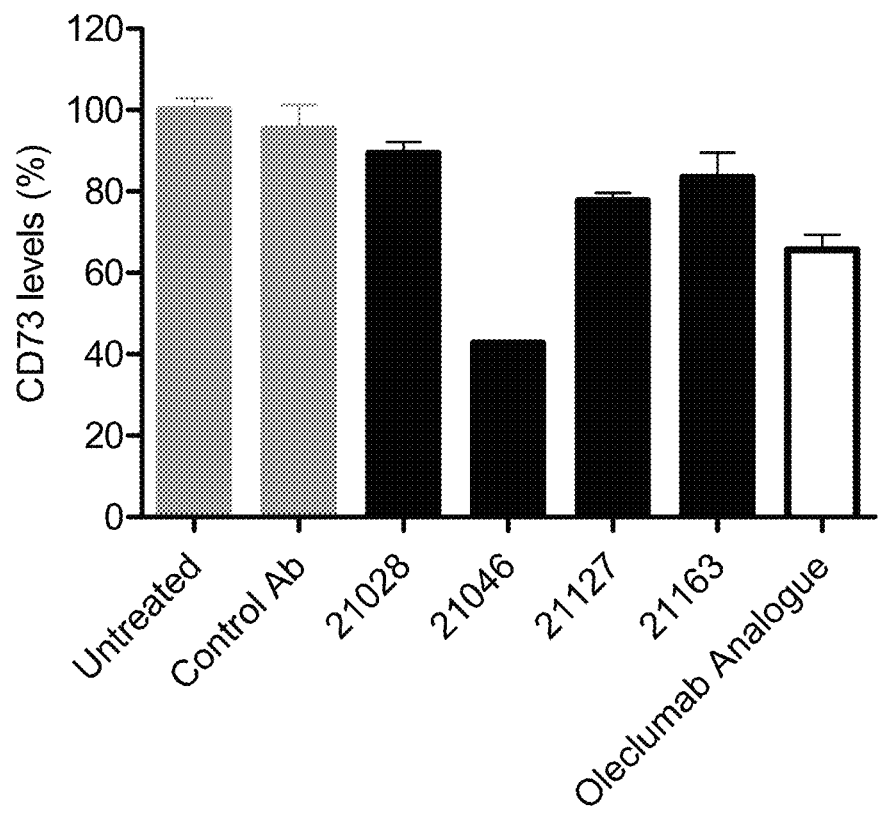
FIG. 18 is a graph showing the levels of CD73 expressed in H292 cells after 24 hours of treatment with an indicated anti-CD73 antibody or the reference antibody (oleclumab) analogue. Data are normalized to untreated control and are presented as mean±SEM.

FIG. 18 shows CD73 levels after treatment with antibody 21127, 21028, 21046, or 21163 or the oleclumab analogue. Incubation with anti-CD73 antibody 21046 or the oleclumab analogue resulted in some CD73 downmodulation, whereas the other anti-CD73 antibodies had a modest effect, if any, on CD73 levels.

Example 22. Functionality of an Anti-CD73 Antibody in Human Tumor Xenograft Models This example demonstrates the ability of anti-CD73 antibody 21127 to inhibit the enzymatic activity of CD73 expressed on cells isolated from human tumor xenografts.

Materials and Methods

The human melanoma cell line A375 was inoculated subcutaneously into the flanks of 6-8-week-old female NOG or NOD-scid mice. In one example (FIG. 19, top panel), human PBMC were intraperitoneally injected one day after tumor cell inoculation. Tumors were measured three times weekly by caliper in two dimensions, and tumor volume in $mm^3$ was calculated according to the formula: $(width)^2 \times length \times 0.5$. The mice were treated three times weekly by intraperitoneal injection of vehicle buffer or (1) antibody 21127, (2) an oleclumab analogue, or (3) antibody 21127 combined with anti-mouse CD73 antibody TY/23 (BioXcell). Unlike the oleclumab analogue, antibody 21127 is not cross-reactive to mouse CD73. Hence, to compare inhibition of CD73 activity in the tumor mass, which also contains murine cells expressing CD73 (endothelial and stromal cells), antibody 21127 was combined with anti-mouse CD73 antibody TY/23. The antibodies were dosed at 5 mg/kg, 20 mg/kg or 50 mg/kg. At different time points after treatment withdrawal, tumors were harvested and dissociated using a tumor dissociation kit and the gentleMACS Octo Dissociator (Miltenyi). The resulting cell suspension was incubated with the CD73 substrate AMP, for 3 hours at 37° C. CD73 activity was investigated by adding ATP to supernatants and measuring AMP inhibition of ATP detection by CellTiter-Glo® 2.0 (Promega Corporation) as described in Sachsenmeier et al., supra.

Results

Figure 19:
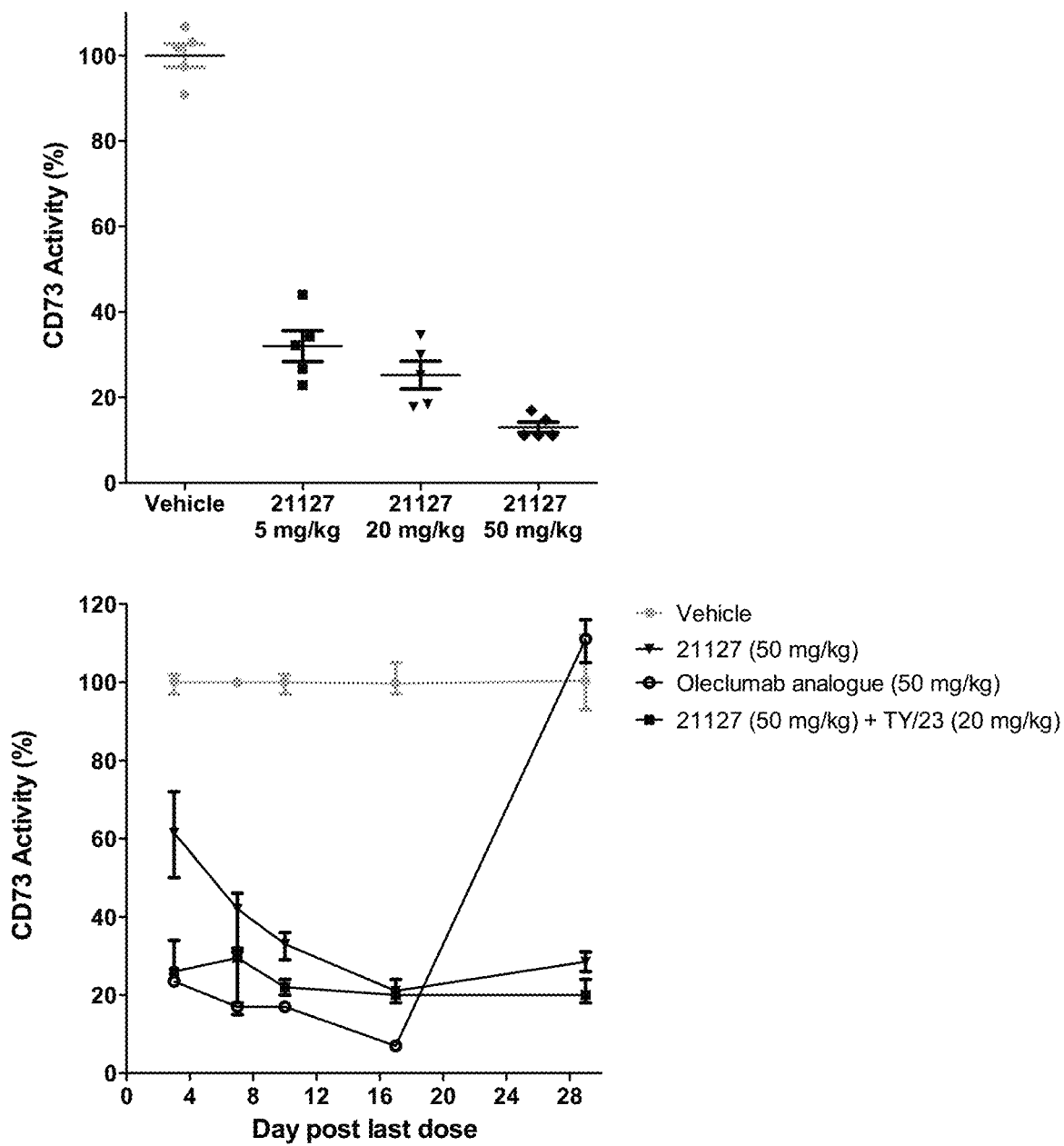
FIG. 19 is a pair of graphs showing the activity of CD73 in the human xenograft melanoma model A375, following treatment with the indicated antibodies. Top panel: PBMC-humanized mice engrafted with A375 received different doses of 21127 three times weekly for two weeks. Tumors were harvested one day after the last dose and analyzed for CD73 activity. Bottom panel: NOD-scid mice subcutaneously engrafted with A375 were treated three times weekly for one week with the indicated antibodies or combinations. Tumors were harvested on days 3, 7, 10, 17, and 29 after the last treatment and analyzed for CD73 activity. Data are normalized to untreated controls and are presented as mean±SEM.

Antibody 21127 demonstrated dose-dependent inhibition of CD73 activity in tumors harvested from PBMC-humanized mice engrafted with the A375 human melanoma cell line after repeated dosing for two weeks (FIG. 19, top panel). The effect on CD73 enzymatic activity was also found to last for an extended period of time after treatment withdrawal.

As shown in FIG. 19, bottom panel, the oleclumab analogue inhibited CD73 activity for 16 days post treatment and the enzyme activity was fully recovered on day 28 post treatment. By contrast, antibody 21127 alone or in combination with TY/23 showed sustained inhibition of CD73 activity for 28 days post treatment withdrawal.

Example 23. In Vivo Efficacy of an Anti-CD73 Antibody in a Human Xenograft Tumor Model with No Immune Cells This example demonstrates the ability of anti-CD73 antibodies to inhibit tumor growth in a human triple-negative breast cancer xenograft model.

Human MDA-MB-231 triple-negative breast cancer cells were inoculated subcutaneously into the flanks of 6-8 week old female NOD-scid mice. Tumors were measured three times weekly by caliper in two dimensions, and tumor volume in $mm^3$ was calculated according to the formula: $(width)^2 \times length \times 0.5$. The mice were treated twice weekly with a total of 16 treatments by intraperitoneal injection of vehicle buffer, antibody 21127, or an oleclumab analogue, followed by an observation period. The antibodies were dosed at 10 mg/kg. Two-way ANOVA with Bonferroni's multiple comparisons test was applied to compare tumor volumes at each time point between treatment groups. Statistical analyses were performed using GraphPad Prism version 5.0 (GraphPad Software, Inc.).

Figure 20:
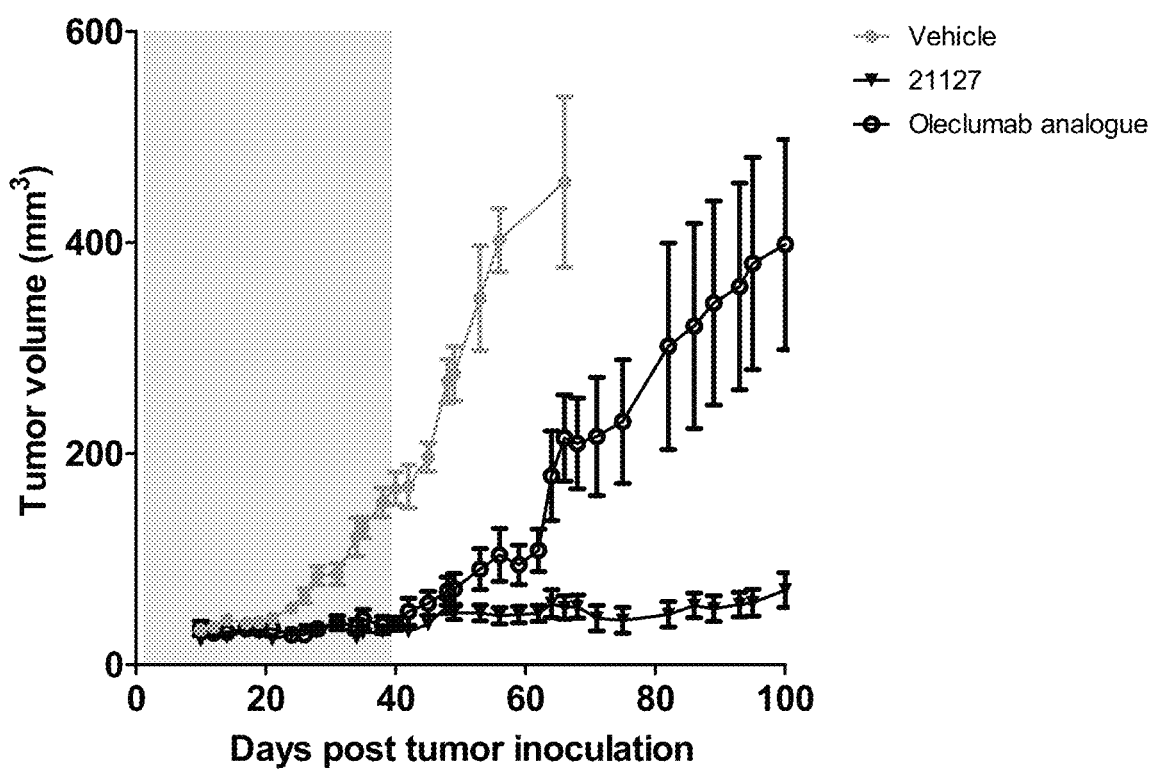
FIG. 20 is a graph showing tumor growth in NOD-scid mice subcutaneously engrafted with the human triple-negative breast cancer cell line MDA-MB-231. The mice were treated twice weekly with 10 mg/kg antibody 21127 or a reference antibody (oleclumab) analogue. The gray area denotes the treatment period. Data are presented as mean±SEM.

Antibody 21127 and the oleclumab analogue showed a pronounced tumor inhibitory effect during treatment (FIG. 20). Following treatment withdrawal, regrowth of tumors treated with the oleclumab analogue was observed. By contrast, mice treated with antibody 21127 effectively controlled tumor growth during the treatment with limited gain in tumor size for 60 days post treatment.

Example 24. In Vivo Efficacy of an Anti-CD73 Antibody in Human Xenograft Tumor Models in Mice Reconstituted with Human PBMCs This example demonstrates in vivo efficacy of the anti-CD73 antibody 21127 in PBMC-humanized mice engrafted with the human lung carcinoma cells or human melanoma cells.

Cells from human lung carcinoma cell line Calu-6 or human A375 melanoma cell line were subcutaneously engrafted into NOG mice one day prior to intraperitoneal injection of human PBMCs. Treatment was initiated on the day of PBMC injection, and the mice were treated three times weekly for a total of six treatments by intraperitoneal injection of vehicle buffer or anti-CD73 antibody 21127 at 10 mg/kg (n=10/group). Tumors were measured three times weekly by caliper in two dimensions, and tumor volume in $mm^3$ was calculated per the formula: $(width)^2 \times length \times 0.5$. Two-way ANOVA with Bonferroni's multiple comparisons test was applied to compare tumor volumes at each time-point between treatment groups. Statistical analyses were performed using GraphPad Prism version 5.0 (GraphPad Software, Inc.).

Figure 21:
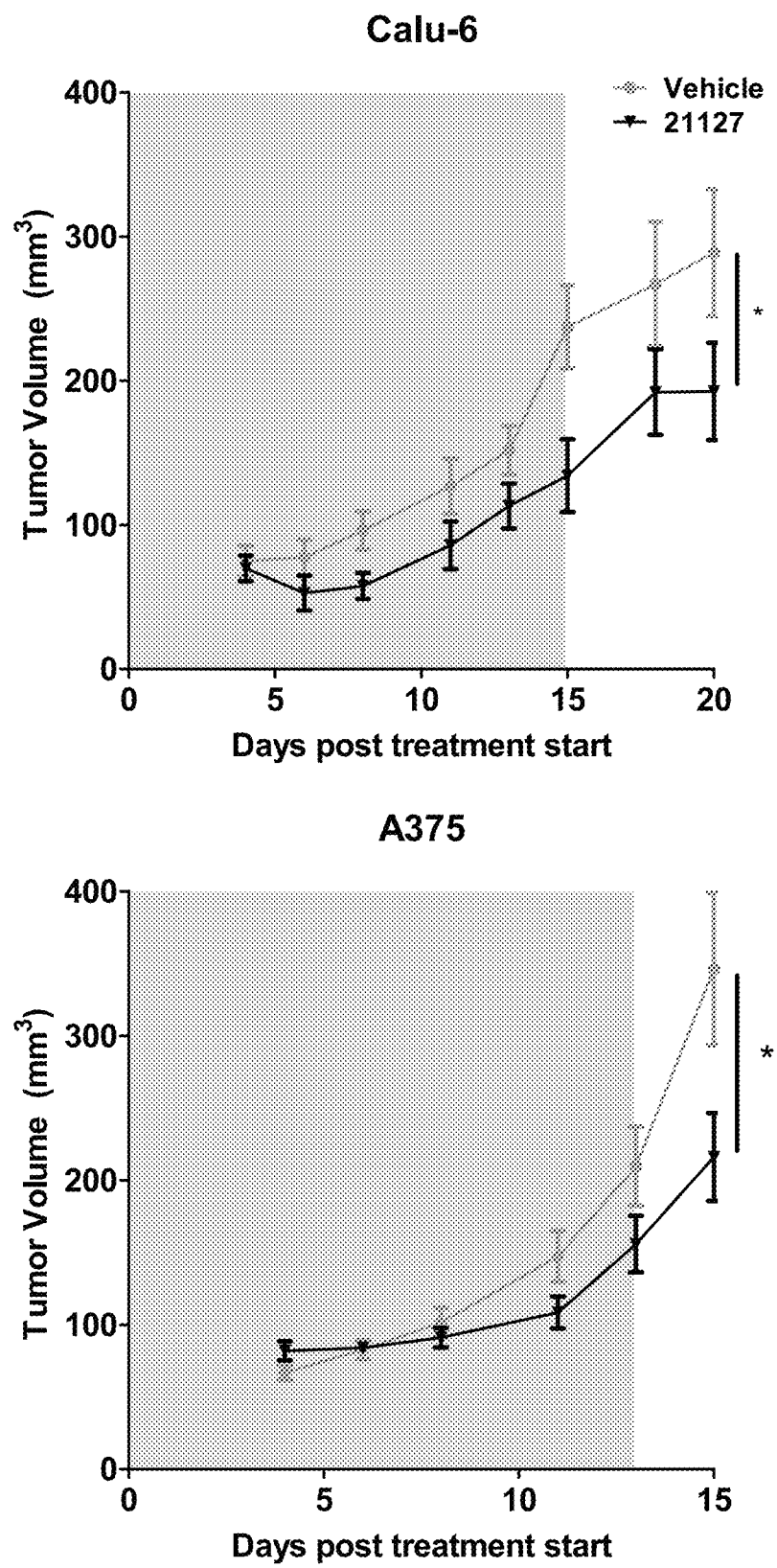
FIG. 21 is a pair of graphs showing the effect of treatment with the anti-CD73 antibody 21127 or vehicle on tumor growth in PBMC-humanized mice engrafted with Calu-6 or A375 tumor cells. The gray area denotes the treatment period. Data are presented as mean±SEM. * P<0.05

As shown in FIG. 21, treatment with antibody 21127 resulted in significant tumor growth delay (P<0.05 vs. vehicle control) in two human tumor xenograft models (Calu-6 and A375) in mice reconstituted with human PBMCs. Each graph in FIG. 21 represents one human PBMC donor.

The invention claimed is:

1. An anti-CD73 antibody or an antigen-binding portion thereof, wherein said antibody comprises the H-CDR1-3 and L-CDR1-3 amino acid sequences of:
   a) SEQ ID NOs: 17-22, respectively;
   b) SEQ ID NOs: 23-28, respectively;
   c) SEQ ID NOs: 29-34, respectively; or
   d) SEQ ID NOs: 35-40, respectively.

2. The anti-CD73 antibody or antigen-binding portion of claim 1, wherein said antibody comprises a heavy chain variable domain amino acid sequence and a light chain variable domain amino acid sequence that are at least 90% identical to the amino acid sequences of:
   a) SEQ ID NOs: 9 and 13, respectively;
   b) SEQ ID NOs: 10 and 14, respectively;
   c) SEQ ID NOs: 11 and 15, respectively; or
   d) SEQ ID NOs: 12 and 16, respectively.

3. The anti-CD73 antibody or antigen-binding portion of claim 1, wherein said antibody comprises a heavy chain variable domain and a light chain variable domain comprising the amino acid sequences of:
   a) SEQ ID NOs: 9 and 13, respectively;
   b) SEQ ID NOs: 10 and 14, respectively;
   c) SEQ ID NOs: 11 and 15, respectively; or
   d) SEQ ID NOs: 12 and 16, respectively.

4. The anti-CD73 antibody or antigen-binding portion of claim 1, wherein the antibody or antigen-binding portion has at least one property selected from:
   a) inhibits the activity of soluble CD73 in vitro;
   b) inhibits the activity of CD73 on Calu-6 cells in vitro;

c) inhibits the activity of CD73 on H292 cells in vitro;
d) specifically binds to human and cynomolgus CD73 expressed on CHO-S cells;
e) binds to the ECD of human CD73 with a $K_D$ of 1 nM or less as measured by SPR;
f) binds to the ECD of cynomolgus CD73 with a $K_D$ of 0.7 nM or less as measured by SPR;
g) binds an epitope on the CD73 homodimer in a manner that gives rise to a 1:1 complex;
h) inhibits soluble CD73 activity more effectively than oleclumab in vitro;
i) inhibits CD73 activity on Calu-6, H292, and Cynom-K1 cells in vitro;
j) inhibits CD73 activity on Calu-6, NCI-H1775, KYSE-30, and Capan-2 cells in vitro;
k) restores proliferation of $CD4^+$ T cells in vitro; and
l) does not reduce levels of CD73 in H292 cells in vitro by more than 25%.

5. The anti-CD73 antibody of claim 1, wherein the antibody is an $IgG_1$ and wherein one or both of the amino acid residues at positions 234 and 235 are mutated from Leu to Ala, wherein the positions are numbered according to the Eu numbering scheme.

6. An anti-CD73 antibody that comprises:
a) a heavy chain (HC) comprising the amino acid sequences of SEQ ID NOs: 9 and 41 and a light chain (LC) comprising the amino acid sequences of SEQ ID NOs: 13 and 42;
b) an HC comprising the amino acid sequences of SEQ ID NOs: 10 and 41 and an LC comprising the amino acid sequences of SEQ ID NOs: 14 and 42;
c) an HC comprising the amino acid sequences of SEQ ID NOs: 11 and 41 and an LC comprising the amino acid sequences of SEQ ID NOs: 15 and 42; or
d) an HC comprising the amino acid sequences of SEQ ID NOs: 12 and 41 and an LC comprising the amino acid sequences of SEQ ID NOs: 16 and 42.

7. A pharmaceutical composition comprising the anti-CD73 antibody or antigen-binding portion of claim 1 and a pharmaceutically acceptable excipient.

8. The pharmaceutical composition of claim 7, further comprising an immunostimulatory agent, a vaccine, a chemotherapeutic agent, an anti-neoplastic agent, an anti-angiogenic agent, a tyrosine kinase inhibitor, or a CD73 pathway inhibitor.

9. An isolated nucleic acid molecule comprising a nucleotide sequence that encodes the heavy chain, a nucleotide sequence that encodes the light chain, or both, of the anti-CD73 antibody or antigen-binding portion of claim 1.

10. The isolated nucleic acid molecule of claim 9, wherein said nucleic acid molecule comprises the nucleotide sequence of any one of SEQ ID NOs: 1-8.

11. A vector comprising the isolated nucleic acid molecule of claim 9, wherein said vector further comprises an expression control sequence.

12. A host cell comprising a nucleotide sequence that encodes the heavy chain, and a nucleotide sequence that encodes the light chain, of the anti-CD73 antibody or antigen-binding portion of claim 1.

13. A method for producing an anti-CD73 antibody or an antigen-binding portion thereof, comprising providing a host cell according to claim 12, culturing said host cell under conditions suitable for expression of the antibody or portion, and isolating the resulting antibody or portion.

14. A bi-specific binding molecule comprising the antigen-binding portion of one or two distinct anti-CD73 antibodies according to claim 1.

15. A method for:
a) decreasing CD73 activity;
b) increasing $CD4^+$ T cell proliferation; and/or
c) stimulating the immune system,
in a patient in need thereof, comprising administering to said patient a therapeutically effective amount of the anti-CD73 antibody or antigen-binding portion of claim 1.

16. A method for treating cancer in a patient, comprising administering to said patient a therapeutically effective amount of the anti-CD73 antibody or antigen-binding portion of claim 1.

17. The method of claim 16, wherein the cancer originates in a tissue selected from the group consisting of skin, lung, intestine, colon, ovary, brain, prostate, kidney, soft tissues, the hematopoietic system, head and neck, liver, bone, bladder, breast, stomach, uterus, cervix, and pancreas.

18. The method of claim 16, wherein the cancer is melanoma, head and neck cancer, breast cancer, bladder cancer, non-small cell lung cancer, pancreatic cancer, ovarian cancer, renal cell carcinoma, prostate cancer, colorectal cancer, cholangiocarcinoma, thyroid cancer, or testicular cancer.

19. The method of claim 16, further comprising administering to the patient an immunostimulatory agent, a vaccine, a chemotherapeutic agent, an anti-neoplastic agent, an anti-angiogenic agent, a tyrosine kinase inhibitor, a CD73 pathway inhibitor, or radiation therapy.

20. An anti-CD73 antibody that comprises a heavy chain (HC) comprising the amino acid sequences of SEQ ID NOs: 11 and 41 and a light chain (LC) comprising the amino acid sequences of SEQ ID NOs: 15 and 42.

* * * * *

UNITED STATES PATENT AND TRADEMARK OFFICE
CERTIFICATE OF CORRECTION

| | | |
|---|---|---|
| PATENT NO. | : 11,634,500 B2 | Page 1 of 1 |
| APPLICATION NO. | : 17/012942 | |
| DATED | : April 25, 2023 | |
| INVENTOR(S) | : Grandal et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 170 days.

Signed and Sealed this
Thirty-first Day of December, 2024

Derrick Brent
*Acting Director of the United States Patent and Trademark Office*

SEQUENCE LISTING

```
<160> NUMBER OF SEQ ID NOS: 45

<210> SEQ ID NO 1
<211> LENGTH: 369
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic polynucleotide"

<400> SEQUENCE: 1
gaggtgcagc tggtggagtc tggcggcggc ctggtgcagc caggcagaag cctgagactg    60
tcttgtgctg cctctggctt ttccttcgac gattacgcta tgcactgggt gcggcaggct   120
cctggcaagg gcctggagtg ggtgtctggc atcagctggc actccgataa catcggctac   180
gctgattccg tgaagggcag attcaccatc tccagagaca tgccaagaa ctccctgtac    240 ctgcagatga actccctgag agctgaggat accgcctttt actattgcgc caaggatggc   300
ccaagatata ggggctccta ttactacttc gactattggg gccagggcac actggtgaca   360
gtctcgagt                                                          369

<210> SEQ ID NO 2
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2
gaggtgcagc tggtggagag cggcggcggc ctggtgcagc ctggcagatc tctgagactg    60
tcttgcgtgg cttctggttt tactttttgat gactatgcca tgcactgggt gcggcaggct   120
ccaggcaagg gcctggagtg ggtgtctggc atcagctgga attccggctc tatcggctac   180
gctgacagcg tgaaaggcag attcaccatc tccagagaca atgccaagaa cagcctgtac   240
ctgcagatga actccctgag agctgaggat accgctttct attactgcgc tcagggcggc   300
tatgctatcc tgaccgccct ggagtactgg ggccagggca ccctggtgac agtctcgagt   360

<210> SEQ ID NO 3
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3
gaggtgcagc tggtggagtc tggcggcggc ctggtgcaac caggcagaag cctgagactg    60
tcttgtgctg cctccggttt tactttcgat gacttcgcta tgcattgggt gcggcaggcc   120
cctggcaagg gcctggagtg ggtgtctggc atctcttgga atagcggcaa catcggctac   180
gccgactctg tgaagggcag attcaccatc tccagagaca cgccaagaa ctccctgtat    240 ctccaaatga actccctgag agctgaggat accgctctgt actattgcgc caaggataag   300
tccggctctc cttactatta ctacggcatg gacgtgtggg gccagggcac aatggtgacc   360
gtctcgagt                                                          369

<210> SEQ ID NO 4
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4

```
gaggtgcagc tggtggagtc tgcggcggc ctggtgcagc caggcggctc cctgagactg      60
tcttgtgctg cctccggctt tagcttctcc acctattgga tgaactgggt gcgccaggcc    120
ccaggcaagg gcctggagtg ggtggccaat atcaagcagg atggctccga gaagtactat    180
gtggactccg tgaagggcag attcaccatc tccagagaca atgccaagaa ctccctgtat    240
ctgcagatga actccctgag agccgaggat accgccgtgt actattgtgc cagggatatc    300
agctcctctt ggttttacta ttacggcatg gacgtgtggg gccagggcac aaccgtgacc    360
gtctcgagt                                                             369
```

<210> SEQ ID NO 5
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 5

```
gacatccaga tgacccagag cccttctaca ctgtccgcca gcgtgggcga tagggtgacc      60
atcacatgcc gggcctctca gtccatcagc aactggctgg cttggtacca gcagaagccc    120
ggcaaggccc ctaagctgct gatctataag gcttccagcc tggagagcgg cgtgccatct    180
agattctctg gctccggcag cggcaccgag tttaccctga caatctcttc cctgcagcca    240
gacgatttcg ctacatacta ttgtcagcag tacaattctt attcccccat caccttttggc   300 cagggcacac gcctggagat caag                                            324
```

<210> SEQ ID NO 6
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6

```
gacatccaga tgacccagtc cccttccagc ctgtccgcct ccgtgggcga tagggtgacc      60
atcacatgcc gggcctctca gggcatctcc aactacctgg cttggttcca gcagaagccc    120
ggcaaggccc ctaagagcct gatctatgcc gcttctagcc tgcaaagcgg cgtgccatct    180
aagttctctg gctccggcag cggcaccgac tttaccctga caatcagctc tctgcagcca    240
gaggatttcg ccacatacta ttgtcagcag tacaattctt atccccctgac attcggcggt    300 ggaactaagg tggagatcaa g                                               321
```

<210> SEQ ID NO 7
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7

```
gacatccaga tgacccagag cccctcctcc gtgtccgcct ccgtgggcga tagagtgacc      60
atcacatgca gggctacaca gggaatctct aggcggctgg cttggtacca gcagaagccc    120
```

```
ggcaaggccc ctaagctgct gatctatgcc gcttctagcc tgcaatctgg cgtgccatcc    180
aggttctctg gatccggaag cggaaccgac tttaccctga caatcagctc tctgcagcca    240
gaggatttcg ccacatacta ttgtcagcag ctaactcct tccccctgac tttcggcggt     300
ggaacaaaag tggagatcaa g                                              321
```

<210> SEQ ID NO 8
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8

```
gacatccagc tgacacagag cccatctttc ctgtccgcct ccgtgggcga tagggtgacc    60
atcacatgcc gggcctctca gggcatctcc agctacctgg cttggtatca gcagaagcca    120
ggcaaggccc ccaagctgct gatctacgct gcttctaccc tgcagtccgg agtgcctagc    180
aggttctctg ctccggcag cggcacagag tttaccctga caatctctag cctgcaacca    240
gaggacttcg ccacctacta ttgtcagcag ctgaactcct atcccctac attcggcggt    300 ggaaccaaag tcgaaatcaa g                                              321
```

<210> SEQ ID NO 9
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp His Ser Asp Asn Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Phe Tyr Tyr Cys
            85                  90                  95

Ala Lys Asp Gly Pro Arg Tyr Arg Gly Ser Tyr Tyr Tyr Phe Asp Tyr
            100                 105                 110

Trp Gly Gln Gly Thr Leu Val Thr Val Ser Ser
        115                 120

<210> SEQ ID NO 10
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

-continued

```
<400> SEQUENCE: 10

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Phe Tyr Tyr Cys
                85                  90                  95

Ala Gln Gly Gly Tyr Ala Ile Leu Thr Ala Leu Glu Tyr Trp Gly Gln
            100                 105                 110

Gly Thr Leu Val Thr Val Ser Ser
        115                 120

<210> SEQ ID NO 11
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Phe
            20                  25                  30

Ala Met His Trp Val Arg Gln Ala Pro Gly Lys Gly Leu Glu Trp Val
        35                  40                  45

Ser Gly Ile Ser Trp Asn Ser Gly Asn Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Lys Ser Gly Ser Pro Tyr Tyr Tyr Gly Met Asp Val
            100                 105                 110

Trp Gly Gln Gly Thr Met Val Thr Val Ser Ser
        115                 120

<210> SEQ ID NO 12
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Thr Tyr
            20                  25                  30
```

```
Trp Met Asn Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ile Ser Ser Ser Trp Phe Tyr Tyr Gly Met Asp Val
                100                 105                 110

Trp Gly Gln Gly Thr Thr Val Thr Val Ser Ser
        115                 120
```

```
<210> SEQ ID NO 13
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Asn Trp
                 20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Pro
                 85                  90                  95

Ile Thr Phe Gly Gln Gly Thr Arg Leu Glu Ile Lys
                100                 105
```

```
<210> SEQ ID NO 14
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
                 20                  25                  30

Leu Ala Trp Phe Gln Gln Lys Pro Gly Lys Ala Pro Lys Ser Leu Ile
         35                  40                  45

Tyr Ala Ala Ser Ser Leu Gln Ser Gly Val Pro Ser Lys Phe Ser Gly
 50                  55                  60

Ser Gly Ser Gly Thr Asp Phe Thr Leu Thr Ile Ser Ser Leu Gln Pro
 65                  70                  75                  80
```

-continued

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 15
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Asp Ile Gln Met Thr Gln Ser Pro Ser Val Ser Ala Ser Val Gly
1               5                   10                  15

Asp Arg Val Thr Ile Thr Cys Arg Ala Thr Gln Gly Ile Ser Arg Arg
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 16
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Pro
                85                  90                  95

Thr Phe Gly Gly Gly Thr Lys Val Glu Ile Lys
            100                 105

<210> SEQ ID NO 17
<211> LENGTH: 8
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 17

Gly Phe Ser Phe Asp Asp Tyr Ala
1               5

<210> SEQ ID NO 18
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Ile Ser Trp His Ser Asp Asn Ile
1               5

<210> SEQ ID NO 19
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Cys Ala Lys Asp Gly Pro Arg Tyr Arg Gly Ser Tyr Tyr Tyr Phe Asp
1               5                   10                  15

Tyr Trp

<210> SEQ ID NO 20
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Gln Ser Ile Ser Asn Trp
1               5

<210> SEQ ID NO 21
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Lys Ala Ser
1

<210> SEQ ID NO 22
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 22

Cys Gln Gln Tyr Asn Ser Tyr Ser Pro Ile Thr Phe
1               5                   10

<210> SEQ ID NO 23
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Gly Phe Thr Phe Asp Asp Tyr Ala
1               5

<210> SEQ ID NO 24
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Ile Ser Trp Asn Ser Gly Ser Ile
1               5

<210> SEQ ID NO 25
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Cys Ala Gln Gly Gly Tyr Ala Ile Leu Thr Ala Leu Glu Tyr Trp
1               5                   10                  15

<210> SEQ ID NO 26
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Gln Gly Ile Ser Asn Tyr
1               5

<210> SEQ ID NO 27
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Ala Ala Ser

-continued

```
<210> SEQ ID NO 28
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Cys Gln Gln Tyr Asn Ser Tyr Pro Leu Thr Phe
1               5                   10

<210> SEQ ID NO 29
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Gly Phe Thr Phe Asp Asp Phe Ala
1               5

<210> SEQ ID NO 30
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Ile Ser Trp Asn Ser Gly Asn Ile
1               5

<210> SEQ ID NO 31
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Cys Ala Lys Asp Lys Ser Gly Ser Pro Tyr Tyr Tyr Tyr Gly Met Asp
1               5                   10                  15

Val Trp

<210> SEQ ID NO 32
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gln Gly Ile Ser Arg Arg
1               5
```

```
<210> SEQ ID NO 33
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ala Ala Ser
1

<210> SEQ ID NO 34
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Cys Gln Gln Ala Asn Ser Phe Pro Leu Thr Phe
1               5                   10

<210> SEQ ID NO 35
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Gly Phe Ser Phe Ser Thr Tyr Trp
1               5

<210> SEQ ID NO 36
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Ile Lys Gln Asp Gly Ser Glu Lys
1               5

<210> SEQ ID NO 37
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Cys Ala Arg Asp Ile Ser Ser Ser Trp Phe Tyr Tyr Tyr Gly Met Asp
1               5                   10                  15

Val Trp

<210> SEQ ID NO 38
```

<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 38

Gln Gly Ile Ser Ser Tyr
1               5

<210> SEQ ID NO 39
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 39

Ala Ala Ser
1

<210> SEQ ID NO 40
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 40

Cys Gln Gln Leu Asn Ser Tyr Pro Pro Thr Phe
1               5                   10

<210> SEQ ID NO 41
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

```
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 42
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
                100                 105

<210> SEQ ID NO 43
<211> LENGTH: 574
<212> TYPE: PRT
<213> ORGANISM: Homo sapiens

<400> SEQUENCE: 43
```

```
Met Cys Pro Arg Ala Arg Ala Pro Ala Thr Leu Leu Ala Leu
1               5                   10                  15

Gly Ala Val Leu Trp Pro Ala Ala Gly Ala Trp Glu Leu Thr Ile Leu
                20                  25                  30

His Thr Asn Asp Val His Ser Arg Leu Glu Gln Thr Ser Glu Asp Ser
            35                  40                  45

Ser Lys Cys Val Asn Ala Ser Arg Cys Met Gly Gly Val Ala Arg Leu
50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
                100                 105                 110

Met Ala Leu Gly Asn His Glu Phe Asp Asn Gly Val Glu Gly Leu Ile
            115                 120                 125

Glu Pro Leu Leu Lys Glu Ala Lys Phe Pro Ile Leu Ser Ala Asn Ile
130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
            195                 200                 205

Thr Leu Asn Val Asn Lys Ile Ile Ala Leu Gly His Ser Gly Phe Glu
210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
            275                 280                 285

Tyr Leu Lys Ile Glu Phe Asp Glu Arg Gly Asn Val Ile Ser Ser His
290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
            355                 360                 365

Ile Asn Asn Asn Leu Arg His Thr Asp Glu Met Phe Trp Asn His Val
370                 375                 380

Ser Met Cys Ile Leu Asn Gly Gly Gly Ile Arg Ser Pro Ile Asp Glu
385                 390                 395                 400

Arg Asn Asn Gly Thr Ile Thr Trp Glu Asn Leu Ala Ala Val Leu Pro
                405                 410                 415
```

```
Phe Gly Gly Thr Phe Asp Leu Val Gln Leu Lys Gly Ser Thr Leu Lys
            420             425             430

Lys Ala Phe Glu His Ser Val His Arg Tyr Gly Gln Ser Thr Gly Glu
        435             440             445

Phe Leu Gln Val Gly Gly Ile His Val Val Tyr Asp Leu Ser Arg Lys
    450             455             460

Pro Gly Asp Arg Val Val Lys Leu Asp Val Leu Cys Thr Lys Cys Arg
465             470             475             480

Val Pro Ser Tyr Asp Pro Leu Lys Met Asp Glu Val Tyr Lys Val Ile
                485             490             495

Leu Pro Asn Phe Leu Ala Asn Gly Gly Asp Gly Phe Gln Met Ile Lys
            500             505             510

Asp Glu Leu Leu Arg His Asp Ser Gly Asp Gln Asp Ile Asn Val Val
            515             520             525

Ser Thr Tyr Ile Ser Lys Met Lys Val Ile Tyr Pro Ala Val Glu Gly
    530             535             540

Arg Ile Lys Phe Ser Thr Gly Ser His Cys His Gly Ser Phe Ser Leu
545             550             555             560

Ile Phe Leu Ser Leu Trp Ala Val Ile Phe Val Leu Tyr Gln
                565             570

<210> SEQ ID NO 44
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gly Gly Gly Gly Ser Gly Gly Gly Gly Ser Gly Gly Gly Gly Ser
1               5                   10                  15

<210> SEQ ID NO 45
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 45

His His His His His His
1               5
```